(12) United States Patent
Tamura et al.

(10) Patent No.: US 8,715,626 B2
(45) Date of Patent: May 6, 2014

(54) COSMETIC FOR HAIR CONTAINING CO-MODIFIED ORGANOPOLYSILOXANE

(75) Inventors: Seiki Tamura, Ichihara (JP); Tomohiro Iimura, Sodegaura (JP); Tatsuo Souda, Ichihara (JP); Haruhiko Furukawa, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 13/812,795

(22) PCT Filed: Jul. 28, 2011

(86) PCT No.: PCT/JP2011/067813
§ 371 (c)(1),
(2), (4) Date: Feb. 15, 2013

(87) PCT Pub. No.: WO2012/015070
PCT Pub. Date: Feb. 2, 2012

(65) Prior Publication Data
US 2013/0142748 A1 Jun. 6, 2013

(30) Foreign Application Priority Data
Jul. 30, 2010 (JP) .............................. P2010-173093

(51) Int. Cl.
- *A61P 31/04* (2006.01)
- *A61P 17/02* (2006.01)
- *A61K 38/43* (2006.01)
- *A61Q 19/08* (2006.01)
- *A61Q 1/02* (2006.01)
- *A61K 47/34* (2006.01)
- *A61K 8/89* (2006.01)

(52) U.S. Cl.
USPC ........... 424/59; 424/63; 424/70.12; 424/70.9; 424/94.1; 514/772.3; 528/25

(58) Field of Classification Search
None
See application file for complete search history.

(56) References Cited

U.S. PATENT DOCUMENTS

| | | | |
|---|---|---|---|
| 4,261,875 | A | 4/1981 | LeBoeuf |
| 4,980,167 | A | 12/1990 | Harashima et al. |
| 5,628,989 | A | 5/1997 | Harashima et al. |
| 5,654,362 | A | 8/1997 | Schulz, Jr. et al. |
| 5,939,478 | A | 8/1999 | Beck et al. |
| 5,981,680 | A | 11/1999 | Petroff et al. |
| 6,238,656 | B1 | 5/2001 | Morita et al. |
| 6,280,748 | B1 | 8/2001 | Morita et al. |
| 6,353,076 | B1 | 3/2002 | Barr et al. |
| 2004/0146472 | A1 | 7/2004 | Nakanishi |
| 2007/0149703 | A1 | 6/2007 | Caprasse et al. |

FOREIGN PATENT DOCUMENTS

| | | |
|---|---|---|
| EP | 0963751 A2 | 12/1999 |
| EP | 1213316 A2 | 6/2002 |
| JP | 55-108881 A | 8/1980 |
| JP | 63-183517 A | 7/1988 |
| JP | 02243612 A | 9/1990 |
| JP | 08-012524 A | 1/1996 |
| JP | 08-12545 A | 1/1996 |
| JP | 08-012546 A | 1/1996 |
| JP | 09-241511 A | 9/1997 |
| JP | 10-36219 A | 2/1998 |
| JP | 11193331 A | 7/1999 |
| JP | 2000038450 A | 2/2000 |
| JP | 2000063225 A | 2/2000 |
| JP | 2000281523 A | 10/2000 |
| JP | 2001512164 A | 8/2001 |
| JP | 2002179798 A | 6/2002 |
| JP | 2004-231607 A | 8/2004 |
| JP | 2005-097152 A | 4/2005 |
| JP | 2006-265339 A | 10/2006 |
| JP | 4009382 B2 | 11/2007 |
| JP | 2007532754 A | 11/2007 |

OTHER PUBLICATIONS

English language abstract and translation for JP 4009382 extracted from espacenet.com and PAJ databases on May 6, 2013, 37 pages.
English language abstract for JP 2000038450 extracted from espacenet.com database on May 6, 2013, 2 pages.
English language abstract for JP 2000063225 extracted from espacenet.com database on May 6, 2013, 2 pages.
English language abstract for JP 2000281523 extracted from espacenet.com database on May 6, 2013, 1 pages.
English language abstract not found for JP 2001512164. However see English language equivalent US 6,353,076. Original document extracted from espacenet.com database on May 6, 2013, 68 pages.
English language abstract for JP 2002179798 extracted from espacenet.com database on May 6, 2013, 2 pages.
English language abstract and translation for JP 2004-231607 extracted from PAJ database on May 6, 2013, 66 pages.
English language abstract and translation for JP 2005-097152 extracted from PAJ database on May 6, 2013, 57 pages.

(Continued)

Primary Examiner — Robert A Wax
Assistant Examiner — Randeep Singh
(74) Attorney, Agent, or Firm — Howard & Howard Attorneys PLLC

(57) ABSTRACT

The present invention provides a cosmetic for hair in which smooth combability without a frictional sensation during cleansing and applying to hair, namely during wetting, the aforementioned effects are not lost by a rinsing operation, smooth combability during and after drying the hair is exhibited, a moisturizing feeling on touch is exhibited without stickiness, and a flexible styling sensation is provided to the hair. A co-modified organopolysiloxane having both a specified hydrophilic group and a siloxane dendron structure-containing group is blended in a cosmetic for hair as an essential component.

16 Claims, No Drawings

(56) References Cited

OTHER PUBLICATIONS

English language abstract and translation for JP 2006-265339 extracted from PAJ database on May 6, 2013, 50 pages.
English language abstract not found for JP 2007-532754. However see English language equivalent US 2007/0149703. Original document extracted from espacenet.com database on May 6, 2013, 38 pages.
English language abstract for JP 02243612 extracted from PAJ database on May 6, 2013, 1 page.
English language abstract and translation for JP 08-012524 extracted from PAJ database on May 6, 2013, 59 pages.
English language abstract for JP 08-12545 extracted from PAJ database on May 6, 2013, 1 page.
English language abstract and translation for JP 09-241511 extracted from PAJ database on May 6, 2013, 26 pages.
English language abstract and translation for JP 08-012546 extracted from PAJ database on May 6, 2013, 32 pages.
English language abstract and translation for JP 10-036219 extracted from PAJ database on May 6, 2013, 36 pages.
English language abstract for JP 11193331 extracted from PAJ database on May 6, 2013, 1 page.
English language abstract not found for JP 55108881. However see English language equivalent US 4,261,875. Original document extracted from espacenet.com database on May 6, 2013, 6 pages.
English language abstract for JP 63-183517 extracted from PAJ database on May 6, 2013, 1 page.
PCT International Search Report PCT/JP2011/067813, dated Dec. 1, 2011, 3 pages.

COSMETIC FOR HAIR CONTAINING CO-MODIFIED ORGANOPOLYSILOXANE

RELATED APPLICATIONS

This application is the National Stage of International Patent Application No. PCT/JP2011/067813, filed on Jul. 28, 2011, which claims priority to and all the advantages of Japanese Patent Application No. 2010-173093, filed on Jul. 30, 2010, the content of which is incorporated herein by reference.

TECHNICAL FIELD

The present invention relates to a cosmetic for hair comprising a co-modified organopolysiloxane possessing a hydrophilic group and a siloxane dendron structure-containing group.

BACKGROUND ART

Heretofore, there has been a problem in that due to chemical or physical damage of hair received during styling the hair, glossiness of the hair is impaired, roughness of hair occurs, or combability with a comb or fingers, or the like is impaired, and as a result, poofy hair may be obtained and hair styling may be difficult. In order to overcome the aforementioned problem, a hair treatment with a hair conditioning cosmetic such as a rinse has been carried out. In order to enhance the aforementioned treatment effects and impart softness, smoothness, styling properties or the like to hair, various silicones have been used.

Also in order to improve a feeling on touch during cleansing hair with a cosmetic for use in cleansing hair such as a shampoo, and impart the aforementioned treatment effects to the hair after drying, various silicones have also been used in the same manner as described above. In addition, in a cosmetic for styling hair used for fixing the hair style, various silicones have also been blended for improving smoothness and reducing a frictional sensation. The effects obtained by blending the aforementioned silicones are based on softness, smoothness, adhering properties, and film-forming properties which the silicones inherently possess. For this reason, silicone polymers having various structures have been proposed.

For example, a cosmetic for hair comprising a dimethyl- or methylphenylsilicone with a high molecular weight for preventing damaged hair such as split ends, hair breakage or the like while imparting glossiness and a smooth feeling on touch to hair, has been proposed (see JP-A-S63-183517 and the like). However, there are problems in that durability of the aforementioned effects thereof is poor and remarkably reduced by brushing or treatment with a dryer, and a frictional sensation occurs even under a wet condition.

Alternatively, a cosmetic for hair comprising a silicone in which a polyether group is introduced as a hydrophilic group has been proposed (see JP-A-S55-108881 and the like). By virtue of the aforementioned silicone, a moisturizing sensation is improved and an effect of preventing a frictional sensation under a wet condition can be obtained. On the other hand, there are problems in that stickiness is exhibited, smoothness of a feeling on touch after drying is poor, and a heavy feeling on touch is exhibited. Therefore, the usage range thereof has been restricted.

In addition, a process in which a silicone having a polyglycerol group as a hydrophilic group is blended into a cosmetic for hair (see JP-A-2005-097152) or a process in which a silicone having a polyglycerol group as a hydrophilic group is blended into a cleansing composition including a composition for hair (see JP-A-2006-265339) have been proposed. In addition, examples in which a branched silicone in which a silicone is grafted is blended into a cosmetic, in addition to a polyhydric alcohol group such as a polyglycerol group have been proposed (see JP-A-2002-179798 and JP-A-2004-231607). The polyglycerol groups also exhibit superior adhering properties to hair and an effect of preventing stickiness and preventing a frictional sensation under a wet condition may be obtained. The aforementioned effects are not still sufficient, and in particular, further improvement in smoothness and amelioration of a heavy feeling on touch after drying may have been required.

DISCLOSURE OF INVENTION

Technical Problems

The present invention has been made in view of the circumstances of the aforementioned prior art. An objective of the present invention is to provide a cosmetic for hair in which smooth combability with fingers without exhibiting a frictional sensation during cleansing and applying to hair, namely during wetting, the aforementioned effects are not lost by rinsing operation, smooth combability with a comb or fingers during and after drying the hair is exhibited, a moisturizing feeling on touch is exhibited without stickiness, and/or a flexible styling sensation is provided to the hair.

In addition, another objective of the present invention is also to provide a cosmetic for hair which is superior in view of cleansing properties such as good foaming properties, a feeling on touch of foam and the like.

In addition, another objective of the present invention is also to provide a cosmetic for hair in which the aforementioned various effects can be maintained.

Technical Solution

As a result of diligent studies in order to achieve the aforementioned objectives, the inventors of the present invention have completed the present invention. The objective of the present invention can be achieved by a cosmetic for hair comprising (A) a co-modified organopolysiloxane represented by the following general formula (1):

$$R^1_a L^1_b Q_c SiO_{(4-a-b-c)/2} \quad (1)$$

wherein
$R^1$ represents a monovalent organic group, with the proviso that L and Q are excluded therefrom, a hydrogen atom or a hydroxyl group;
$L^1$ represents a silylalkyl group having a siloxane dendron structure, in the case of i=1, represented by the following general formula (2):

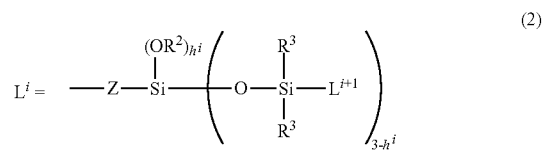

$$L^i = -Z-Si(OR^2)_{h^i}\left(-O-Si(R^3)_2 -L^{i+1}\right)_{3-h^i} \quad (2)$$

wherein
$R^2$ represents a substituted or non-substituted, and linear or branched monovalent hydrocarbon group having 1 to 30 carbon atoms;
$R^3$ independently represents an alkyl group having 1 to 6 carbon atoms or a phenyl group;
Z represents a divalent organic group;

i specifies the number of generations of the aforementioned silylalkyl group, represented by $L^i$, in the case in which the number of generations of the aforementioned silylalkyl group, which is the number of repetitions of the aforementioned silylalkyl group, is k, i is an integer ranging from 1 to k, and the number of generations k is an integer ranging from 1 to 10;

$L^{i+1}$ is the aforementioned silylalkyl group in the case of i<k, and $L^{i+1}$ is $R^3$ in the case of i=k; and $h^i$ is a number ranging from 0 to 3;

Q represents a hydrophilic group which binds to a silicon atom via a linking group with two or more valances and comprises at least one hydrophilic unit selected from hydrophilic units represented by the following structural formulae (3-1) to (3-4):

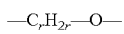 (3-1)

wherein r is a number ranging from 1 to 6,

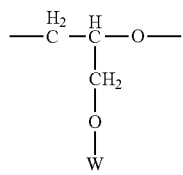 (3-2)

wherein W represents a hydrogen atom or an alkyl group having 1 to 20 carbon atoms,

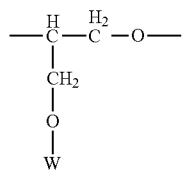 (3-3)

wherein W represents the same group as defined above, and

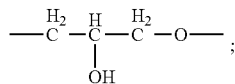 (3-4)

and
each of a, b and c is independently a number having the following range: 1.0≤a≤2.5, 0.0001≤b≤1.5, and 0.0001≤c≤1.5.

In the aforementioned general formula (1), $L^1$ is preferably a functional group represented by the following general formula (2-1):

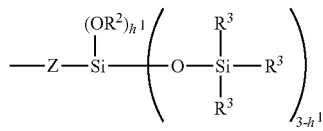 (2-1)

or represented by the following general formula (2-2):

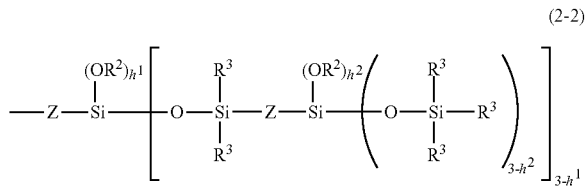 (2-2)

wherein $R^2$, $R^3$ and Z are the same as defined above; and each of $h^1$ and $h^2$ is independently a number ranging from 0 to 3.

In the aforementioned general formula (1), Q preferably further comprises at least one hydrophilic unit selected from hydrophilic units represented by the following structural formulae (3-5) to (3-7):

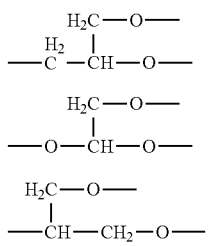

(3-5)

(3-6)

(3-7)

In particular, Q is preferably a hydrophilic group represented by any one of the following general formulae (4-1) to (4-4):

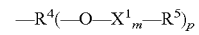 (4-1)

wherein $R^4$ is an organic group having (p+1) valences;
p is an integer ranging from 1 to 3;
each $X^1$ is independently one or more hydrophilic units selected from hydrophilic units represented by the aforementioned structural formulae (3-1) to (3-4);
m is a number ranging from 1 to 100; and
$R^5$ is a hydrogen atom or a group selected from the group consisting of an alkyl group having 1 to 20 carbon atoms, an acyl group and a glycidyl group,

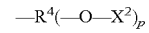 (4-2)

wherein $R^4$ is the same group as defined above;
p is the same number as defined above; and
$X^2$ is a hydrophilic group represented by the following structural formula (4-2-1):

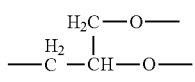 (4-2-1)

wherein at least one hydrophilic unit selected from the hydrophilic units represented by the aforementioned structural formulae (3-1) to (3-4) independently binds to each of the two oxygen atoms,

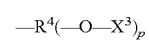 (4-3)

wherein $R^4$ is the same group as defined above;

p is the same number as defined above; and
$X^3$ is a hydrophilic group represented by the following structural formula (4-3-1):

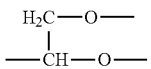
(4-3-1)

wherein at least one hydrophilic unit selected from the hydrophilic units represented by the aforementioned structural formulae (3-1) to (3-4) independently binds to each of the two oxygen atoms, $$-R^4(-O-X^4)_p \quad (4-4)$$

wherein $R^4$ is the same group as defined above;
p is the same number as defined above; and
$X^4$ is a hydrophilic group represented by the following structural formula (4-4-1):

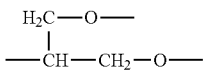
(4-4-1)

wherein at least one hydrophilic unit selected from the hydrophilic units represented by the aforementioned structural formulae (3-1) to (3-4) independently binds to each of the two oxygen atoms.

As the aforementioned (A) co-modified organopolysiloxane, one represented by the following structural formula (1-1):

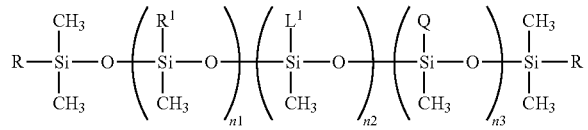
(1-1)

wherein
$R^1$, $L^1$ and Q are the same groups as defined above;
R is a group selected from $R^1$, $L^1$ and Q;
each of n1, n2 and n3 is independently a number ranging from 0 to 2,000, and n1+n2+n3 is a number ranging from 1 to 2,000, with the proviso that in the case of n2=0, at least one R is $L^1$, and in the case of n3=0, at least one R is Q, is preferred.

The aforementioned (A) co-modified organopolysiloxane may be one represented by the following structural formula (1-1-1) or (1-1-2):

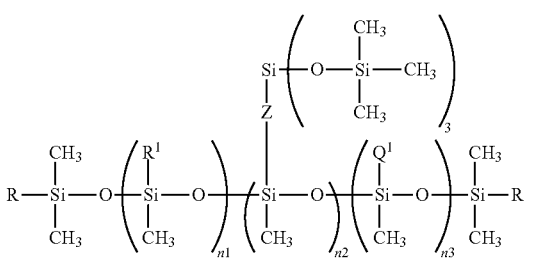
(1-1-1)

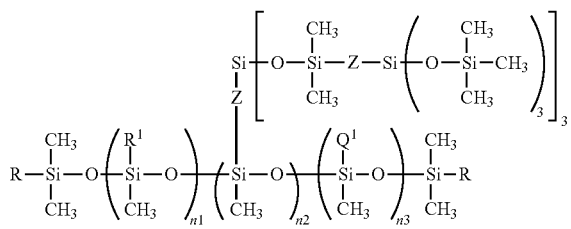
(1-1-2)

wherein
Z is the same group as defined above;
each R is independently a group selected from $R^1$, $L^1$ and $Q^1$;
$R^1$ and $L^1$ are the same groups as defined above;
$Q^1$ is a hydrophilic group selected from the group consisting of the following structural formulae (4-1-2), (4-2-2), (4-3-2) and (4-4-2):

$$-R^4(-O-X^1{}_m-R^5)_p \quad (4\text{-}1\text{-}2)$$

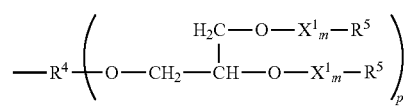
(4-2-2)

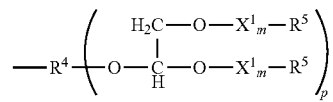
(4-3-2)

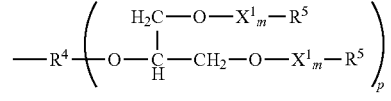
(4-4-2)

wherein $R^4$, p, $X^1$, m and $R^5$ are the same groups as defined above,
n1 is a number ranging from 10 to 2,000; n2 is a number ranging from 0 to 250; and n3 is a number ranging from 0 to 250, with the proviso that in the case of n2=0, at least one R is $L^1$, and in the case of n3=0, at least one R is $Q^1$.

In the aforementioned structural formula (1-1-1) or (1-1-2), Z is independently and preferably a group selected from divalent organic groups represented by the following general formulae:

$$-R^6-$$

$$-R^6-CO-$$

$$-R^6-COO-R^7-$$

$$-CO-R^6-$$

$$-R^6-COO-R^7-$$

$$-R^6-CONH-R^7-$$

$$-R^6-R^7-$$

wherein
each $R^6$ independently represents a substituted or non-substituted, and linear or branched, alkylene or alkenylene group having 2 to 22 carbon atoms or an arylene group having 6 to 22 carbon atoms;

$R^7$ is a group selected from the group consisting of the following groups:

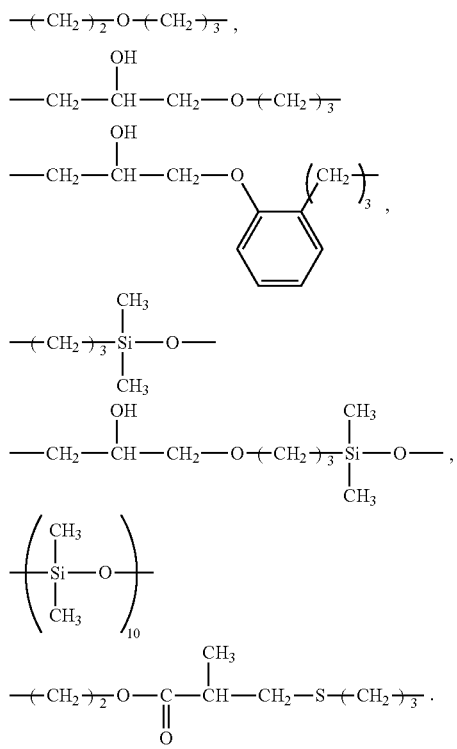

In the aforementioned structural formulae (4-1-2), (4-2-2), (4-3-2) and (4-4-2), groups are preferred, in which p is 1; and $R^4$ is a group selected from divalent organic groups represented by the following general formulae (5-1), (5-1-2), (5-1-3), and (5-2):

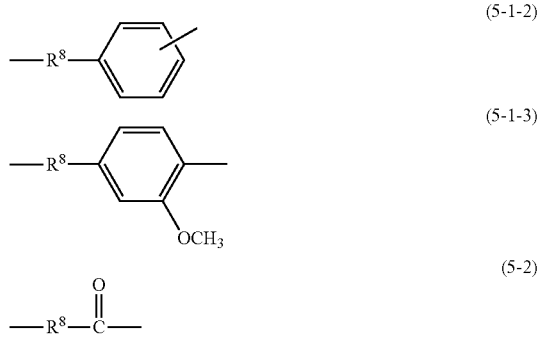

wherein
each $R^8$ independently represents a substituted or non-substituted, and linear or branched, alkylene or alkenylene group having 2 to 22 carbon atoms or an arylene group having 6 to 22 carbon atoms.

The cosmetic for hair of the present invention preferably further comprises (B) an oil agent.

The cosmetic for hair of the present invention preferably further comprises (C) a surfactant.

The cosmetic for hair of the present invention preferably further comprises (D) a water-soluble polymer.

The cosmetic for hair of the present invention can be in the form of a cosmetic for cleansing hair, a cosmetic for conditioning hair, a cosmetic for styling hair, or a cosmetic for dyeing hair.

The cosmetic for cleansing hair of the present invention preferably further comprises (C1) an anionic surfactant and (D1) a cationic water-soluble polymer.

The cosmetic for conditioning hair of the present invention preferably further comprises (B2-1) a higher alcohol and (C2) a cationic surfactant.

The cosmetic for styling hair of the present invention is preferably in the form of a liquid, a cream, a solid, a paste, a gel, a mousse, or a spray.

The cosmetic for dyeing hair of the present invention preferably further comprises (K) an oxidation hair-dyeing agent and/or (L) a direct dye.

Advantageous Effects of Invention

The cosmetic for hair of the present invention comprises a co-modified organopolysiloxane in which a specified hydrophilic group and a siloxane dendron structure-containing group as an essential component, and for this reason, smooth combability with fingers can be provided without a frictional sensation, both during wetting and during drying. Furthermore, a superior foaming property and a superior feeling on touch of foam are exhibited, smooth combability with a comb or fingers during drying and a moisturizing feeling on touch can be provided without uncomfortable stickiness, and a good and flexible styling sensation can be provided to hair. In addition, the cosmetic compositions for hair of the present invention can exhibit superior durability of the aforementioned effects. Therefore, the cosmetics for hair of the present invention can be preferably used as a cosmetic for cleansing hair, a cosmetic for conditioning hair, a cosmetic for styling hair, or a cosmetic for dyeing hair.

In addition, the aforementioned co-modified organopolysiloxane exhibits superior miscibility with each of the components contained in the cosmetic for hair. For this reason, the cosmetic for hair of the present invention exhibits superior stability and in particular, exhibits superior emulsification stability.

BEST MODES FOR CARRYING OUT THE INVENTION

The cosmetic for hair of the present invention comprises a co-modified organopolysiloxane represented by the following general formula (1):

$$R^1{}_a L^1{}_b Q_c SiO_{(4-a-b-c)/2} \quad (1).$$

The aforementioned (A) co-modified organopolysiloxane is a co-modified organopolysiloxane having a group ($-L^1$) with a siloxane dendron structure and a hydrophilic group ($-Q$) (hereinafter, a silylalkyl group, which is a group represented by $L^1$ in the aforementioned general formula (1) and which is represented by the following general formula (2) at the time of i=1, may be represented by "carbosiloxane dendrimer" or "silylalkyl group having a siloxane dendron structure" in some cases).

First, $R^1$, $L^1$ and Q in the aforementioned general formula (1) will be described in detail.

$R^1$ in the aforementioned general formula (1) is a monovalent organic group, a hydrogen atom or a hydroxyl group. The monovalent organic group is not particularly restricted as long as it is not a functional group corresponding to $L^1$ or Q. The monovalent organic group is preferably a substituted or non-substituted monovalent hydrocarbon group having 1 to 30 carbon atoms, a (meth)acryl group, an amide group, a carbinol group or a phenol group. As examples of substituted or non-substituted monovalent hydrocarbon groups, mention may be made of saturated aliphatic hydrocarbon groups such as a methyl group, an ethyl group, a propyl group, a butyl group, a pentyl group, a hexyl group, a heptyl group, an octyl group, a decyl group, a dodecyl group and the like; saturated alicyclic hydrocarbon groups such as a cyclopentyl group, a cyclohexyl group and the like; aromatic hydrocarbon groups such as a phenyl group, a tolyl group, a xylyl group, a naphthyl group and the like; substituted groups thereof in which the hydrogen atoms binding to the carbon atoms of the aforementioned groups are at least partially substituted with a halogen atom such as a fluorine atom or the like, or an organic group containing an epoxy group, an acyl group, a carboxyl group, an amino group, a methacryl group, a mercapto group or the like, with the proviso that all $R^1$s do not represent a hydrogen atom or a hydroxyl group.

In the co-modified organopolysiloxane according to the present invention, in order to provide a further functional property, a modifying group other than the group having a siloxane dendron structure (-$L^1$) and the hydrophilic group (-Q) may be introduced as $R^1$, and the organopolysiloxane can be designed. Namely, in the case of $R^1$ being a substituted monovalent hydrocarbon group, the substituent thereof can be appropriately selected from the aforementioned organic groups in accordance with a property and a usage to be provided. For example, in the case of using the co-modified organopolysiloxane as a raw material of a cosmetic, for the purpose of improving a sensation during use, a feeling on touch, and durability, an amino group, an amide group, an aminoethyl aminopropyl group, a carboxyl group or the like can be introduced as the substituent of the monovalent hydrocarbon group. Similarly, for the purpose of exhibiting a sensation during use which so-called middle-chain alkyl groups or long-chain alkyl groups possess, improving a feeling on touch after blending in a cosmetic for hair, or enhancing compatibility with other components, as a part of $R^1$, an alkyl group having 8 to 20 carbon atoms can be selected, in addition to an alkyl group having 1 to 4 carbon atoms such as a methyl group, an ethyl group or the like.

In particular, $R^1$ is preferably a monovalent hydrocarbon group or a monovalent fluorinated hydrocarbon group, having 1 to 20 carbon atoms. As examples of the monovalent hydrocarbon group having no aliphatic unsaturated bond belonging to $R^1$, mention may be made of alkyl groups such as a methyl group, an ethyl group, a propyl group, a butyl group, a pentyl group, a hexyl group and the like; aryl groups such as a phenyl group, a tolyl group, a xylyl group and the like; and aralkyl groups such as a benzyl group and the like. As examples of monovalent fluorinated hydrocarbon groups, mention may be made of perfluoroalkyl groups such as a trifluoropropyl group, a pentafluoroethyl group and the like. From an industrial point of view, $R^1$ is preferably a methyl group, an ethyl group, or a phenyl group, and in particular, 90% by mol to 100% by mol of all $R^1$s is preferably a group selected from the group consisting of a methyl group, an ethyl group and a phenyl group.

In the aforementioned general formula (1), a group represented by $L^1$ is a silylalkyl group having a siloxane dendron structure, and is defined as a silylalkyl group represented by the following general formula (2) in the case of i=1.

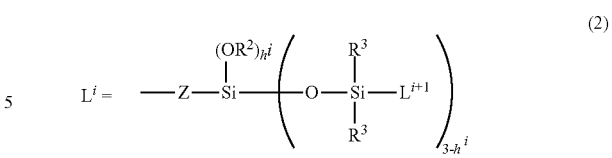

wherein
$R^2$ represents a substituted or non-substituted, and linear or branched monovalent hydrocarbon group having 1 to 30 carbon atoms;
$R^3$ independently represents an alkyl group having 1 to 6 carbon atoms or a phenyl group;
Z represents a divalent organic group;
i specifies the number of generations of the aforementioned silylalkyl group, represented by $L^1$, in the case in which the number of generations of the aforementioned silylalkyl group, which is the number of repetitions of the aforementioned silylalkyl group, is k, i is an integer ranging from 1 to k, and the number of generations k is an integer ranging from 1 to 10; and
$L^{i+1}$ is the aforementioned silylalkyl group in the case of i<k, and $L^{i+1}$ is $R^3$ in the case of i=k; and $h^i$ is a number ranging from 0 to 3.

The aforementioned silylalkyl group having a siloxane dendron structure includes a structure in which carbosiloxane units are spread in the form of a dendrimer, and is a functional group exhibiting increased water-repellency. In addition, superior balance of the combination with a hydrophilic group is exhibited, and at the time of using a cosmetic for hair in which the aforementioned co-modified organopolysiloxane is blended, an uncomfortable sticky sensation can be controlled and a refreshing and natural feeling on use can be provided. Furthermore, the aforementioned silylalkyl group having a siloxane dendron structure is a chemically stable functional group which is capable of imparting an advantageous property that widely-ranged cosmetic ingredients can be used in combined therewith.

As examples of substituted or non-substituted, and linear or branched monovalent hydrocarbon groups having 1 to 30 carbon atoms, represented by $R^3$ of the aforementioned general formula (2), mention may be made of, for example, alkyl groups such as a methyl group, an ethyl group, a propyl group, a butyl group, a pentyl group, a hexyl group, a heptyl group, an octyl group and the like; cycloalkyl groups such as a cyclopentyl group, a cyclohexyl group and the like; alkenyl groups such as a vinyl group, an allyl group, a butenyl group and the like; aryl groups such as a phenyl group, a tolyl group and the like; aralkyl groups such as a benzyl group and the like; substituted groups thereof in which the hydrogen atoms binding to the carbon atoms of the aforementioned groups are at least partially substituted with a halogen atom such as a fluorine atom or the like, or an organic group containing an epoxy group, a glycidyl group, an acyl group, a carboxyl group, an amino group, a methacryl group, a mercapto group or the like, with the proviso that the total number of the carbon atoms ranges from 1 to 30 carbon atoms.

Among alkyl groups having 1 to 6 carbon atoms or a phenyl group, represented by $R^3$ in the aforementioned general formula (2), as examples of alkyl groups having 1 to 6 carbon atoms, mention may be made of linear, branched or cyclic alkyl groups such as a methyl group, an ethyl group, a n-propyl group, an i-propyl group, a n-butyl group, an i-butyl group, a s-butyl group, a pentyl group, a neopentyl group, a cyclopentyl group, a hexyl group and the like.

In the aforementioned general formula (2), in the case of i=k, $R^3$ is preferably a methyl group or a phenyl group. In particular, in the case of i=k, a methyl group is preferred.

The aforementioned number of generations k is preferably an integer ranging from 1 to 3, and more preferably 1 or 2 from an industrial viewpoint. In each number of generations, the group represented by $L^1$ is represented as follows, wherein $R^2$, $R^3$ and Z are the same groups as described above.

In the case of the number of generations k=1, $L^1$ is represented by the following general formula (2-1):

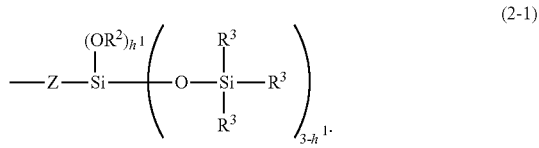

(2-1)

In the case of the number of generations k=2, $L^1$ is represented by the following general formula (2-2):

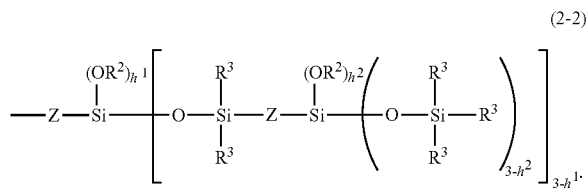

(2-2)

In the case of the number of generations k=3, $L^1$ is represented by the following general formula (2-3):

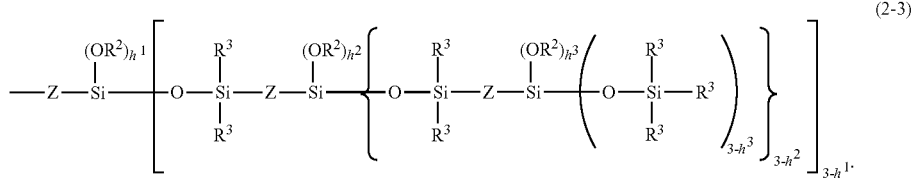

(2-3)

In the structures represented by the aforementioned general formulae (2-1) to (2-3) in the case of the number of generations ranging from 1 to 3, each of $h^1$, $h^2$ and $h^3$ is independently a number ranging from 0 to 3. The aforementioned $h^i$ is preferably a number particularly ranging from 0 to 1, and $h^i$ is, in particular, preferably 0.

In the aforementioned general formulae (2) and (2-1) to (2-3), each Z is independently a divalent organic group. In particular, as examples thereof, mention may be made of a divalent organic group formed by addition-reacting a silicon-binding hydrogen atom and a functional group having an unsaturated hydrocarbon group such as an alkenyl group, an acryloxy group, a methacryloxy group or the like at the terminal. In accordance with the method of introducing a silylalkyl group having a siloxane dendron structure, the functional groups can be appropriately selected and are not restricted to the aforementioned functional groups. Preferably, each Z is independently a group selected from divalent organic groups represented by the following general formulae (5-1) to (5-7):

$—R^6—$ (5-1)

$—R^6—CO—$ (5-2)

$—R^6—COO—R^7—$ (5-3)

$—CO—R^6—$ (5-4)

$—R^6—COO—R^7—$ (5-5)

$—R^6—CONH—R^7—$ (5-6)

$—R^6—R^7—$ (5-7)

In particular, Z in $L^1$ is preferably a divalent organic group represented by the aforementioned general formula (5-1), introduced by a reaction between a silicon-binding hydrogen atom and an alkenyl group. In the same manner, Z is preferably a divalent organic group represented by the aforementioned general formula (5-3), introduced by a reaction between a silicon-binding hydrogen atom and an unsaturated carboxylic ester group. On the other hand, in the silylalkyl group represented by $L^i$, in which the number of generations k is 2 or more, and $L^i$ is $L^2$ to $L^k$, Z is preferably an alkylene group having 2 to 10 carbon atoms, in particular, preferably a group selected from an ethylene group, a propylene group, a methylethylene group and a hexylene group, and most preferably an ethylene group.

In the aforementioned general formulae (5-1) to (5-7), each $R^6$ independently represents a substituted or non-substituted, and linear or branched alkylene or alkenylene group having 2 to 22 carbon atoms, or an arylene group having 6 to 22 carbon atoms. More particularly, as examples of $R^6$, mention may be made of linear alkylene groups such as an ethylene group, a propylene group, a butylene group, a hexylene group and the like; and branched alkylene groups such as a methylmethylene group, a methylethylene group, a 1-methylpentylene group, a 1,4-dimethylbutylene group and the like. $R^6$ is preferably a group selected from an ethylene group, a propylene group, a methylethylene group and a hexylene group.

In the aforementioned general formulae (5-3) and (5-5) to (5-7), $R^7$ is a group selected from divalent organic groups represented by the following formulae:

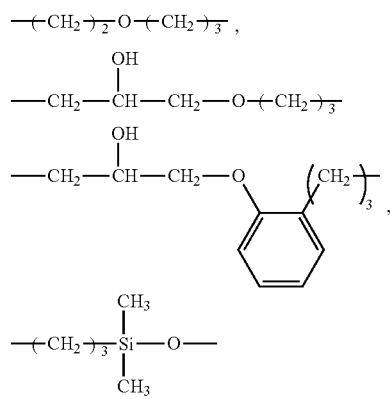

-continued

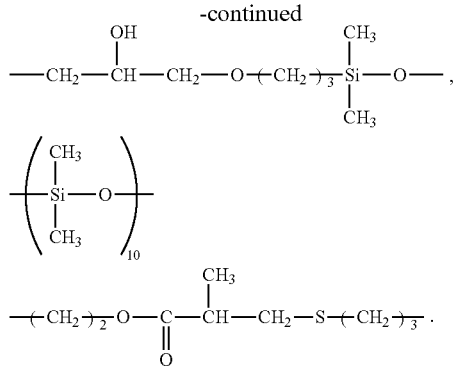

In the aforementioned general formula (1), Q is a hydrophilic group, and is defined as a hydrophilic group which binds to a silicon atom via a linking group with two or more valances and comprises at least one hydrophilic unit selected from hydrophilic units represented by the following structural formulae (3-1) to (3-4). Q which is the aforementioned hydrophilic group is a part providing a hydrophilic property to a co-modified organopolysiloxane, and is a functional group generally derived from a hydrophilic compound. As examples of Q as defined above, mention may be made of functional groups derived from alcohols, polyether compounds, polyglycerol compounds, polyglycidyl ether compounds, and hydrophilic sugars, with one or more valences in which the terminals of the molecular chain may be partially capped with a hydrocarbon.

More particularly, Q is a hydrophilic group which binds to a silicon atom via a linking group with two or more valances and comprises at least one hydrophilic unit selected from hydrophilic units represented by the following structural formulae (3-1) to (3-4).

$$—C_rH_{2r}—O— \qquad (3\text{-}1)$$

The hydrophilic unit represented by the aforementioned structural formula (3-1) is an oxyalkylene unit. In the formula, r is a number ranging from 1 to 6, and preferably ranging from 2 to 4. One or more hydrophilic units represented by the aforementioned structural formula (3-1) can be contained in the hydrophilic group which is Q. In addition, the hydrophilic unit represented by the aforementioned structural formula (3-1) is preferably contained in the hydrophilic group which is Q, as a polyoxyalkylene unit in which 2 to 50 hydrophilic units represented by the aforementioned structural formula (3-1) wherein each r independently ranges from 2 to 4 are linked.

In particular, in view of hydrophilic properties, the hydrophilic units represented by the aforementioned structural formula (3-1) are preferably contained in the hydrophilic group Q as a polyoxyalkylene unit in which 4 to 50 hydrophilic units represented by the aforementioned structural formula (3-1) are linked. One or more hydrophilic units represented by the aforementioned structural formula (3-1) are more preferably contained in Q as a polyoxyalkylene unit represented by the following formula (3-1-1).

$$—(C_2H_4O)_{t1}(C_3H_6O)_{t2}— \qquad (3\text{-}1\text{-}1)$$

wherein each of t1 and t2 is independently a number of 0 or more, t1+t2 is a number ranging from 4 to 50 and preferably ranging from 8 to 30.

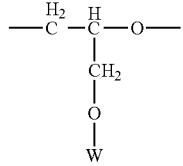

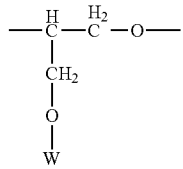

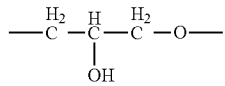

In the aforementioned structural formulae (3-2) to (3-4), W is a hydrogen atom or an alkyl group having 1 to 20 carbon atoms, and is preferably a hydrogen atom. In particular, in the case of W being a hydrogen atom, it is difficult to be oxidized under the air and it is difficult to produce an allergy antigenic compound, for example, formats and aldehydes such as formaldehyde, during storage over time. For this reason, there is an advantage in that environmental compatibility is increased.

The hydrophilic units represented by the aforementioned structural formulae (3-2) to (3-4) are hydrophilic units contained in hydrophilic groups derived from hydrophilic compounds selected from polyhydric alcohols containing glycerol as a main component, polyglycerols, polyglycidyl ethers and compounds in which the terminal hydroxyl groups of the aforementioned compounds are partially capped with hydrocarbon groups. The hydrophilic units are not restricted thereto.

In the aforementioned general formula (1), Q may be a hydrophilic group having no branched structure, such as a linear polyoxyalkylene group or the like, and may be a hydrophilic group in which a branched structure is present at a part of the functional group, such as a polyglycerol group or a polyglycidyl ether group.

More particularly, Q may bind to a silicon atom via a linking group having two or more valences, and may be a hydrophilic segment in which one or more hydrophilic units represented by the aforementioned structural formulae (3-1) to (3-4) are linearly bonded. In addition Q may bind to a silicon atom via a linking group having two or more valences, may be a hydrophilic segment which contains one or more hydrophilic units, and may have a branched unit selected from groups represented by the following structural formulae (3-5) to (3-7).

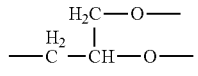

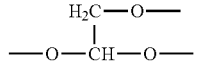

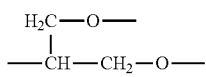 (3-7)

The linking group having two or more valences is the binding moiety to the silicon atom contained in the hydrophilic group of Q, and the structure thereof is not particularly restricted. As examples of the aforementioned linking groups, mention may be made of alkylene groups such as an ethylene group, a propylene group, a butylene group, a hexylene group and the like; alkylenephenylene groups such as an ethylenephenylene group, a propylenephenylene group and the like; alkylenearalkylene groups such as an ethylenebenzylene group and the like; alkylenoxyphenylene groups such as an ethyleneoxyphenylene group, a propyleneoxyphenylene group and the like; and alkylenoxybenzylene groups such as a methyleneoxybenzylene group, an ethyleneoxybenzylene group, a propyleneoxybenzylene group and the like. Furthermore, the following groups shown below may be mentioned. The number of the ether bonds in the linking group having two or more valences preferably ranges from 0 to 3 and is more preferably 0 or 1.

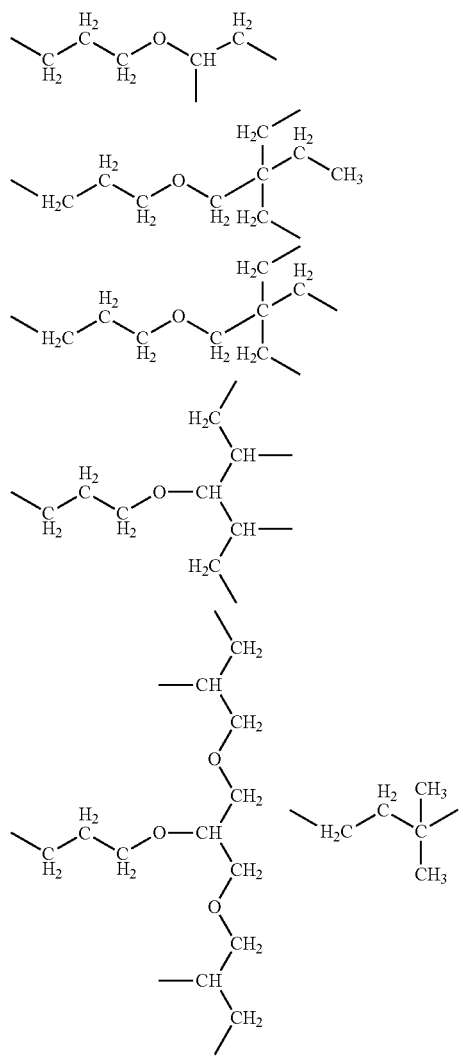

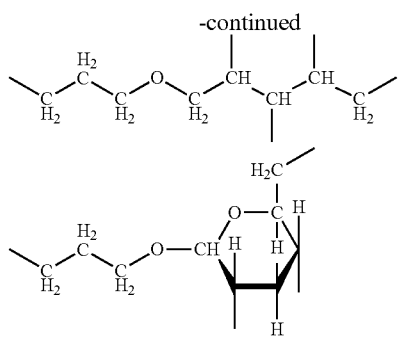

Q is more preferably a hydrophilic group represented by the following general formula (4-1), (4-2), (4-3) or (4-4)

General formula (4-1):

$$—R^4(—O—X^1{}_m—R^5)_p \qquad (4\text{-}1)$$

wherein $R^4$ is an organic group with (p+1) valence; and p is an integer ranging from 1 to 3. As the aforementioned $R^4$, the same groups as the aforementioned linking groups having two or more valences may be mentioned.

In particular, p is preferably 1 and $R^4$ is preferably a group selected from divalent organic groups represented by the following general formulae:

 (5-1)

 (5-1-2)

 (5-1-3)

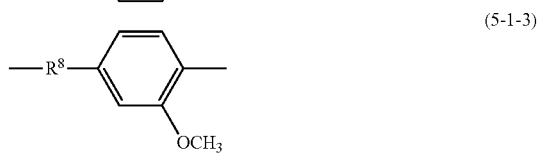 (5-2)

wherein each $R^8$ independently represents a substituted or non-substituted, and linear or branched, alkylene or alkenylene group having 2 to 22 carbon atoms or an arylene group having 6 to 22 carbon atoms.

$X^1$ is independently at least one hydrophilic unit selected from hydrophilic units represented by the aforementioned general formulae (3-1) to (3-4); and m is a number ranging from 1 to 100. When $X^1$ is a hydrophilic unit (alkyleneoxy group) represented by the aforementioned general formula (3-1), m is preferably a number ranging from 4 to 50, and the structure represented by "—$X^1{}_m$—" is, in particular, preferably the polyoxyalkylene unit represented by the aforementioned formula (3-1-1). When $X^1$ contains a hydrophilic unit represented by any of the aforementioned general formulae (3-2) to (3-4), m is a number preferably ranging from 1 to 50, and more preferably ranging from 1 to 15. $R^5$ is a hydrogen atom or a group selected from the group consisting of an alkyl group having 1 to 20 carbon atoms, an acyl group and a glycidyl group, and is preferably a hydrogen atom or a methyl group.

General formula (4-2):

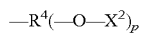 (4-2)

wherein $R^4$ is the same group as defined above;
p is the same number as defined above; and
$X^2$ is a hydrophilic group represented by the following structural formula (4-2-1):

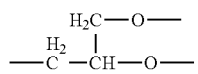 (4-2-1)

wherein at least one hydrophilic unit selected from the hydrophilic units represented by the aforementioned structural formulae (3-1) to (3-4) independently binds to each of the two oxygen atoms. The aforementioned hydrophilic unit may bind to a branched unit selected from the groups represented by any of the aforementioned structural formulae (3-5) to (3-7), and may form a dendritic polyether structure, polyglycerol structure or polyglycidyl ether structure in which hydrophilic units are branched in a multiple generation manner.

In the case of having no other branched units, as examples of the hydrophilic group represented by the aforementioned general formula (4-2), mention may be made of hydrophilic groups represented by the following general formula (4-2-2):

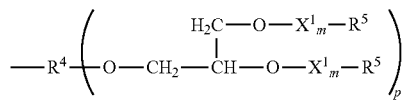 (4-2-2)

wherein p, $R^4$, $X^1$, $R^5$ and m are the same as defined above.
General formula (4-3):

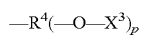 (4-3)

wherein $R^4$ is the same group as defined above;
p is the same number as defined above; and
$X^3$ is a hydrophilic group represented by the following structural formula (4-3-1):

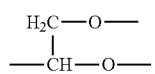 (4-3-1)

wherein at least one hydrophilic unit selected from the hydrophilic units represented by the aforementioned structural formulae (3-1) to (3-4) independently binds to each of the two oxygen atoms. The aforementioned hydrophilic unit may bind to a branched unit selected from the groups represented by any of the aforementioned structural formulae (3-5) to (3-7), and may form a dendritic polyether structure, polyglycerol structure or polyglycidyl ether structure in which hydrophilic units are branched in a multiple generation manner.

In the case of having no other branched units, as examples of the hydrophilic group represented by the aforementioned general formula (4-3), mention may be made of hydrophilic groups represented by the following general formula (4-3-2):

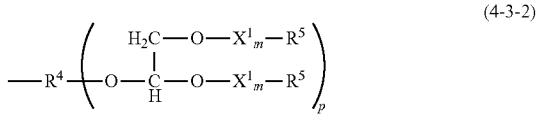 (4-3-2)

wherein p, $R^4$, $X^1$, $R^5$ and m are the same as defined above.
General formula (4-4):

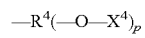 (4-4)

wherein $R^4$ is the same group as defined above;
p is the same number as defined above; and
$X^4$ is a hydrophilic group represented by the following structural formula (4-4-1):

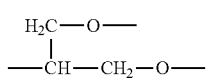 (4-4-1)

wherein at least one hydrophilic unit selected from the hydrophilic units represented by the aforementioned structural formulae (3-1) to (3-4) independently binds to each of the two oxygen atoms. The aforementioned hydrophilic unit may bind to a branched unit selected from the groups represented by any of the aforementioned structural formulae (3-5) to (3-7), and may form a dendritic polyether structure, polyglycerol structure or polyglycidyl ether structure in which hydrophilic units are branched in a multiple generation manner.

In the case of having no other branched units, as examples of the hydrophilic group represented by the aforementioned general formula (4-4), mention may be made of hydrophilic groups represented by the following general formula (4-4-2):

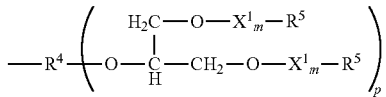 (4-4-2)

wherein p, $R^4$, $X^1$, $R^5$ and m are the same as defined above.
In the aforementioned general formula (1), each of a, b and c is independently a number having the following range: $1.0 \leq a \leq 2.5$, $0.0001 \leq b \leq 1.5$, and $0.0001 \leq c \leq 1.5$.

As preferable examples of the aforementioned co-modified organopolysiloxane, mention may be made of co-modified organopolysiloxanes represented by the following structural formula (1-1).
Structural formula (1-1):

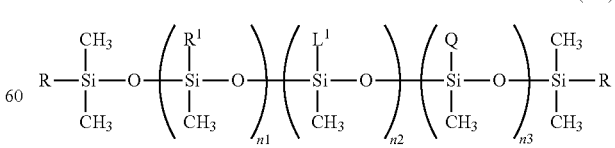 (1-1)

wherein $R^1$, $L^1$ and Q are the same groups as defined above;
R is a group selected from $R^1$, $L^1$ and Q, with the proviso that in the case of n2=0, at least one R is $L^1$, and in the case of n3=0, at least one R is Q. 90% by mole to 100% by mole of all $R^1$s is preferably a group selected from a methyl group, an ethyl group, and a phenyl group. In addition, for the purpose of designing a sophisticated co-modified organopolysiloxane, as a part of $R^1$, a long-chain alkyl group or a monovalent hydrocarbon group in which a part of the carbon-binding hydrogens is substituted by a halogen atom such as a fluorine atom or the like or the other organic group, can be selected, and is preferred. In addition, as a part of $R^1$, a hydrogen atom (—H) binding to a Si atom may be contained.

Each of n1, n2 and n3 is independently a number ranging from 0 to 2,000. n1 is a number preferably ranging from 10 to 2,000, more preferably ranging from 25 to 1,500, and furthermore preferably ranging from 50 to 1,000, n2 is a number preferably ranging from 0 to 250, and n3 is a number preferably ranging from 0 to 250, with the proviso that in the case of n2=0, at least one R is $L^1$, and in the case of n3=0, at least one R is Q. In addition, n1+n2+n3 is a number ranging from 1 to 2,000, preferably ranging from 10 to 2,000, more preferably ranging from 25 to 1,500, and furthermore preferably ranging from 50 to 1,000. In view of capability of imparting a smooth feeling on touch and a film thickness sensation to hair and durability of the aforementioned effects for a long time, an increased molecular weight is effective. For example, by use of a co-modified organopolysiloxane with an increased molecular weight, reduction of the effects during brushing or treating with a dryer does not occur much, and effects of preventing a frictional sensation or a sticky sensation after drying can be exhibited. In the case of using a co-modified organopolysiloxane having n1+n2+n3 ranging from 250 to 700, the most superior effects of improving the feeling on touch to hair both at the time of wetting and at the time of drying can be exhibited. This is particularly preferred.

As preferable examples of the aforementioned co-modified organopolysiloxanes, mention may be made of co-modified organopolysiloxanes represented by the following structural formula (1-1-1) or (1-1-2):

Structural formula (1-1-1):

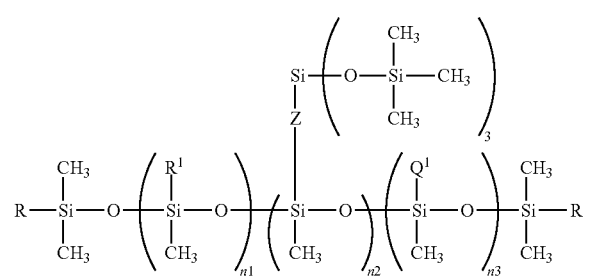

(1-1-1)

Structural formula (1-1-2):

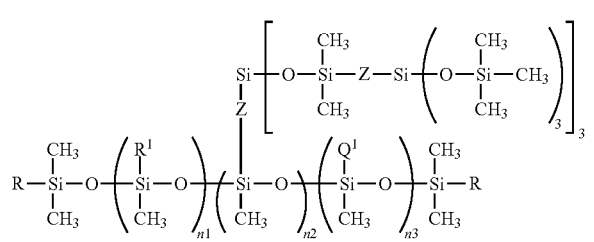

(1-1-2)

In the aforementioned structural formula (1-1-1) or (1-1-2), Z and $R^1$ are the same groups as defined above, and R is a group selected from $R^1$, the aforementioned $L^1$ and $Q^1$ described below. n1, n2 and n3 are the same as defined above. In the case of n2=0, at least one R is $L^1$. In addition, in the case of n3=0, at least one R is $Q^1$. Each $Q^1$ is independently a hydrophilic group selected from the group consisting of the following structural formulae (4-1-2), (4-2-2), (4-3-2), and (4-4-2). In the formulae, $R^4$, $X^1$ and $R^5$ are the same groups as defined above; and p and m are the same numbers as defined above.

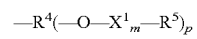 (4-1-2)

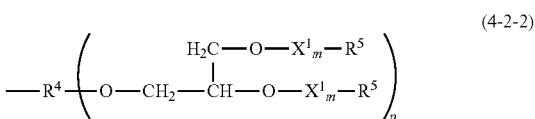 (4-2-2)

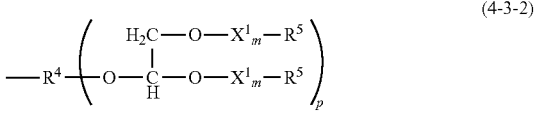 (4-3-2)

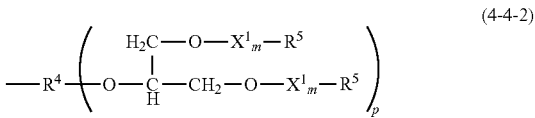 (4-4-2)

The aforementioned co-modified organopolysiloxane can be obtained by addition-reacting an organopolysiloxane having a reactive functional group with a compound having a siloxane dendron structure having a carbon-carbon double bond at one terminal of the molecular chain, and a hydrophilic compound having a reactive functional group. The addition reaction type is not particularly restricted. In view of reaction-controlling properties, purity, and yield, the addition reaction is preferably carried out in the presence of a hydrosilylation reaction catalyst.

For example, the aforementioned co-modified organopolysiloxane can be obtained by at least reacting (a) an organohydrogensiloxane represented by the following general formula (1'):

 (1')

$R^1_a H_{b+c} SiO_{(4-a-b-c)/2}$ wherein $R^1$, a, b and c are the same as defined above,
(b) a hydrophilic derivative having one reactive unsaturated group in one molecule and (c) a siloxane dendron compound having one reactive unsaturated group in one molecule.

The aforementioned co-modified organopolysiloxane can be more preferably produced by reacting together the aforementioned (b) hydrophilic derivative having one reactive unsaturated group in one molecule, the aforementioned (c) siloxane dendron compound having one reactive unsaturated group in one molecule, and the aforementioned (a) organohydrogensiloxane represented by the following general formula (1') under the condition of at least coexistence of the aforementioned components (b) and (c). Under the condition of non-coexistence of the aforementioned components (b) and (c), and namely under the condition in that the aforementioned component (c) is previously reacted alone with the organohydrogenpolysiloxane, followed by reacting with the aforementioned component (b), the ratio of an organopolysiloxane modified with only a group having the siloxane dendron structure is increased, and the modified organopolysiloxane exhibits poor miscibility with the surplus component (b) (more particular, polyglycerol monoallyl ether and the like). Thereby, phase separation may occur. As a result, a compound having an average compositional formula as originally designed at the time of introducing the functional groups with respect to the content of the silicon-binding hydrogen atoms may not be obtained in some cases. On the other hand, in the case of previously reacting only the aforementioned component (b) with the organohydrogenpolysiloxane, the concentration of the hydrophilic group, and in particular, the polyhydric group such as polyglycerol or the like, with respect to the concentration of the Si—H group in the reaction system is relatively increased, as compared with the concentration of the unsaturated group. Thereby, the reaction system may be gelled, for example in a dehydrogenation reaction or the like.

As the aforementioned organohydrogensiloxane (a) represented by the aforementioned general formula (1'), mention may be made of organohydrogensiloxanes represented by the following structural formula (1-1)'.

Structural formula (1-1)':

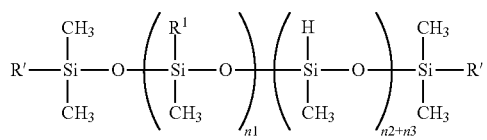

wherein each $R^1$ is independently the same group as defined above;

R' is a group selected from $R^1$ and a hydrogen atom;

n1, n2 and n3 are the same as defined above, with the proviso that in the case of n2+n3=0, both R's represent a hydrogen atom.

The aforementioned hydrophilic derivative (b) having one reactive unsaturated group in one molecule is a hydrophilic compound having a reactive functional group such as an alkenyl group at the terminal of the molecular chain such as an allyl polyether, an allyl polyglycerol, an allyl polyglycidyl ether, a polyglyceryl eugenol, and a glycerol monoallyl ether. The aforementioned hydrophilic derivative (b) can be synthesized in accordance with a conventional method and some of these are commercially available.

The aforementioned siloxane dendron compound (c) having one reactive unsaturated group in one molecule is more particularly, a compound having a siloxane dendron structure and one carbon-carbon double bond at the terminal of the molecular chain, represented by the following general formula (2'):

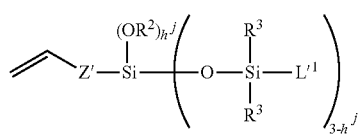

wherein $L'^1$ represents a methyl group or a silylalkyl group represented by the following general formula (2"), in the case of j=1;

Z' represents a divalent organic group.

General formula (2"):

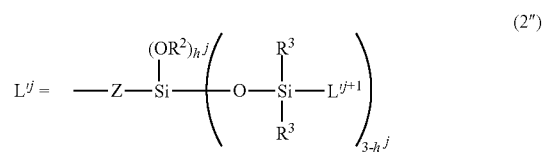

wherein $R^2$ is the same as defined above; $R^3$ is an alkyl group having 1 to 6 carbon atoms or a phenyl group; Z is a divalent organic group; j specifies the number of generations of the aforementioned silylalkyl group, represented by $L^j$, in the case in which the number of generations of the aforementioned silylalkyl group, which is the number of repetitions of the aforementioned silylalkyl group, is k', j is an integer ranging from 1 to k', and the number of generations k' is an integer ranging from 1 to 10; $L^{j+1}$ is the aforementioned silylalkyl group in the case of j<k', and $L^{j+1}$ is $R^3$ in the case of j=k'; and $h^j$ is a number ranging from 0 to 3.

The hydrosilylation reaction is preferably carried out in the presence of a catalyst. As examples of the catalyst, mention may be made of a compound such as platinum, ruthenium, rhodium, palladium, osmium, iridium or the like. A platinum compound is, in particular, effective since the catalytic activity thereof is high. As examples of platinum compounds, mention may be made of chloroplatinic acid; platinum metal; a platinum metal-supported carrier such as platinum-supported alumina, platinum-supported silica, platinum-supported carbon black or the like; and a platinum complex such as platinum-vinylsiloxane complex, platinum phosphine complex, platinum-phosphite complex, platinum alcholate catalyst or the like. The usage amount of the catalyst may range from about 0.5 to 100 ppm as a platinum metal in the case of using a platinum catalyst.

A crude product of the co-modified organopolysiloxane obtained by the aforementioned addition reaction can be purified by deodoration due to the hydrogenation treatment in a solvent or without a solvent in the presence of a hydrogenation catalyst. The aforementioned purified product can be preferably used in a cosmetic in which reduction of odor and miscibility with other cosmetic components are desired. In addition, as the pre-step or post-step of the aforementioned deodoration, a stripping treatment in which light products are removed by distillation by contacting a nitrogen gas with respect to a crude product or a hydrogenated product of a co-modified organopolysiloxane can be preferably carried out.

In the aforementioned hydrogenation treatment and stripping treatment, solvents, reaction conditions, pressure-reduction conditions and the like used in purification of conventional organopolysiloxane copolymers or polyether-modified silicones can be applied and selected without any restrictions.

Alternatively, the odor of the crude product of the co-modified organopolysiloxane obtained by the aforementioned addition reaction can also be easily reduced by carrying out a stripping step in which light products are removed by distillation by contacting a nitrogen gas after an unreacted unsaturated product is hydrolyzed by adding an acid substance.

The co-modified organopolysiloxanes obtained by the aforementioned preparation method can be easily produced and the modification index thereof or types of modified groups can be easily controlled by only changing charged amounts of the raw materials. For this reason, it is easy to design functional molecules. In addition, the obtained co-modified organopolysiloxanes have advantages in that separation into two phases or sedimentation of unreacted raw materials after production hardly occurs, they are chemically stable and superior practical use is exhibited.

The aforementioned co-modified organopolysiloxane (hereinafter, referred to as "(A) co-modified organopolysiloxane") possesses both a specified hydrophilic group and a siloxane dendron structure-containing group, and can provide, as an oil agent component of a cosmetic for hair of the present invention, smooth combability with fingers without a frictional sensation during wetting and during drying to the hair. Furthermore, superior foaming properties and a superior feeling on touch of foam are exhibited, smooth combability with a comb or fingers during drying and a moisturizing feeling on touch are exhibited without an uncomfortable sticky sensation, and a flexible styling sensation can be provided to the hair. In addition, superior durability can be provided. Furthermore, since the aforementioned (A) co-modified organopolysiloxane possesses superior miscibility with each component in the cosmetic for hair, increased stability can be provided to the cosmetic for hair of the present invention.

The blending amount of the aforementioned (A) co-modified organopolysiloxane contained in the cosmetic for hair of the present invention is not particularly restricted, and for example, can range from 0.0001 to 20% by weight (mass), can preferably range from 0.001 to 10% by weight (mass) and in particular, can preferably range from 0.01 to 5% by weight (mass).

The cosmetic for hair of the present invention can be appropriately prepared by mixing the aforementioned (A) co-modified organopolysiloxane with various conventional components known in the field of cosmetics. Hereinafter, various conventional components are described in detail.

Oil Agent

The cosmetic for hair of the present invention preferably comprises (B) an oil agent. Use of the aforementioned (A) co-modified organopolysiloxane together with the aforementioned (B) oil agent can achieve, for example, improvements of a feeling on touch which can be difficulty achieved by using a conventional polyglycerol-modified silicone with an oil agent. The "oil agent" in the present invention is generally used as a component of a cosmetic, and is not particularly restricted. The aforementioned (B) oil agent is usually in the form of a liquid at 5° C. to 100° C., and may be in the form of a solid such as a wax or in the form of a gum or a paste which has an increased viscosity and is thickened, as described below. The aforementioned (B) oil agent can be used as a single type thereof or in combination with two or more types thereof, in accordance with the purpose thereof.

The aforementioned (B) oil agent is preferably at least one type selected from (B1) a silicone-based oil agent and (B2) a non-silicone-based oil agent selected from organic oils. The types, viscosities and the like of the aforementioned oil agents can be appropriately selected in accordance with types and usages of cosmetics for hair.

The aforementioned (B1) silicone-based oil agent is generally hydrophobic, and the molecular structure thereof may be a cyclic, linear or branched structure. The functional groups of the silicone-based oils are generally a methyl group or a hydroxyl group. An organo-modified silicone in which a part or all of the aforementioned functional groups is/are substituted with functional groups may be used. The aforementioned organo-modified silicone is an organo-modified silicone other than the aforementioned (A) co-modified organopolysiloxane, and is a component to be blended in a cosmetic for hair. The organo-modified silicone may have an alkylene chain, an aminoalkylene chain or a polyether chain in addition to the polysiloxane bond as a main chain, and may comprise a so-called block copolymer. In addition, the aforementioned organo-modified group may be present at one or both of the terminals of the side chain of the polysiloxane chain. More particularly, as examples thereof, mention may be made of amino-modified silicones, aminopolyether-modified silicones, epoxy-modified silicones, carboxyl-modified silicones, amino acid-modified silicones, acryl-modified silicones, phenol-modified silicones, amidoalkyl-modified silicones, polyamide-modified silicones, aminoglycol-modified silicones, alkoxy-modified silicones, C8-30 higher alkyl-modified silicones, and alkyl-modified silicone resins.

As the linear organopolysiloxanes, organopolysiloxanes represented by the following general formula (5):

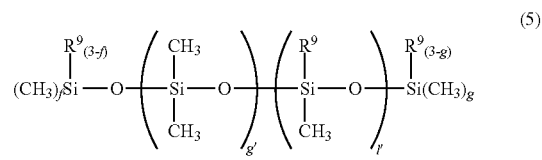

(5)

wherein $R^9$ is a hydrogen atom, or a group selected from a hydroxyl group, a substituted or non-substituted monovalent hydrocarbon group, an alkoxy group, a polyoxyalkylene group, and a polyorganosiloxane group; each of f and g independently represents an integer ranging from 0 to 3; g' is an integer ranging from 0 to 10,000; and l' is an integer ranging from 0 to 10,000, with the proviso that $1 \leq g'+l' \leq 10,000$, can be used. The viscosity of the linear organopolysiloxanes at 25° C. is not particularly restricted, and may usually range from 0.65 to 1,000,000 mm²/sec, which corresponds to the viscosity of so-called silicone oil. On the other hand, the organopolysiloxane may have an ultra high viscosity which corresponds to that of a silicone gum.

As examples of substituted or non-substituted monovalent hydrocarbon groups, mention may be made of linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cyclopentyl group, a cyclohexyl group and the like; aryl groups having 6 to 30 carbon atoms such as a phenyl group, a tolyl group, a xylyl group, a naphthyl group and the like; and substituted groups thereof, in which hydrogen atoms binding to carbon atoms of the aforementioned groups are at least partially substituted by a halogen atom such as a fluorine atom, or an organic group such as an epoxy group, an acyl group, a carboxyl group, an amino group, an amide group, a (meth)acryl group, a mercapto group, a carbinol group, a phenol group or the like. As examples of alkoxy groups, mention may be made of an alkoxy group having 1 to 30 carbon atoms such as a methoxy group, an ethoxy group, a propoxy group or the like.

As examples of silicone oils, mention may be made of, for example, a dimethylpolysiloxane in which both molecular terminals are capped with trimethylsiloxy groups (dimethylsilicone with a low viscosity such as 2 mPa·s or 6 mPa·s to dimethylsilicone with a high viscosity such as 1,000,000 mPa·s, and in addition, a dimethylsilicone with an ultra-high viscosity), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl(trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl(3,3,3-trifluoropropyl)siloxane and dimethylsiloxane in which both molecular terminals are capped with trimethylsiloxy groups, an α,ω-diethoxypolydimethylsiloxane, a higher alkoxy-modified silicone, a higher fatty acid-modified silicone, dimethiconol, a siloxane with a low molecular weight such as a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, or the like, a dimethylpolysiloxane in which both molecular terminals are capped with trimethylsilyl groups, an α,ω-dihydroxypolydimethylsiloxane, and the like.

In the cosmetic for hair of the present invention, a so-called silicone gum having 1,000,000 mm²/s or more, which has ultra-high viscosity but possesses fluidity, can also be preferably used as a silicone oil. The silicone gum is a linear diorganopolysiloxane having an ultra-high degree of polymerization, and is also referred to as a silicone raw rubber or an organopolysiloxane gum. The silicone gum possesses a high degree of polymerization, and for this reason, it has a measurable degree of plasticity. In view of this, the silicone gum is different from the aforementioned oil silicones. The aforementioned silicone gum can be blended in the cosmetic for hair according to the present invention as it is, or as a liquid gum dispersion (an oil dispersion of the silicone gum) in which the silicone gum is dispersed in an oil silicone.

As examples of the aforementioned silicone raw rubber, mention may be made of substituted or non-substituted organopolysiloxanes having a dialkylsiloxy unit (D unit) such as dimethylpolysiloxane, methylphenylpolysiloxane, aminoolysiloxane, methylfluoroalkyl polysiloxane and the like, or those having a slightly-crosslinking structure thereof and the like. As representative examples thereof, there are those represented by the following general formula:

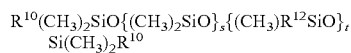

wherein $R^{12}$ is a group selected from a vinyl group, a phenyl group, an alkyl group having 6 to 20 carbon atoms, an aminoalkyl group having 3 to 15 carbon atoms, a perfluoroalkyl group having 3 to 15 carbon atoms, and a quaternary ammonium salt group-containing alkyl group having 3 to 15 carbon atoms; the terminal group $R^{10}$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms; s=2,000 to 6,000; t=0 to 1,000; and s+t=2,000 to 6,000. Among these, a dimethylpolysiloxane raw rubber having a degree of polymerization ranging from 3,000 to 20,000 is preferred. In addition, an amino-modified methylpolysiloxane raw rubber having a 3-aminopropyl group, an N-(2-aminoethyl)-3-aminopropyl group or the like on the side chain or the terminal of the molecule is preferred. In addition, in the present invention, the silicone gum can be used alone or in combination with two or more types thereof, as necessary.

The silicone gum has an ultra-high degree of polymerization. For this reason, the silicone gum can exhibit a superior retention property on hair or skin, and can form a protective film with a superior aeration property. For this reason, the silicone gum is a component which can particularly provide glossiness and luster on hair and can impart a texture with tension on the entire hair during use and after use.

The blending amount of the silicone gum may range from 0.05 to 30% by weight (mass) and may preferably range from 1 to 15% by weight (mass), with respect to the total amount of the cosmetic for hair. When the silicone gum is used as an emulsion composition prepared via a step of preliminarily emulsifying (including emulsion polymerization), the silicone gum can be easily blended, and can stably be blended in the cosmetic for hair of the present invention. If the blending amount of the silicone gum is below the aforementioned lower limit, an effect of imparting a specific feeling on touch or glossiness with respect to hair may be insufficient.

As cyclic organopolysiloxanes, for example, organopolysiloxanes represented by the following general formula (6):

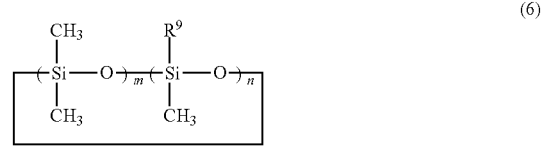

wherein
$R^9$ is the same as defined above;
m is an integer ranging from 0 to 8; and
n is an integer ranging from 0 to 8, with the proviso that 3≤m+n≤8,
can be used.

As examples of cyclic organopolysiloxanes, mention may be made of hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl) tetramethylcyclotetrasiloxane and the like.

As branched organopolysiloxanes, for example, organopolysiloxanes with a low molecular having volatility represented by the following general formula (7):

wherein
$R^9$ is the same as defined above;
p is an integer ranging from 1 to 4; and
q is an integer ranging from 0 to 500,
and so-called silicone resins in the form of a liquid, a solid or the like can be used.

As branched organopolysiloxanes, mention may be made of a siloxane with a low molecule such as methyltristrimethylsiloxysilane, ethyltristrimethylsiloxysilane, propyltristrimethylsiloxysilane, tetrakistrimethylsiloxysilane, phenyltristrimethylsiloxysilane or the like; or a silicone resin of a highly branched molecular structure, a net-like molecular structure or a cage-like molecular structure may be used. A silicone resin containing at least a monoorganosiloxy unit (T unit) and/or a siloxy unit (Q unit) is preferred. The aforementioned silicone resins having branched units possess a net-like structure. In the case of applying the silicone resins to hair or the like, a uniform film is formed and protective effects with respect to dryness and low temperature are provided. In addition, the silicone resins having branched units tightly adhere to hair or the like, and can provide glossiness and a transparent impression to hair or the like.

Hereinafter, a higher alkyl-modified silicone, an alkyl-modified silicone resin and a polyamide-modified silicone resin which are particularly preferred as the organo-modified silicones are described. The higher alkyl-modified silicone is in the form of a wax at room temperature, and is a component useful as a part of a base material of an oil-based solid cosmetic for hair. Therefore, the higher alkyl-modified silicones can be preferably used in the cosmetics for hair of the present invention. As examples of the aforementioned higher alkyl-modified silicone waxes, mention may be made of a methyl (long chain alkyl)polysiloxane having both molecular terminals capped with trimethylsiloxy groups, a copolymer of a dimethylpolysiloxane and a methyl(long chain alkyl)siloxane having both molecular terminals capped with trimethylsiloxy groups, a dimethylpolysiloxane modified with long chain alkyls at both terminals, and the like. As examples of commercially available products thereof, mention may be made of, AMS-C30 Cosmetic Wax, 2503 Cosmetic Wax and the like (manufactured by Dow Corning Corporation, in the USA).

The aforementioned (A) co-modified organopolysiloxane exhibits a superior dispersion property of a higher alkyl-modified silicone wax, and for this reason, a cosmetic for hair exhibiting superior storage stability for a long time can be obtained. In addition, a superior shaping property of the cosmetic for hair can also be exhibited. In particular, in a system containing powder(s), there is an advantage in that separation of the higher alkyl-modified silicone wax hardly occurs, and an oil-based cosmetic for hair which can exhibit superior shape-retaining strength and can be smoothly and uniformly spread during application can be provided.

In the cosmetic for hair of the present invention, the higher alkyl-modified silicone wax preferably has a melting point of 60° C. or higher in view of a cosmetic durability effect and stability at increased temperatures.

The alkyl-modified silicone resin is a component for imparting sebum durability, a moisture-retaining property, and a fine texture feeling on touch to the cosmetic for hair, and one in the form of a wax at room temperature can be preferably used. For example, a silsesquioxane resin wax described in Published Japanese Translation No. 2007-532754 of the PCT International Application may be mentioned. As commercially available products thereof, SW-8005 C30 RESIN WAX (manufactured by Dow Corning Corporation in the USA) and the like may be mentioned.

The aforementioned (A) co-modified organopolysiloxane can uniformly disperse the alkyl-modified silicone resin wax in the cosmetic for hair, in the same manner as described for the higher alkyl-modified silicone wax. In addition, an oil phase containing the aforementioned alkyl-modified silicone resin wax can be stably emulsified optionally together with the other surfactant. A conditioning effect with respect to hair can be improved and a fine texture and a moisturized feeling on touch can be imparted.

As examples of polyamide-modified silicones, mention may be made of, for example, siloxane-based polyamide compounds described in U.S. Pat. No. 5,981,680 (Japanese Unexamined Patent Application, First Publication No. 2000-038450) and Published Japanese Translation No. 2001-512164 of the PCT International Application. As examples of commercially available products, mention may be made of 2-8178 Gellant, 2-8179 Gellant and the like (manufactured by Dow Corning Corporation, in the USA). The aforementioned polyamide-modified silicones are also useful as an oil-based raw material, and in particular, a thickening/gelling agent of a silicone oil.

In the case of using the polyamide-modified silicone together with the aforementioned (A) co-modified organopolysiloxane, the cosmetic for hair of the present invention can exhibit a good spreading property, a good styling property, a superior stable sensation and a superior adhesive property in the case of applying to hair or the like. In addition, there are advantages in view of qualities in that a glossy transparent sensation and superior glossiness can be provided, the viscosity or hardness (flexibility) of the whole cosmetic for hair containing oil-based raw material(s) can be appropriately adjusted, and an oily sensation (oily and sticky feeling on touch) can be totally controlled. In addition, by use of the aforementioned (A) co-modified organopolysiloxane, dispersion stability of perfume(s), powder(s) and the like can be improved. For this reason, for example, there is a characteristic in that a uniform and fine cosmetic sensation can be maintained for a long time.

As the aforementioned (B2) organic oil agent, (B2-1) a higher alcohol, (B2-2) a hydrocarbon oil, (B2-3) a fatty acid ester oil, and (B2-4) a higher fatty acid, fats and oils, or a fluorine-based oil agent are representative. In the present invention, the aforementioned (B2) organic oil agent is not particularly restricted, but a higher alcohol, a hydrocarbon oil, a fatty acid ester oil and a higher fatty acid are preferred. The aforementioned oil agents can exhibit superior miscibility and dispersibility with respect to the aforementioned (A) co-modified organopolysiloxane. For this reason, they can be stably blended in a cosmetic composition for hair of the present invention, and they can supplement effects of the aforementioned (A) co-modified organopolysiloxane and strengthen the inherent effects of each of the aforementioned components (A) and (B2).

The aforementioned (B2-1) higher alcohol is, for example, a higher alcohol having 10 to 30 carbon atoms. The aforementioned higher alcohol is a saturated or unsaturated monovalent aliphatic alcohol, and the moiety of the hydrocarbon group thereof may be linear or branched, but a linear one is preferred. As examples of higher alcohols having 10 to 30 carbon atoms, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol and the like. In the present invention, use of a higher alcohol having a melting point ranging from 40 to 80° C. or use of a combination of plural higher alcohols so as to have a melting point thereof ranging from 40 to 70° C. is preferred. The aforementioned higher alcohols can form an aggregate which is a so-called alpha gel, together with a surfactant. Thereby, the higher alcohols may possess a function of increasing viscosity of a preparation, and stabilize an emulsion. For this reason, they are, in particular, useful as a base agent of a cosmetic for hair.

As examples of the aforementioned (B2-2) hydrocarbon oils, mention may be made of liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene and the like.

As examples of the aforementioned (B2-3) fatty acid ester oils, mention may be made of hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-hexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptyllundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptyllundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptyllundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like. Lanolin and lanolin derivatives can also be used as the fatty acid ester oils.

As examples of the aforementioned (B2-4) higher fatty acids, mention may be made of, for example, lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As the aforementioned (B) oil agent, a silicone-based oil agent and a non-silicone-based oil agent may be used in combination. By use of the combination, in addition to a refreshing feeling on touch which the silicone oils inherently possess, the moisture of hair can be maintained and a moisturizing sensation such that hair is moisturized (also referred to as a moisturizing feeling on touch) or a smooth feeling on touch can be provided to the cosmetics for hair of the present invention. In addition, an advantage in that stability of the cosmetics over time is not impaired can be obtained. Furthermore, by a cosmetic comprising a hydrocarbon oil and/or a fatty acid ester oil and a silicone oil, the aforementioned moisturizing components (namely, the hydrocarbon oils and/or fatty acid ester oils) can be stably and uniformly applied on skin or hair. For this reason, effects of retaining moisture on the skin of the moisturizing components are improved. Therefore, a cosmetic comprising both a non-silicone-based oil agent and a silicone-based oil agent has an advantage in that a smoother and moisturizing feeling on touch can be provided, as compared with a cosmetic comprising only a non-silicone-based oil agent (such as a hydrocarbon oil, a fatty acid ester oil or the like).

In the present invention, in addition to the aforementioned oil agents, fats and oils, higher fatty acids, fluorine-based oils and the like may be used as the aforementioned (B) oil agent, and they may be used in combination of two or more types thereof. In particular, fats and oils derived from vegetables provide a healthy image derived from natural products and exhibit a superior moisture-retaining property and superior compatibility with hair. For this reason, they are preferably used in a cosmetic for hair of the present invention.

As examples of natural animal or vegetable fats and oils and semi-synthetic fats and oils, mention may be made of avocado oil, linseed oil, almond oil, ibota wax, perilla oil, olive oil, cacao butter, kapok wax, kaya oil, carnauba wax, liver oil, candelilla wax, beef tallow, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, olive oil, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, POE cholesterol ether, monostearyl glycerol ether (batyl alcohol), monooleyl glycerol ether (selachyl alcohol), egg yolk oil and the like, with the proviso that POE means polyoxyethylene.

As examples of fluorine-based oils, mention may be made of perfluoro polyether, perfluorodecalin, perfluorooctane and the like.

The blending amount of the aforementioned (B) oil agent in the cosmetic for hair of the present invention is not particularly restricted, and preferably ranges from 0.1 to 90% by weight (mass), more preferably ranges from 0.5 to 70% by weight (mass), furthermore preferably ranges from 1 to 50% by weight (mass), and in particular, preferably ranges from 5 to 25% by weight (mass).

In addition, the blending ratio between the aforementioned (B) oil agent and (A) co-modified organopolysiloxane, namely the weight ratio of (B)/(A) preferably ranges from 0.01 to 100 and more preferably ranges from 0.1 to 50. If the blending amount of the aforementioned component (B) is increased too much, effects of the aforementioned component (A) may be reduced.

Surfactants

The cosmetic for hair of the present invention preferably comprises (C) a surfactant.

Types of the aforementioned (C) surfactants are not particularly restricted, and can be at least one type selected from the group consisting of (C1) anionic surfactants, (C2) cationic surfactants, (C3) nonionic surfactants, (C4) amphoteric surfactants and (C5) semi-polar surfactants.

As examples of the aforementioned (C1) anionic surfactants, mention may be made of saturated or unsaturated fatty acid salts such as sodium laurate, sodium stearate, sodium oleate, sodium linoleate and the like; alkylsulfuric acid salts; alkylbenzenesulfonic acids such as hexylbenzenesulfonic acid, octylbenzenesulfonic acid, dodecylbenzenesulfonic acid and the like, as well as salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamidesulfuric acid salts; alkyl- or alkenylphosphoric acid salts; alkylamidephosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. As examples of salts, mention may be made of alkali metal salts such as a sodium salt and the like, alkaline earth metal salts such as a magnesium salt and the like, alkanolamine salts such as a triethanolamine salt and the like, and an ammonium salt.

As examples of the aforementioned (C2) cationic surfactants, mention may be made of alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE) oleylmethylammonium (2EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, stearic acid diethylaminoethylamide, stearic dimethylaminopropylamide, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

As examples of the aforementioned (C3) nonionic surfactants, mention may be made of polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylene glycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. A polyoxyalkylene-modified silicone, a polyglycerol-modified silicone, or a glycerol-modified silicone in which an alkyl branch, a linear silicone branch, a siloxane dendrimer branch or the like may be possessed together with a hydrophilic group at the same time, if necessary, can also be preferably used.

The organo-modified silicone already described as the aforementioned (B) oil agent may possess an aspect as a nonionic emulsifier depending on the structure thereof, in addition to an aspect as an oil agent. Namely, the organo-modified silicone oils such as a polyoxyalkylene-modified silicone, a polyglycerol-modified silicone, a glycerol-modified silicone and the like, possessing both a hydrophilic moiety and a hydrophobic moiety in a molecule possess a function as a nonionic surfactant. In addition, the aforementioned (A) co-modified organopolysiloxane, per se, possesses the aforementioned function. They may function as an auxiliary agent for improving stability of the aforementioned (C3) nonionic surfactant and may improve stability of the entire preparation. Therefore, they can be used in combination.

As examples of the aforementioned (C4) amphoteric surfactants, mention may be made of imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. More particularly, as examples thereof, mention may be made of imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt and the like; alkylbetaine-type amphoteric surfactants such as lauryl dimethylaminoacetic acid betaine, myristyl betaine and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine and the like.

As examples of the aforementioned (C5) semi-polar surfactants, mention may be made of alkylamine oxide-type surfactants, alkylamine oxides, alkylamide amine oxides, alkylhydroxyamine oxides and the like. Alkyldimethylamine oxides having 10 to 18 carbon atoms, alkoxyethyl dihydroxyethylamine oxides having 8 to 18 carbon atoms and the like are preferably used. More particularly, as examples thereof, mention may be made of dodecyldimethylamine oxide, dimethyloctylamine oxide, diethyldecylamine oxide, bis-(2-hydroxyethyl) dodecylamine oxide, dipropyltetradecylamine oxide, methylethylhexadecylamine oxide, dodecylamidopropyl dimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The blending amount of the aforementioned (C) surfactants in the cosmetic for hair of the present invention is not particularly restricted. In order to improve a cleansing property, the surfactants can be blended in an amount ranging from 0.1 to 90% by weight (mass) and preferably ranging from 1 to 50% by weight (mass) in the total amount of the cosmetic composition. In view of a cleansing property, the amount is preferably 25% by weight (mass) or more.

Water-soluble Polymers

The cosmetic for hair of the present invention preferably comprises (D) a water-soluble polymer. The aforementioned (D) water-soluble polymer may be blended in order to prepare a cosmetic for hair in the desirable form, and improve a sensation during use of the cosmetic for hair such as a feeling on touch with respect to hair or the like, a conditioning effect or the like.

As the aforementioned (D) water-soluble polymer, any one of amphoteric, cationic, anionic, nonionic, and water-swellable clay minerals can be used as long as they are commonly used in a cosmetic for hair. One type or two or more types of water-soluble polymers can be used. The aforementioned (D) water-soluble polymers have an effect of thickening a hydrous component, and for this reason, they are useful in the case of obtaining a hydrous cosmetic for hair, and in particular, in the form of a gel hydrous cosmetic for hair, a water-in-oil emulsion cosmetic for hair, and an oil-in-water emulsion cosmetic for hair.

As examples of natural water-soluble polymers, mention may be made of vegetable-based polymers such as gum Arabic, tragacanth gum, galactan, guar gum, carob gum, karaya gum, carrageenan, pectin, agar, quince seed, algal colloid, starch (rice, corn, potato, or wheat), glycyrrhizinic acid and the like; microorganism-based polymers such as xanthan gum, dextran, succinoglucan, pullulan, and the like; and animal-based polymers such as collagen, casein, albumin, gelatin, and the like. In addition, as examples of semi-synthetic water-soluble polymers, mention may be made of, for example, starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate and the like. As examples of synthetic water-soluble polymers, mention may be made of, for example, vinyl-based polymers such as polyvinyl alcohol, polyvinyl methyl ether-based polymer, polyvinylpyrrolidone, carboxyvinyl polymer (CARBOPOL 940, CARBOPOL 941; manufactured by The Lubrizol Corporation); polyoxyethylene-based polymers such as polyethylene glycol 20,000, polyethylene glycol 6,000, polyethylene glycol 4,000 and the like; copolymer-based polymers such as a copolymer of polyoxyethylene and polyoxypropylene, PEG/PPG methyl ether and the like;

acryl-based polymers such as poly(sodium acrylate), poly (ethyl acrylate), polyacrylamide and the like; polyethylene imines; cationic polymers and the like. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride. They may be any one of natural ones and synthesized ones.

As examples of components which can be preferably blended in a cosmetic for hair, mention may be made of, in particular, (D1) cationic water-soluble polymers. As examples of the aforementioned (D1) cationic water-soluble polymers, mention may be made of quaternary nitrogen-modified polysaccharides such as cation-modified cellulose, cation-modified hydroxyethylcellulose, cation-modified guar gum, cation-modified locust bean gum, cation-modified starch and the like; dimethyldiallylammonium chloride derivatives such as a copolymer of dimethyldiallylammonium chloride and acrylamide, poly(dimethylmethylene piperidinium chloride) and the like; vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride and the like; and methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, methacryloylethyl trimethylammonium chloride and methoxy polyethylene glycol methacrylate, and the like.

In addition, in particular, as a component which can be preferably blended in a cosmetic for hair, (D2) an amphoteric water-soluble polymer can be mentioned. More particularly, as examples thereof, mention may be made of amphoterized starches; dimethyldiallylammonium chloride derivatives such as a copolymer of acrylamide, acrylic acid, and dimethyldiallylammonium chloride, and a copolymer of acrylic acid and dimethyldiallylammonium chloride; and methacrylic acid derivatives such as polymethacryloylethyl dimethylbetaine, a copolymer of methacryloyloxyethyl carboxybetaine and alkyl methacrylate, a copolymer of octylacrylamide, hydroxypropyl acrylate and butylaminoethyl methacrylate, and a copolymer of N-methacryloyloxyethyl-N,N-dimethylammonium α-methylcarboxybetaine and alkyl methacrylate.

The blending amount of the aforementioned (D) water-soluble polymer in the cosmetic for hair of the present invention can be suitably selected in accordance with the type and purpose of the cosmetic for hair. The amount may preferably range from 0.01 to 5.0% by weight (mass) and more preferably range from 0.1 to 3.0% by weight (mass) with respect to the total amount of the cosmetic for hair in order to particularly obtain a superior sensation during use. If the blending amount of the water-soluble polymer exceeds the aforementioned upper limit, a rough feeling with respect to the hair may remain in some types of the cosmetics for hair. On the other hand, if the blending amount is below the aforementioned lower limit, advantageous technical effects such as a thickening effect, a conditioning effect and the like may not be sufficiently exhibited.

Alcohols

The cosmetic for hair of the present invention preferably comprises (E) an alcohol. As the aforementioned (E) alcohols, one or more types of polyhydric alcohols and/or a monovalent lower alcohols can be used. As examples of lower alcohols, mention may be made of ethanol, isopropanol, n-propanol, t-butanol, s-butanol and the like. As examples of polyhydric alcohols, mention may be made of divalent alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol and the like; trivalent alcohols such as glycerol, trimethylol propane, 1,2,6-hexanetriol and the like; polyhydric alcohols having 4 or more valences such as pentaerythritol, xylitol and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol and the like. In addition to the aforementioned low-molecule polyhydric alcohols, polyhydric alcohol polymers such as diethylene glycol, dipropylene glycol, triethylene glycol, propylene glycol, tetraethylene glycol, diglycerol, polyethylene glycol, triglycerol, tetraglycerol, polyglycerol and the like may be mentioned. Among these, 1,3-propanediol, 1,3-butylene glycol, sorbitol, dipropylene glycol, glycerol, and polyethylene glycol are, in particular, preferred.

The blending amount of the aforementioned (E) alcohols preferably ranges from 0.1 to 50% by weight (mass) with respect to the total amount of the cosmetic for hair. Alcohols can be blended in an amount ranging from about 5 to 30% by weight (mass) with respect to the total amount of the cosmetic for hair in order to improve storage stability of the cosmetic for hair. This is one preferable mode for carrying out the present invention.

Thickening Agents and/or Gelling Agents

The cosmetic for hair of the present invention preferably further comprises (F) a thickening agent and/or a gelling agent. As an aqueous thickening and/or gelling agent, the aforementioned water-soluble polymers of component (D) described above are preferably used. In addition, as examples of oil-soluble thickening and/or gelling agents, mention may be made of metallic soaps such as aluminum stearate, magnesium stearate, zinc myristate and the like; amino acid derivatives such as N-lauroyl-L-glutamic acid, α,γ-di-n-butylamine and the like; dextrin fatty acid esters such as dextrin palmitate, dextrin stearate, dextrin 2-ethylhexanoate palmitate and the like; sucrose fatty acid esters such as sucrose palmitate, sucrose stearate and the like; benzylidene derivatives of sorbitol such as monobenzylidene sorbitol, dibenzylidene sorbitol and the like; and the like. The thickening and/or gelling agents can be used alone or in combination of two or more types thereof, if necessary.

As the aforementioned (F) thickening and/or gelling agent, an organo-modified clay mineral can be used. The organo-modified clay mineral can be used as a gelling agent for the oil agent(s) in the same manner as described in the aforementioned oil-soluble thickening and/or gelling agent. As examples of organo-modified clay minerals, mention may be made of, for example, dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate and the like. As examples of commercially available products thereof, mention may be made of Benton 27 (benzyldimethylstearylammonium chloride-treated hectorite, manufactured by Nationalred Co.), Benton 38 (distearyldimethylammonium chloride-treated hectorite, manufactured by Nationalred Co.) and the like.

The usage amount of the aforementioned (F) thickening and/or gelling agent in the cosmetic for hair of the present invention is not particularly restricted, and may preferably range from 0.5 to 50 parts by weight (mass), and more preferably range from 1 to 30 parts by weight (mass), with respect to 100 parts by weight (mass) of the oil agent(s). The ratio thereof in the cosmetic for hair preferably ranges from 0.01 to 30% by weight (mass), more preferably ranges from 0.1 to 20% by weight (mass), and furthermore preferably ranges from 1 to 10% by weight (mass).

By thickening or gelling the oil agent(s) in the cosmetic for hair of the present invention, the viscosity or hardness of the cosmetic can be made appropriate, and the outer appearance, blending properties, and a sensation during use can be improved. In addition, a desirable formulation and/or a desirable form of the cosmetic can be achieved. The aforementioned (A) co-modified organopolysiloxane may also possess a function as a thickening and/or gelling agent. When the other (F) thickening and/or gelling agent is used, in addition thereto, there are advantages in view of qualities in that an oily sensation (oily and sticky feeling on touch) can be further totally controlled, and a hair-retaining property can be further improved.

Powder

The cosmetic for hair of the present invention can further comprise (G) powder. "Powder" in the present invention is that commonly used as a component of a cosmetic, and includes white and colored pigments and extender pigments. The white and colored pigments are used in coloring a cosmetic, and on the other hand, the extender pigments are used in improvement in a feeling on touch of a cosmetic and the like. As the aforementioned (G) powder in the present invention, white or colored pigments and extender pigments which are commonly used in cosmetics can be used without any restrictions. One type of powder may be used, or two or more types of powders may be preferably blended.

With respect to the aforementioned (G) powders, there is no restriction on the form thereof (sphere, bar, needle, plate, amorphous, spindle or the like), the particle size (aerosol, microparticle, pigment-grade particle, or the like), and the particle structure (porous, non-porous or the like) thereof. The average primary particle size of the powders preferably ranges from 1 nm to 100 μm.

As examples of the aforementioned (G) powders, mention may be made of, for example, inorganic powders, organic powders, surfactant metal salt powders (metallic soaps), colored pigments, pearl pigments, metal powder pigments and the like. In addition, hybrid products of the aforementioned pigments can also be used.

More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like.

As examples of organic powders, mention may be made of polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine and the like.

As examples of surfactant metal salt powders, mention may be made of zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like.

As examples of colored pigments, mention may be made of inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, laked pigments of natural pigments such as carminic acid, laccaic acid, carthamin, brazilin, crocin and the like.

As examples of pearl pigments, mention may be made of titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like.

As examples of metal powder pigments, mention may be made of powders of metals such as aluminum, gold, silver, copper, platinum, stainless steel, and the like.

In addition, in the aforementioned (G) powders, a part or all parts thereof may, in particular, preferably be subjected to a surface treatment such as a water-repellent treatment, a hydrophilic treatment or the like. In addition, composited products in which the aforementioned powders are mutually composited may be used. In addition, surface-treated products in which the aforementioned powders have been subjected to a surface treatment with a general oil agent, a silicone compound other than the aforementioned (A) co-modified organopolysiloxane of the present invention, a fluorine compound, a surfactant, a thickening agent or the like can also be used. One type thereof or two or more types thereof can be used, as necessary.

The water-repellant treatments are not particularly restricted. The aforementioned (G) powders can be treated with various types of water-repellant surface treatment agents. As examples thereof, mention may be made of organosiloxane treatments such as a methylhydrogenpolysiloxane treatment, a silicone resin treatment, a silicone gum treatment, an acryl silicone treatment, a fluorinated silicone treatment and the like; metallic soap treatments such as a zinc stearate treatment and the like; silane treatments such as a silane coupling agent treatment, an alkylsilane treatment and the like; fluorine compound treatments such as a perfluoroalkylsilane treatment, a perfluoroalkyl phosphate treatment, a perfluoro polyether treatment and the like; amino acid treatments such as an N-lauroyl-L-lysine treatment and the like; oil agent treatments such as a squalane treatment and the like; acryl treatments such as an alkyl acrylate treatment and the like. The aforementioned treatments can be used in combination of two or more types thereof.

As the aforementioned (G) powders, silicone elastomer powders can also be used. The silicone elastomer powder is a crosslinked product of a linear diorganopolysiloxane mainly formed from a diorganosiloxane unit (D unit). The silicone elastomer powder can be preferably produced by crosslink-reacting an organohydrogenpolysiloxane having a silicon-binding hydrogen atom at the side chain or the terminal and a diorganopolysiloxane having an unsaturated hydrocarbon group such as an alkenyl group or the like at the side chain or the terminal, in the presence of a catalyst for a hydrosilylation reaction. The silicone elastomer powder has an increased flexibility and elasticity, and exhibits a superior oil-absorbing property, as compared with a silicone resin powder formed from T units and Q units. For this reason, the silicone elastomer powder absorbs sebum on the skin and can prevent makeup running.

The silicone elastomer powders can be in various forms such as a spherical form, a flat form, an amorphous form and the like. The silicone elastomer powders may be in the form of an oil dispersant. In the cosmetic of the present invention, silicone elastomer powders in the form of particles, which have a primary particle size observed by an electron microscope and/or an average primary particle size measured by a laser diffraction/scattering method ranging from 0.1 to 50 µm, and in which the primary particle is in a spherical form, can be preferably blended. In addition, the silicone elastomer constituting the silicone elastomer powders may have a hardness preferably not exceeding 80, and more preferably not exceeding 65, when measured by means of a type A durometer according to JIS K 6253 "Method for determining hardness of vulcanized rubber or thermoplastic rubber".

The aforementioned silicone elastomer powders can be used in the cosmetic for hair of the present invention, in the form of an aqueous dispersion. As examples of commercially available products of the aforementioned aqueous dispersions, mention may be made of, for example, "BY 29-129" and "PF-2001 PIF Emulsion" manufactured by Dow Corning Toray Co., Ltd., and the like. By blending an aqueous dispersion (=suspension) of the aforementioned silicone elastomer powders, a sensation during use of the cosmetics for hair, and in particular, the cosmetics for hair in the form of an oil-in-water emulsion can be further improved.

The silicone elastomer powders may be subjected to a surface treatment with a silicone resin, silica or the like. As examples of the aforementioned surface treatments, mention may be made of, for example, those described in Japanese Unexamined Patent Application, First Publication No. H02-243612; Japanese Unexamined Patent Application, First Publication No. H08-12545; Japanese Unexamined Patent Application, First Publication No. H08-12546; Japanese Unexamined Patent Application, First Publication No. H08-12524; Japanese Unexamined Patent Application, First Publication No. H09-241511; Japanese Unexamined Patent Application, First Publication No. H10-36219; Japanese Unexamined Patent Application, First Publication No. H11-193331; Japanese Unexamined Patent Application, First Publication No. 2000-281523 and the like. As the silicone elastomer powders, crosslinking silicone powders listed in "Japanese Cosmetic Ingredients Codex (JCIC)" correspond thereto. As commercially available products, there are Trefil E-506S, Trefil E-508, 9701 Cosmetic Powder, and 9702 Powder, manufactured by Dow Corning Toray Co., Ltd., and the like. As examples of the surface treatment agents, mention may be made of methylhydrogenpolysiloxane, silicone resins, metallic soap, silane coupling agents, inorganic oxides such as silica, titanium oxide and the like and fluorine compounds such as perfluoroalkylsilane, perfluoroalkyl phosphoric ester salts and the like.

In particular, the cosmetic for hair of the present invention comprising the aforementioned powder (G) which has been subjected to a surface treatment with a powder surface treatment agent comprising the aforementioned (A) co-modified organopolysiloxane can exhibit superior stability.

The blending amount of the aforementioned (G) powder in the cosmetic for hair of the present invention is not particularly restricted, and may preferably range from 0.1 to 50% by weight (mass), more preferably range from 1 to 30% by weight (mass), and furthermore preferably range from 5 to 15% by weight (mass) with respect to the total amount of the cosmetic.

Solid Silicone Resin or Crosslinking Organopolysiloxane

The cosmetic for hair of the present invention can further comprise (H) a solid silicone resin or crosslinking organopolysiloxane. The solid silicone resin or crosslinking organopolysiloxane is preferably hydrophobic so that it is completely insoluble in water at room temperature or the solubility thereof with respect to 100 g of water is below 1% by weight (mass).

The aforementioned (H) solid silicone resin or crosslinking organopolysiloxane is an organopolysiloxane with a highly branched molecular structure, a net-like molecular structure or a cage-like molecular structure, and may be in the form of a liquid or solid at room temperature. Any silicone resins usually used in cosmetics for hair can be used unless they are contrary to the purposes of the present invention. In the case of a solid silicone resin, the silicone resin may be in the form of particles such as spherical powders, scale powders, needle powders platy flake powders (including platy powders having an aspect ratio of particles and the outer appearance which are generally understood as a plate form) or the like. In particular, silicone resin powders containing a monoorganosiloxy unit (T unit) and/or a siloxy unit (Q unit) described below are preferably used.

Blending the aforementioned (H) solid silicone resin together with the aforementioned (A) co-modified organopolysiloxane is useful, since the miscibility with the aforementioned (B) oil agents and the uniformly dispersing property can be improved, and at the same time, an effect of improving a sensation during use such as uniform adhesiveness with respect to the part to be applied, obtained in accordance with blending the aforementioned (H) solid silicone resin can be obtained.

As examples of the aforementioned (H) solid silicone resins, mention may be made of, for example, MQ resins, MDQ resins, MTQ resins, MDTQ resins, TD resins, TQ resins, or TDQ resins comprising any combinations of a triorganosiloxy unit (M unit) (wherein the organo group is a methyl group alone, or a methyl group in combination with a vinyl group or a phenyl group), a diorganosiloxy unit (D unit) (wherein the organo group is a methyl group alone, or a methyl group in combination with a vinyl group or a phenyl group), a monoorganosiloxy unit (T unit) (wherein the organo group is a methyl group, a vinyl group or a phenyl group), and a siloxy unit (Q unit). In addition, as other examples thereof, mention may be made of trimethylsiloxysilicic acid, polyalkylsiloxysilicic acid, trimethylsiloxysilicic acid containing dimethylsiloxy units and alkyl(perfluoroalkyl) siloxysilicic acid. The aforementioned silicone resins are preferably oil soluble, and, in particular, preferably are soluble in a volatile silicone.

In particular, a phenyl silicone resin with an increased refractive index which has an increased content of a phenyl group (such as 217 Flake Resin manufactured by Dow Corning Toray Co., Ltd.) can easily form silicone resin powders in the form of flakes. In the case of blending the powders in a cosmetic for hair, a brilliant transparent impression can be provided to the skin and hair.

The aforementioned (H) crosslinking organopolysiloxane preferably has a structure in which an organopolysiloxane chain is three-dimensionally crosslinked by a reaction with a crosslinking component formed from a polyether unit, an alkylene unit having 4 to 20 carbon atoms, and an organopolysiloxane unit, or the like.

The aforementioned (H) crosslinking organopolysiloxane can be particularly obtained by addition-reacting an organohydrogenpolysiloxane having silicon-binding hydrogen atoms, a polyether compound having unsaturated bonds at both terminals of the molecular chain, an unsaturated hydrocarbon having more than one double bonds in a molecule, and an organopolysiloxane having more than one double bonds in a molecule. Here, the crosslinking organopolysiloxane may or may not have a modifying functional group such as an unreacted silicon-binding hydrogen atom, an aromatic hydrocarbon group such as a phenyl group or the like, a long chain alkyl group having 6 to 30 carbon atoms such as an octyl group, a polyether group, a carboxyl group, a silylalkyl group having the aforementioned carbosiloxane dendrimer structure or the like, and can be used without restrictions of physical modes and preparation methods such as dilution, properties and the like.

As one example, the aforementioned crosslinking organopolysiloxane can be obtained by addition-reacting an organohydrogenpolysiloxane which is formed from a structure unit selected from the group consisting of a $SiO_2$ unit, a $HSiO_{1.5}$ unit, a $R^bSiO_{1.5}$ unit, a $R^bHSiO$ unit, a $R^b{}_2SiO$ unit, a $R^b{}_3SiO_{0.5}$ unit and a $R^b{}_2HSiO_{0.5}$ unit, wherein $R^b$ is a substituted or non-substituted monovalent hydrocarbon group having 1 to 30 carbon atoms, excluding an aliphatic unsaturated group, and a part of Rb is a monovalent hydrocarbon group having 8 to 30 carbon atoms, and at the same time, includes 1.5 or more, on average, of hydrogen atoms binding to the silicon atom in the molecule, with a crosslinking component selected from the group consisting of a polyoxyalkylene compound having unsaturated hydrocarbon groups at both terminals of the molecular chain, a polyether compound such as a polyglycerol compound, a polyglycidyl ether compound or the like, an unsaturated hydrocarbon which is an α,ω-diene represented by the following general formula: $CH_2=CH-C_rH_{2r}-CH=CH_2$, wherein r is an integer ranging from 0 to 26, and an organopolysiloxane which is formed from a $SiO_2$ unit, a $(CH_2=CH)SiO_{1.5}$ unit, a $R^cSiO_{1.5}$ unit, a $R^c(CH_2=CH)SiO$ unit, a $R^c{}_2SiO$ unit, a $R^c{}_3SiO_{0.5}$ unit, and a $R^c{}_2(CH_2=CH)SiO_{0.5}$, wherein $R^c$ is a substituted or non-substituted monovalent hydrocarbon group having 1 to 30 carbon atoms, excluding an aliphatic unsaturated group, and includes 1.5 or more, on average, of vinyl groups binding to the silicon atom. The aforementioned modifying functional group can be introduced by carrying out an addition reaction with respect to the unreacted hydrogen atoms binding to the silicon atom in a molecule. For example, 1-hexene is reacted with a crosslinking organopolysiloxane having an unreacted hydrogen atom binding to the silicon atom, and thereby, a hexyl group which is an alkyl group having 6 carbon atoms can be introduced thereinto.

The aforementioned crosslinking organopolysiloxanes can be used without restrictions of physical modes and preparation methods such as dilution, properties and the like. As particularly preferable examples thereof, mention may be made of α,ω-diene crosslinking silicone elastomers (as commercially available products, DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation in the USA) described in U.S. Pat. No. 5,654,362. In the same manner as described above, as examples of partially crosslinking organopolysiloxane polymers, mention may be made of (dimethicone/vinyldimethicone) crosspolymer, (dimethicone/phenylvinyldimethicone) crosspolymer, (PEG-8 to 30/C6 to C30 alkyldimethicone) crosspolymer, (vinyldimethicone/C6 to C30 alkyldimethicone) crosspolymer, (dimethicone/polyglycerol) crosspolymer and the like, in the case of using INCI names (International Nomenclature Cosmetic Ingredient labeling names).

In the case of blending an emulsifiable crosslinking organopolysiloxane formed by crosslinking by means of a polyether compound in a cosmetic for hair as a component, the aforementioned co-modified organopolysiloxane can function as a dispersant. For this reason, there is an advantage in that a uniform emulsification system can be formed.

On the other hand, in the case of blending a non-emulsifiable crosslinking organopolysiloxane formed by crosslinking by means of an unsaturated hydrocarbon group such as a diene or an organopolysiloxane in a cosmetic for hair as a component, an adhesive sensation to the hair can be improved. In addition, there is an advantage in that good compatibility with the other oil agent(s) can be exhibited, and the whole oil system can be uniformly and stably blended in the cosmetic for hair.

The aforementioned (H) solid silicone resin or crosslinking organopolysiloxane can be blended alone or in combination with two or more types thereof in accordance with the purpose thereof. The solid silicone resin or crosslinking organopolysiloxane may be blended in an amount preferably ranging from 0.05 to 25% by weight (mass) and more preferably ranging from 0.1 to 15% by weight (mass), with respect to the total amount of the cosmetic for hair, in accordance with the purpose and blending intention.

Acryl Silicone Dendrimer Copolymer

The cosmetic for hair of the present invention can further comprise (I) an acryl silicone dendrimer copolymer. The aforementioned (I) acryl silicone dendrimer copolymer is a vinyl-based polymer having a carbosiloxane dendrimer structure at the side chain. As examples thereof, mention may be, in particular, preferably made of vinyl-based polymers described in Japanese Patent No. 4,009,382 (Japanese Unexamined Patent Application, First Publication No. 2000-063225). As examples of commercially available products, mention may be made of FA 4001 CM Silicone Acrylate, and FA 4002 ID Silicone Acrylate, manufactured by Dow Corning Toray Co., Ltd., and the like. An acryl silicone dendrimer copolymer having a long chain alkyl group having 8 to 30 carbon atoms and preferably having 14 to 22 carbon atoms at the side chain or the like may be used. In the case of blending the aforementioned acryl silicone dendrimer copolymer alone, a superior property of forming a film can be exhibited. For this reason, by blending the dendrimer copolymer in the cosmetic for hair according to the present invention, a strong coating film can be formed on the applied part, and durability of a sebum resistance property, a rub resistance property and the like can be considerably improved.

By using the aforementioned (A) co-modified organopolysiloxane together with the aforementioned (I) acryl silicone dendrimer copolymer, there are advantages in that a surface protective property such as a sebum resistance property can be improved due to strong water repellency provided by the carbosiloxane dendrimer structure, and at the same time, irregularities such as pores and wrinkles of the skin to be applied can be effectively made inconspicuous. In addition, the aforementioned (A) co-modified organopolysiloxane can provide miscibility of the aforementioned (I) acryl silicone dendrimer copolymer with the other oil agent(s). For this reason, there is an advantage in that degradation of hair can be controlled for a long time.

The blending amount of the aforementioned (I) acryl silicone dendrimer copolymer can appropriately be selected in accordance with the purpose and blending intention. The amount may preferably range from 1 to 99% by weight (mass), and more preferably may range from 30 to 70% by weight (mass), with respect to the total amount of the cosmetic for hair.

UV-ray Protective Component

The cosmetic for hair of the present invention can further comprise (J) a UV-ray protective component. The aforementioned (J) UV-ray protective component is preferably hydrophobic so that the component is completely insoluble in water at room temperature or the solubility thereof with respect to 100 g of water is below 1% by weight (mass). The aforementioned (J) UV-ray protective component is a component for blocking or diffusing UV rays. Among UV-ray protective components, there are inorganic UV-ray protective components and organic UV-ray protective components. If the cosmetics for hair of the present invention are sunscreen cosmetics, at least one type of inorganic or organic UV-ray protective component, and in particular, an organic UV-ray protective component is preferably contained.

The inorganic UV-ray protective components may be components in which the aforementioned inorganic powder pigments, metal powder pigments and the like are blended as UV-ray dispersants. As examples thereof, mention may be made of metal oxides such as titanium oxide, zinc oxide, cerium oxide, titanium suboxide, iron-doped titanium oxides and the like; metal hydroxides such as iron hydroxides and the like; metal flakes such as platy iron oxide, aluminum flake and the like; and ceramics such as silicon carbide and the like. Among these, at least one type of a material selected from fine particulate metal oxides and fine particulate metal hydroxides with an average particle size ranging from 1 to 100 nm in the form of granules, plates, needles, or fibers is, in particular, preferred. The aforementioned powders are preferably subjected to conventional surface treatments such as fluorine compound treatments, among which a perfluoroalkyl phosphate treatment, a perfluoroalkylsilane treatment, a perfluoropolyether treatment, a fluorosilicone treatment, and a fluorinated silicone resin treatment are preferred; silicone treatments, among which a methylhydrogenpolysiloxane treatment, a dimethylpolysiloxane treatment, and a vapor-phase tetramethyltetrahydrogencyclotetrasiloxane treatment are preferred; silicone resin treatments, among which a trimethylsiloxysilicic acid treatment is preferred; pendant treatments which are methods of adding alkyl chains after the vapor-phase silicone treatment; silane coupling agent treatments; titanium coupling agent treatments; silane treatments among which an alkylsilane treatment and an alkylsilazane treatment are preferred; oil agent treatments; N-acylated lysine treatments; polyacrylic acid treatments; metallic soap treatments in which a stearic acid salt or a myristic acid salt is preferably used; acrylic resin treatments; metal oxide treatments and the like. Multiple treatments described above are preferably carried out. For example, the surface of the fine particulate titanium oxide can be coated with a metal oxide such as silicon oxide, alumina or the like, and then, a surface treatment with an alkylsilane can be carried out. The total amount of the material used for the surface treatment may preferably range from 0.1 to 50% by weight (mass) based on the amount of the powder.

The organic UV-ray protective components are generally lipophilic. More particularly, as examples of the aforementioned organic UV-ray protective components, mention may be made of benzoic acid-based UV-ray absorbers such as paraminobenzoic acid (hereinafter, referred to as PABA), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, 2-[4-(diethylamino)-2-hydroxybenzoyl]benzoic acid hexyl ester (trade name: Uvinul A Plus) and the like; anthranilic acid-based UV-ray absorbers such as homomethyl N-acetylanthranilate and the like; salicylic acid-based UV-ray absorbers such as amyl salicylate, menthyl salicylate, homomethyl salicylate, octyl salicylate, phenyl salicylate, benzyl salicylate, p-isopropanolphenyl salicylate and the like; cinnamic acid-based UV-ray absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxy cinnamate, ethyl α-cyano-β-phenylcinnamate, 2-ethylhexyl α-cyano-β-phenylcinnamate, glyceryl mono-2-ethylhexanoyl-diparamethoxycinnamate, 3-methyl-4-[methylbis(trimethylsiloxy)silyl]butyl 3,4,5-trimethoxycinnamate, dimethicodiethyl benzal malonate (trade name: Parsol SLX (INCI name=polysilicone-15) and the like; benzophenone-based UV-ray absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, hydroxy-4-n-octoxybenzophenone, 4-hydroxy-3-carboxybenzophenone and the like; 3-(4'-methylbenzylidene)-d,l-camphor; 3-benzylidene-d,l-camphor; urocanic acid; ethyl urocanate; 2-phenyl-5-methylbenzoxazole; benzotriazole-based UV-ray absorbers such as 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzaladine, dianisoylmethane, 4-methoxy-4'-t-butylbenzoylmethane, 5-(3,3-dimethyl-2-norbonylidene)-3-pentan-2-one, 2,2'-methylenebis(6-(2H-benzotriazol-2-yl)-4-(1,1,3,3-tetramethylbutyl)phenol) (trade name: trademark TINOSORB M) and the like; triazine-based UV-ray absorbers such as 2,4,6-tris[4-(2-ethylhexyloxycarbonyl)anilino]1,3,5-triazine (INCI: octyltriazone), 2,4-bis{[4-(2-ethyl-hexyloxy)-2-hydroxy]phenyl}-6-(4-methoxyphenyl)-1,3,5-triazine (INCI: bis-ethylhexyloxyphenol methoxyphenyl triazine, trade name: trademark TINOSORB S) and the like; 2-ethylhexyl 2-cyano-3,3-diphenylprop-2-enoate (INCI: octocrylene) and the like.

Furthermore, hydrophobic polymer powders containing the aforementioned organic UV-ray protective components inside thereof can also be used. The polymer powder may be hollow or not, may have an average primary particle size thereof ranging from 0.1 to 50 μm and may have a particle size distribution thereof of either broad or sharp. As examples of the polymers, mention may be made of acrylic resins, methacrylic resins, styrene resins, polyurethane resins, polyethylene, polypropylene, polyethylene terephthalate, silicone resins, nylons, acrylamide resins, and silylated polypeptide resins. Polymer powders containing the organic UV-ray protective components in an amount ranging from 0.1 to 30% by weight (mass) with respect to the amount of the powder are preferred. Polymer powders containing 4-tert-butyl-4'-methoxydibenzoylmethane, which is a UV-A absorber, are particularly preferred.

The aforementioned (J) UV-ray protective components which can be preferably used in the cosmetics for hair of the present invention may be at least one type of compound selected from the group consisting of fine particulate titanium oxide, fine particulate zinc oxide, 2-ethylhexyl paramethoxycinnamate, 4-tert-butyl-4'-methoxydibenzoylmethane, benzotriazole-based UV-ray absorbers and triazine-based UV-ray absorbers. The aforementioned (J) UV-ray protective components are commonly used and easily available, and exhibit superior effects of preventing ultraviolet rays. For these reasons, the aforementioned UV-ray protective components are preferably used. In particular, inorganic UV-ray protective components and organic UV-ray protective components are preferably used in combination. In addition, UV-A protective components and UV-B protective components are further preferably used in combination.

In the cosmetic for hair of the present invention, by use of the aforementioned (A) co-modified organopolysiloxane together with the aforementioned (J) UV-ray protective component(s), the whole feeling on touch and storage stability of the cosmetic can be improved, and at the same time, the UV-ray protective component(s) can be stably dispersed in the cosmetic for hair. For this reason, superior UV-ray protective functions can be provided to the cosmetic.

In the cosmetic of the present invention, the aforementioned (J) UV-ray protective component(s) may be blended in a total amount preferably ranging from 0.1 to 40.0% by weight (mass), and more preferably ranging from 0.5 to 15.0% by weight (mass), with respect to the total amount of the cosmetic can be blended.

Oxidation Dye

In the case of using the cosmetic for hair of the present invention as an oxidation dye preparation, the cosmetic for hair of the present invention can comprise (K) an oxidation dye. As the aforementioned (K) oxidation dye, one which is generally used in an oxidation dye preparation such as an oxidation dye precursor, a coupler or the like can be used. For example, as examples of oxidation dye precursors, mention may be made of phenylene diamines, aminophenols, diaminopyridines, salts thereof such as hydrochloride salts, sulfate salts and the like. More particularly, as examples thereof, mention may be made of phenylenediamines such as p-phenylenediamine, toluene-2,5-diamine, toluene-3,4-diamine, 2,5-diaminoanisole, N-phenyl-p-phenylenediamine, N-methyl-p-phenylenediamine, N,N-dimethyl-p-phenylenediamine, 6-methoxy-3-methyl-p-phenylenediamine, N,N-diethyl-2-methyl-p-phenylenediamine, N-ethyl-N-(hydroxyethyl)-p-phenylenediamine, N-(2-hydroxypropyl)-p-phenylenediamine, 2-chloro-6-methyl-p-phenylenediamine, 2-chloro-p-phenylenediamine, N,N-bis-(2-hydroxyethyl)-p-phenylenediamine, 2,6-dichloro-p-phenylenediamine, 2-chloro-6-bromo-p-phenylenediamine and the like; aminophenols such as p-aminophenol, o-aminophenol, 2,4-diaminophenol, 5-aminosalicylic acid, 2-methyl-4-aminophenol, 3-methyl-4-aminophenol, 2,6-dimethyl-4-aminophenol, 3,5-dimethyl-4-aminophenol, 2,3-dimethyl-4-aminophenol, 2,5-dimethyl-4-aminophenol, 2-chloro-4-aminophenol, 3-chloro-4-aminophenol, and the like; diaminopyridines such as 2,5-diaminopyridine and the like; salts thereof; and the like. As examples of couplers, mention may be made of resorcinol, m-aminophenol, m-phenylenediamine, 2,4-diaminophenoxyethanol, 5-amino-o-cresol, 2-methyl-5-hydroxyethylaminophenol, 2,6-diaminopyridine, catechol, pyrogallol, gallic acid, tannic acid, and the like, as well as salts thereof. As other examples, those listed in "Japanese Standards of Quasi-drug Ingredients" (issued on June, 1991, by YAKUJI NIPPO LIMITED) can also be appropriately used. In addition, the aforementioned oxidation dye precursors and couplers can be used alone or in combination with two or more types thereof, and at least an oxidation dye precursor is preferably used. The blending amount of the oxidation dye preferably ranges from about 0.01 to 10% by weight (mass) of the total amount of the composition in view of dyeing properties and safety such as skin irritation or the like.

In the case of using the cosmetic for hair of the present invention as a double-agent type oxidation dye preparation, an alkaline agent and the aforementioned (K) oxidation dye (preferably further comprising a coupler) are contained in the first agent, and an oxidant is contained in the second agent, and at the time of use, the first agent and the second agent are mixed in a ratio usually ranging from 1:5 to 5:1, followed by using the mixture.

In the case of using the cosmetic for hair of the present invention as a hair bleaching preparation, the cosmetic for hair of the present invention can comprise the aforementioned oxidant. In the case of using the cosmetic for hair of the present invention as a double-agent type hair bleaching preparation, an alkaline agent is contained in the first agent, and an oxidant is contained in the second agent, and at the time of use, the first agent and the second agent are mixed in a ratio usually ranging from 1:5 to 5:1, followed by using the mixture.

Direct Dye

In the case of using the cosmetic for hair of the present invention as a temporary hair coloring preparation (such as a hair manicure), the cosmetic for hair of the present invention can comprise (L) a direct dye. As examples of direct dyes, mention may be made of, for example, a nitro dye, an anthraquinone dye, an acid dye, an oil-soluble dye, a basic dye and the like.

As examples of nitro dyes, mention may be made of HC Blue 2, HC Orange 1, HC Red 1, HC Red 3, HC Yellow 2, HC Yellow 4, and the like. As examples of anthraquinone dyes, mention may be made of 1-amino-4-methylaminoanthraquinone, 1,4-diaminoanthraquinone and the like.

As examples of acid dyes, mention may be made of Red No. 2, Red No. 3, Red No. 102, Red No. 104, Red No. 105, Red No. 106, Red No. 201, Red No. 227, Red No. 230, Red No. 232, Red No. 401, Red No. 502, Red No. 503, Red No. 504, Red No. 506, Orange No. 205, Orange No. 206, Orange No. 207, Yellow No. 4, Yellow No. 5, Yellow No. 202, Yellow No. 203, Yellow No. 402, Yellow No. 403, Yellow No. 406, Yellow No. 407, Green No. 3, Green No. 201, Green No. 204, Green No. 205, Green No. 401, Green No. 402, Blue No. 1, Blue No. 2, Blue No. 202, Blue No. 205, Violet No. 401, Black No. 401, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184, Brilliant Black 1 and the like.

As examples of oil-soluble dyes, mention may be made of Red No. 215, Red No. 218, Red No. 225, Orange No. 201, Orange No. 206, Yellow No. 201, Yellow No. 204, Green No. 202, Violet No. 201, Red No. 501, Red No. 505, Orange No. 403, Yellow No. 404, Yellow No. 405, Blue No. 403 and the like. For example, they are used in a coloring rinse, coloring treatment or the like.

As examples of basic dyes, mention may be made of Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 57, Basic Yellow 87, Basic Orange 31, and the like.

Among these, acid dyes are preferred, and in particular, Yellow No. 4, Yellow No. 203, Yellow No. 403, Orange No. 205, Green No. 3, Green No. 201, Green No. 204, Red No. 2, Red No. 104, Red No. 106, Red No. 201, Red No. 227, Blue No. 1, Blue No. 205, Violet No. 401, and Black No. 401 are preferred. The aforementioned (L) direct dyes can be used as one or more types thereof. The blending amount thereof in the cosmetic for hair of the present invention is not particularly restricted, and may preferably range from 0.005 to 5% by weight (mass) and more preferably range from 0.01 to 2% by weight (mass) with respect to the total weight (mass) of the composition.

In the case of using the cosmetic for hair of the present invention as a permanent waving preparation, the cosmetic for hair of the present invention can comprise the aforementioned reductant and oxidant. In the case of using the cosmetic for hair of the present invention as a double-agent type permanent waving preparation, for example, a reductant (preferably comprising an alkaline agent) is contained in the first agent and an oxidant is contained in the second agent. First, the first agent is applied to hair to dissociate disulfide bonds of the hair; subsequently, a preferable hair style is formed; subsequently, the second agent is applied thereto to reform the disulfide bonds of the hair; and thereby, a hair style may be fixed.

Other Components

In the cosmetics for hair of the present invention, (M) other components usually used in cosmetics for hair can be blended within a range which does not impair the effects of the present invention, such as organic resins, moisture-retaining agents, preservatives, anti-microbial agents, perfumes, salts, oxidants or antioxidants, pH adjusting agents, chelating agents, algefacients, anti-inflammatory agents, physiologically active components (such as whitening agents, cell activators, agents for ameliorating skin roughness, blood circulation accelerators, astringents, antiseborrheic agents and the like), vitamins, amino acids, nucleic acids, hormones, clathrate compounds, natural plant extract components, seaweed extract components, herb components, water, volatile solvents and the like. The other components are not particularly restricted thereto. They can be appropriately used alone or in combination with two or more types thereof.

As examples of organic resins, mention may be made of polyvinyl alcohol, polyvinyl pyrrolidone, poly(alkyl acrylate) copolymers, and the like. The organic resin possesses a superior property of forming a film. For this reason, by blending the organic resin in the cosmetic for hair of the present invention, a strong coating film can be formed at the applied part, and durability such as sebum resistance and rub resistance or the like can be improved.

As examples of humectants, mention may be made of, for example, hyaluronic acid, chondroitin sulfate, pyrrolidone carboxylic acid salts, polyoxyethylene methylglucoside, polyoxypropylene methylglucoside, and the like. Needless to say, the aforementioned polyhydric alcohols exhibit a function of retaining moisture on the skin or hair.

As examples of the preservatives, mention may be made of, for example, alkyl paraoxybenzoates, benzoic acid, sodium benzoate, sorbic acid, potassium sorbate, phenoxyethanol and the like. As examples of the antimicrobial agents, mention may be made of benzoic acid, salicylic acid, carbolic acid, sorbic acid, alkyl paraoxybenzoates, parachlorometha-cresol, hexachlorophene, benzalkonium chloride, chlorhexidine chloride, trichlorocarbanilide, trichlosan, photosensitizers, isothiazolinone compounds such as 2-methyl-4-isothiazolin-3-one, 5-chloro-2-methyl-4-isothiazolin-3-one and the like, amine oxides such as dimethyl laurylamine oxide, dihydroxyethyl laurylamine oxide and the like, and the like.

In addition, as examples of anti-microbial agents, mention may be made of apolactoferrin; phenol-based compounds such as resorcinol; anti-microbial or fungicidal basic proteins or peptides such as iturin-based peptides, surfactin-based peptides, protamine or salts thereof (protamine sulfate and the like) and the like; polylysines such as ε-polylysine or salts thereof, and the like; anti-microbial metal compounds which can produce a silver ion, a copper ion or the like; antimicrobial enzymes such as protease, lipase, oxydoreductase, carbohydrase, transferase, phytase and the like; and the like.

As examples of perfume, mention may be made of perfume extracted from flowers, seeds, leaves, and roots of various plants; perfume extracted from seaweeds; perfume extracted from various parts or secretion glands of animals such as musk and sperm oil; or artificially synthesized perfume such as menthol, musk, acetate, and vanilla. The conventional perfume can be selected and blended in an appropriate amount in accordance with the formulations of the cosmetics for hair in order to provide a certain aroma or scent to the cosmetics for hair, or in order to mask unpleasant odor.

As examples of oxidants, mention may be made of, for example, hydrogen peroxide, peroxidized urea, alkali metal salts of bromic acid, and the like. As examples of antioxidants, mention may be made of, for example, tocopherol, butylhydroxyanisole, dibutylhydroxytoluene, phytic acid and the like. As the antioxidants, ascorbic acid and/or ascorbic acid derivatives may be used. As examples of ascorbic acid derivatives which can be used, mention may be made of, for example, sodium ascorbate, potassium ascorbate, calcium ascorbate, ammonium ascorbate, erythorbic acid, sodium erythorbate, sodium ascorbyl phosphate, ascorbyl citrate, ascorbyl acetate, ascorbyl tartarate, ascorbyl palmitate, ascorbyl stearate, ascorbyl glucoside and the like. In addition, as the antioxidants, the reductants may be used. For example, sulfurous acid, bisulfurous acid, thiosulfuric acid, thiolactic acid, thioglycolic acid, L-cysteine, N-acetyl-L-cysteine and salts thereof can be appropriately used.

As examples of pH adjustors, mention may be made of, for example, lactic acid, citric acid, glycolic acid, succinic acid, tartaric acid, dl-malic acid, potassium carbonate, sodium hydrogencarbonate, ammonium hydrogencarbonate and the like. In addition, inorganic alkalized agents such as ammonia and the like, and organic alkalized agents such as isopropanolamine, monoethanolamine, diethanolamine, triethanolamine, 2-amino-2-methyl-1-propanolamine and the like can also be used. The blending amount of the pH adjustors is not particularly restricted, and may preferably range from 0.01 to 20% by weight (mass) and more preferably range from 0.1 to 10% by weight with respect to the total weight (mass) of the composition.

As examples of chelating agents, mention may be made of, for example, alanine, sodium edetate, sodium polyphosphate, sodium metaphosphate, phosphoric acid and the like.

As examples of algefacients, mention may be made of l-menthol, camphor and the like.

As examples of physiologically active components, mention may be made of, for example, vitamins, amino acids, nucleic acids, hormones, components extracted from natural vegetables, seaweed extracted components, herbal medicine components, whitening agents such as placenta extracts, arbutin, glutathione, saxifrageous extracts and the like; cell activators such as royal jelly, and the like; agents for ameliorating skin roughness; blood circulation accelerators such as nonylic acid vanillylamide, benzyl nicotinate, beta-butoxyethyl nicotinate, capsaicin, gingerone, cantharide tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; anti-inflammatory agents such as ϵ-aminocaproic acid, glycyrrhizinic acid, β-glycyrrhetinic acid, lysozyme chloride, guaiazulene, hydrocortisone, allantoin, tranexamic acid, azulene and the like; and the like.

As examples of vitamins, mention may be made of vitamin As such as vitamin A oil, retinol, retinol acetate, retinol palmitate and the like; vitamin Bs such as vitamin B2s such as riboflavin, riboflavin butyrate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate and the like; pantothenic acids such as calcium pantothenate, D-pantothenyl alcohol, pantothenyl ethyl ether, acetyl pantothenyl ethyl ether and the like; and the like.

As examples of amino acids, mention may be made of glycine, valine, leucine, isoleucine, serine, threonine, phenylalanine, arginine, lysine, aspartic acid, glutamate, cystine, cysteine, methionine, tryptophan and the like.

As examples of nucleic acids, mention may be made of deoxyribonucleic acid and the like.

As examples of hormones, mention may be made of estradiol, ethenyl estradiol and the like.

In the preparations for external use of the present invention, natural vegetable extracted components, seaweed extracted components and herbal medicine components can be blended in accordance with the purposes thereof. As the aforementioned components, in particular, one or more types of components having effects such as whitening effects, anti-ageing effects, effects of ameliorating ageing, effects of beautifying skin, anti-microbial effects, preservative effects and the like can be preferably blended.

As detailed examples thereof, mention may be made of, for example, *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extract, *Sasa veitchii* extract, *Sophora angustifolia* extract, walnut extract, grapefruit extract, *Clematis vitalba* leaf extract, *chlorella* extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis idaea* extract, *Asiasarum sieboldi* extract, *Bupleurum falcatum* extract, umbilical extract, *Salvia* extract, *Crocus sativus* flower extract, sasa bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriobotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma-jobi* seed extract, *Artemisia princeps* extract, lavender extract, apple extract, lettuce extract, lemon extract, *Astragalus sinicus* extract, rose extract, rosemary extract, *Roman chamomile* extract, royal jelly extract, and the like. The aforementioned extracts may be water-soluble or oil-soluble.

The cosmetic for hair of the present invention may further comprise water. Therefore, the preparation for external use of the present invention can be in the form of an oil-in-water emulsion or a water-in-oil emulsion. In this case, the cosmetic for hair of the present invention exhibits superior emulsion stability and a superior sensation during use.

Water is not particularly restricted as long as it does not include any harmful components for human bodies and is clean. As examples thereof, mention may be made of tap water, purified water, and mineral water. In addition, in the cosmetic for hair, and in particular, the cosmetic for hair in the form of an emulsion composition of the present invention, the blending amount of water preferably ranges from 2 to 98% by weight (mass), with respect to the total weight (mass) of the cosmetic.

In the cosmetic for hair of the present invention, depending on the formulations and the purposes thereof, volatile solvents such as light isoparaffins, ethers, LPG, N-methylpyrrolidone, next-generation chlorofluorocarbons, and the like, can be blended in addition to water.

The aforementioned (A) co-modified organopolysiloxane may be blended in a cosmetic composition for hair, as it is, or alternatively, may be blended therein as an emulsion obtained by using water and a surfactant of the aforementioned component (C) beforehand. In addition, an emulsion may be produced by using an oil agent of the aforementioned component (B) or a part thereof, water and the surfactant of the aforementioned component (C), in addition to the aforementioned (A) co-modified organopolysiloxane, and then the emulsion may be blended in a cosmetic composition for hair. The form of the emulsion must be adapted with the form of the cosmetic composition for hair to be blended. For example, in the case of a hair cleansing cosmetic in the form of an oil-in-water emulsion, if the same type of oil-in-water emulsion of the (A) co-modified organopolysiloxane is prepared, the emulsion can be blended in the cosmetic as it is. In this case, as the surfactant of the aforementioned component (C) used in the preparation for the emulsion of the aforementioned (A) co-modified organopolysiloxane, an appropriate one is preferably selected in order to maintain stability of the blending system. The surfactants of the aforementioned component (C) may be a combination of plural types of surfactants, and different types of surfactants such as ionic surfactants, nonionic surfactants and the like can be used together in order to ensure stability of the emulsion.

The form of the emulsion may be not only an oil-in-water emulsion or water-in-oil emulsion, but also a multiple emulsion or microemulsion thereof. The form of the emulsion (oil-in-water type or water-in-oil type) and the particle size of the emulsion can be appropriately selected or adjusted.

In the case of the cosmetic for hair of the present invention is in the form of an oil-in-water emulsion, the dispersion phase of the aforementioned cosmetic is formed from particles obtained by emulsifying the aforementioned (A) co-modified organopolysiloxane or a mixture of the aforementioned (B) oil agent therewith by means of the surfactant of the aforementioned component (C). The average particle size thereof can be measured by a conventional measurement device using a laser diffraction/scattering method or the like. The cosmetic in the form of an oil-in-water emulsion may be a transparent microemulsion in which the average particle size of the dispersion phase measured is 0.1 μm or less, or may be a milky emulsion having a large particle size so that the average particle size exceeds 4 μm. In addition, in order to improve stability and transparency of the outer appearance of the emulsion, the emulsion particles can be miniaturized. In particular, in order to improve the adhesive property with respect to the hair or skin or the sensation during use, an emulsion having an average particle size ranging from 0.5 to 20 μm can be selected, and is preferred. For example, in the case of a microemulsion, stability is improved, and in the case of a cleansing cosmetic, foam quality is improved. In the case of a normal particle size ranging from submicrons to 4 μm, superior usability is exhibited, good balance between a blending effect and stability is exhibited, and preparation is easily carried out. In addition, in the case of a large particle size of several microns or more, and for example, ranging from 4 to 5 μm, improvements of adhesive properties to hair and a sensation during use may be expected.

The cosmetic for hair of the present invention in the form of an oil-in-water emulsion or a water-in-oil emulsion can be produced by mixing components of the aforementioned cosmetic using a mechanical force by means of an apparatus such as a homomixer, a paddle mixer, a Henschel mixer, a homodisper, a colloid mill, a propeller stirrer, a homogenizer, an in-line type continuous emulsifier, an ultrasonic emulsifier, a vacuum kneader or the like.

The cosmetic for hair of the present invention in the form of an emulsion essentially comprises the aforementioned (A) co-modified organopolysiloxane, and superior dispersion stability of a dispersion phase can be obtained. Therefore, the cosmetics for hair of the present invention exhibit superior stability over time, possess a uniform outer appearance, and provide a superior sensation during use.

The forms of the cosmetics for hair of the present invention are not particularly restricted, and may be in the form of liquids, creams, solids, pastes, gels, powders, lamellas, mousses, sprays, sheets, and the like, in addition to emulsions.

The cosmetic compositions for hair of the present invention include all usages for cosmetics to be applied on hair. In particular, the cosmetics of the present invention are preferably used in cosmetics for cleansing hair, cosmetics for conditioning hair, cosmetics for styling hair, and cosmetics for dyeing hair.

The cosmetics for cleansing hair are cleansing preparations used in order to wash and clean hair and/or scalp. The functions are diverse and in addition to a base function of cleansing, additional functions such as conditioning effects, effects of preventing dandruff, and the like may be possessed. More particularly, as examples thereof, mention may be made of shampoos, conditioning shampoos, anti-dandruff shampoos, and the like.

The cosmetics for conditioning hair are cosmetics for hair possessing functions of concealing damage of hair, repairing damage of hair, protecting hair from damage, or preventing damage of hair, and the like. The hair conditioning cosmetics may be applied immediately after cleansing hair or after drying hair. More particularly, as examples thereof, mention may be made of rinses, rinse-in-shampoos, hair conditioners, hair creams, hair treatments and the like.

The cosmetics for styling hair are cosmetics for the purpose of finishing hair, and are roughly divided into a type of mainly styling hair such as fixing and setting hair, and another type of mainly improving glossiness, a feeling on touch, texture, and easiness of handling of hair. By virtue of multi-functionalization and sophistication of cosmetics, some cosmetics possess both of the aforementioned functions. Some hair-styling cosmetics may exhibit functions overlapped with those of the cosmetics for conditioning hair. More particularly, as examples thereof, mention may be made of hair foams, hair sprays, hair styling lotions, hair gels, hair liquids, hair oils, hair waxes, preparations for use in blowing hair, and the like. In particular, as examples thereof, mention may be made of hair mists, super hard mousse, super hard gels, super hard sprays, hard mousse, hard gels, hard sprays, soft sprays, soft mousse, soft gels, lotions for use in blowing hair, lotions for use in straightening hair, mousse for use in straightening hair, water, pomades, hair liquids, wet gels, hair waxes, hair creams, hair milks, mousse for waving hair, styling essences and the like.

The cosmetics of dyeing hair are for temporarily, semi-temporarily or permanently coloring hair by physically or chemically acting on the surface of hair. As examples thereof, mention may be made of color sprays, color sticks, hair manicures, coloring lotions, gloss sprays, manicure sprays and the like.

The cosmetic compositions for hair of the present invention can comprise any combinations of the aforementioned optional components as long as the aforementioned (A) co-modified organopolysiloxane is contained. Namely, the cosmetic compositions for hair of the present invention can comprise any combination of the aforementioned (A) co-modified organopolysiloxane and at least any one of the following components (B) to (M).

(B) Oil agents
(C) Surfactants
(D) Water-soluble polymers
(E) Alcohols
(F) Thickening and/or gelling agents
(G) Powders
(H) Solid silicone resins or crosslinking organopolysiloxanes
(I) Acryl silicone dendrimer copolymers
(J) UV-ray protective components
(K) Oxidation hair dyes
(L) Direct dyes
(M) Organic resins, moisture-retaining agents, preservative, anti-microbial agents, perfumes, salts, oxidants or antioxidants, pH adjusting agents, chelating agents, algefacients, anti-inflammatory agents, physiologically active components (such as whitening agents, cell activators, agents for ameliorating skin roughness, blood circulation accelerators, astringents, antiseborrheic agents and the like), vitamins, amino acids, nucleic acids, hormones, clathrate compounds, natural plant extract components, seaweed extract components, herb components, water, volatile solvents and the like.

Among combinations of components (B) to (M), preferable combinations of the components for the cosmetics for hair of the present invention are described below.

(B)+{at least one selected from the group consisting of (C), (D), (E), (F), (G), (H), (I), (J), (K), (L) and (M)};
(B)+(C)+{at least one selected from the group consisting of (D), (E), (F), (G), (H), (I), (J), (K), (L) and (M)};
(B)+(C)+(D)+{at least one selected from the group consisting of (E), (F), (G), (H), (I), (J), (K), (L) and (M)};
(B)+(C)+(E)+{at least one selected from the group consisting of (D), (F), (G), (H), (I), (J), (K), (L) and (M)};
(B)+(C)+(F)+{at least one selected from the group consisting of (D), (E), (G), (H), (I), (J), (K), (L) and (M)};
(B)+(C)+(D)+(E)+{at least one selected from the group consisting of (F), (G), (H), (I), (J), (K), (L) and (M)};
(B)+(C)+(D)+(F)+{at least one selected from the group consisting of (E), (G), (H), (I), (J), (K), (L) and (M)};
(B)+(C)+(D)+(E)+(F)+{at least one selected from the group consisting of (G), (H), (I), (J), (K), (L) and (M)};
(C)+{at least one selected from the group consisting of (B), (D), (E), (F), (G), (H), (I), (J), (K), (L) and (M)};
(C)+(D)+{at least one selected from the group consisting of (B), (E), (F), (G), (H), (I), (J), (K), (L) and (M)};
(C)+(E)+{at least one selected from the group consisting of (B), (D), (F), (G), (H), (I), (J), (K), (L) and (M)};
(C)+(F)+{at least one selected from the group consisting of (B), (D), (E), (G), (H), (I), (J), (K), (L) and (M)};
(C)+(D)+(E)+{at least one selected from the group consisting of (B), (F), (G), (H), (I), (J), (K), (L) and (M)};
(C)+(D)+(F)+{at least one selected from the group consisting of (B), (E), (G), (H), (I), (J), (K), (L) and (M)};
(C)+(E)+(F)+{at least one selected from the group consisting of (B), (D), (G), (H), (I), (J), (K), (L) and (M)}; and
(C)+(D)+(E)+(F)+{at least one selected from the group consisting of (B), (G), (H), (I), (J), (K), (L) and (M)}.

The cosmetics for hair of the present invention generally comprise water.

Hereinafter, generally preferable combinations and the blending purposes thereof are described in detail, in accordance with types and usages of cosmetics to be applied on hair. It should be understood that the cosmetic compositions for hair according to the present invention are not restricted to the detailed compositions.

Among cosmetics for hair of the present invention, a cosmetic for cleansing hair may preferably comprise, in addition to the aforementioned (A) co-modified organopolysiloxane, the aforementioned (B) oil agent as a conditioning agent, the aforementioned (D) water-soluble polymer as a conditioning agent, the aforementioned (C) surfactant as a foaming and/or cleansing base agent, the aforementioned (E) alcohol as a humectant and/or a stabilizing agent, and the aforementioned (M) other components such as water, a pH adjustor, a preservative and the like, as representative components. In view of cleansing effects and the like, among components (C), (C1) an anionic surfactant may, in general, preferably be used, and at least one surfactant selected from (C3) a nonionic surfactant and (C4) an amphoteric surfactant may, in particular, preferably be used together therewith. In addition, as the aforementioned (B) oil agent, one or more types selected from dimethylpolysiloxanes, organo-modified silicones such as amino-modified silicones and the like, ester oils, lanolin derivatives and higher alcohols may preferably be used. In particular, in view of conditioning effects to hair, use of amino-modified silicones is preferred, and the amino equivalence and the like of the aforementioned modified silicones can be appropriately designed. In the same manner as described above, among the aforementioned components (D), in view of conditioning effects, use of (D1) a cationic water-soluble polymer may be preferred. In particular, in the case of using the aforementioned (A) co-modified organopolysiloxane together with the aforementioned (C1) anionic surfactant and (D1) cationic water-soluble polymer, there can be advantages in that superior foaming properties and a superior feeling on touch of foam can be obtained, superior cleansing properties can be exhibited, and smooth combability without a frictional sensation can be provided both at the time of wetting and at the time of drying after hair is cleaned.

Among the cosmetic compositions for hair of the present invention, a cosmetic for conditioning hair may comprise, in addition to the aforementioned (A) co-modified organopolysiloxane, the aforementioned (B) oil agent, and in particular, (B2-1) a higher alcohol, the aforementioned (C) surfactant, (E) alcohols, (D) water-soluble polymer (for example, as an aqueous thickening agent), and the aforementioned (M) other components such as water, pH adjustor, preservative, and the like, as representative blending components. In view of adhesive properties to hair, among the aforementioned components (C), use of (C2) a cationic surfactant as an essential component may, in general, be preferred. As examples thereof, mention may be made of a quaternary ammonium salt such as alkyltrimethylammonium chloride or the like or an alkylamidoamine such as diethylaminoethylamide stearate or the like. In addition, as the aforementioned (B) oil agent, one or more types selected from dimethylpolysiloxanes, organo-modified silicones such as amino-modified silicones and the like, ester oils, lanolin derivatives and higher alcohols may preferably be used. In particular, use of the higher alcohols is preferred in view of forming an alpha gel as a surfactant.

In addition, in view of retaining properties on hair and conditioning effects for hair, use of silicones may be preferred, and selection from amino-modified silicones or dimethylpolysiloxanes with a high degree of polymerization may also be preferred. In particular, use of silicones with a high degree of polymerization which are silicone gums is preferred. The amino equivalence or the like of the aforementioned modified silicones can be appropriately designed. In addition, in order to emulsify the aforementioned silicones, use of one or more types selected from (C3) nonionic surfactants and (C4) amphoteric surfactants, other than cationic surfactants, may be preferred. The aforementioned (D) water-soluble polymer may be preferably blended. In this case, as examples of the aforementioned component (D), mention may be made of water-soluble polymers other than cationic water-soluble polymers. In view of conditioning effects, use of natural water-soluble polymers such as guar gum and the like, semi-synthesized water-soluble polymers such as hydroxyethylcellulose and the like is, in particular, preferred. On the other hand, in the case of using the aforementioned (A) co-modified organopolysiloxane together with the aforementioned (B2-1) higher alcohol, and (C2) cationic surfactant, the cosmetic for conditioning hair can provide smooth combability without a frictional sensation both at the time of wetting and at the time of drying. At the time of drying, while smooth combability with a comb and fingers and a moisturizing feeling on touch can be exhibited, an uncomfortable sticky sensation is not exhibited and in addition, a flexible styling sensation can be provided to hair. In addition, the cosmetics for conditioning hair of the present invention can exhibit superior durability of the aforementioned effects.

Among the cosmetic compositions for hair, the cosmetic for styling hair may comprising, in addition to the aforementioned (A) co-modified organopolysiloxane, the aforementioned (B) oil agent, (C) surfactant, and (D) water-soluble polymer as essential components. The cosmetics for styling hair of the present invention may have oil-based raw materials as a base material or may have aqueous raw materials as a base material (namely, having (M) water as a carrier), and the base material therefor is not particularly restricted. The cosmetic for styling hair of the present invention preferably comprises an oil agent as the aforementioned component (B). The compositions and blending components may be determined in accordance with the formulation selected from a liquid, a cream, a solid, a paste, a gel, a mousse, and a spray. In the case of blending the aforementioned (A) co-modified organopolysiloxane of the present invention, smooth combability with a comb or fingers at the time of drying can be exhibited, a flexible styling sensation may be provided to hair, and superior durability of the aforementioned styling effects can be exhibited.

Use of the aforementioned (B) oil agent with a high degree of viscosity which is in the form of a wax or a gum at room temperature (25° C.), together with the aforementioned (B) oil agent which is in the form of a liquid at room temperature is preferred. In particular, use of a combination between an oil agent with a high degree of viscosity having 5,000 mPa·s or more at room temperature (more preferably an oil agent with a viscosity of 10,000 mPa·s or more to an oil agent in the form of a solid) and an oil agent with a low degree of viscosity having less than 5,000 mPa·s at room temperature (more preferably in the range of 0.65 to 3,000 mPa·s) is preferred. In addition, as the aforementioned component (D), use of a vinyl-based polymer such as polyvinylpyrrolidone, carboxyvinyl polymer or the like together with another water-soluble polymer is also preferred.

Among cosmetic compositions for hair, the cosmetic of dyeing hair may comprise, in addition to the aforementioned (A) co-modified organopolysiloxane, one or more types of hair dyeing components selected from the aforementioned (K) oxidation hair dyes and (L) direct dyes. In particular, by using the aforementioned (A) co-modified organopolysiloxane according to the present invention together with the aforementioned hair dyeing components, there can be advantages in that dispersing properties and stability of the hair dyeing components can be improved, color durability and development on hair can be enhanced, uneven coloring can be overcome, and hair can be beautifully dyed. In addition, in the case of using the aforementioned (L) direct dye, there can be an advantage in that it is relatively easy to rinse off the composition, if necessary.

EXAMPLES

Hereinafter, the present invention is described in detail with reference to examples. It should be understood that the present invention is not restricted to the examples. In the composition formulae described below, an Me$_3$SiO group (or a Me$_3$Si group) is indicated as "M", an Me$_2$SiO group is indicated as "D", and units in which a methyl group (Me) in M and D is modified by any substituent are respectively indicated as "$M^R$" and "$D^R$".

Synthesis Example 1

Synthesis of Silicone Compound No. 1

196.6 g of a methylhydrogenpolysiloxane represented by the following average compositional formula: $MD_{400}D^H{}_{10}M$, 13.6 g of a vinyltristrimethylsiloxysilane represented by the following average compositional formula: $CH_2=CH-Si(OSiMe_3)_3$, 5.5 g of glycerol monoallyl ether represented by the following structural formula: $CH_2=CH-CH_2-OCH_2CH(OH)CH_2OH$, and 90 g of isopropyl alcohol (IPA) were placed in a reactor, and the mixture was heated to 70° C. under a nitrogen stream while it was stirred. 0.060 g of a solution of a platinum-1,3-divinyl-1,1,3,3-tetramethyldisiloxane complex (Pt concentration=4.5% by weight (mass)) dissolved in IPA was added thereto, and the mixture was reacted for 5 hours at 80° C. Subsequently, with 2 g of the reaction mixture, it was confirmed that the reaction was completed, by means of an alkaline decomposition gas generation method (remaining Si—H group was decomposed by an aqueous solution/ethanol of KOH, and reaction index was calculated from the volume of generated hydrogen gas). The reaction mixture was heated under reduced pressure to remove low-boiling components by distillation. Thereby, a glycerol-modified silicone having a siloxane dendron structure represented by the following average compositional formula: $MD_{400}D^{R*31}{}_5D^{R*21}{}_5M$, wherein $R^{*21}=C_3H_6OCH_2CH(OH)CH_2OH$; and $R^{*31}=C_2H_4Si(OSiMe_3)_3$ was obtained. The product was in the form of a pale yellow opaque uniform viscous liquid.

Synthesis Example 2

Synthesis of Silicone Compound No. 2

151.3 g of a methylhydrogenpolysiloxane represented by the following average compositional formula: $MD_{150}D^H{}_{10}M$, 26.7 g of a vinyltristrimethylsiloxysilane represented by the following average compositional formula: $CH_2=CH-Si(OSiMe_3)_3$, 11.7 g of polyglycerol monoallyl ether, 10.2 g of diglycerol monoallyl ether and 200 g of IPA were placed in a reactor, and the mixture was heated to 65° C. under a nitrogen stream while it was stirred. 0.100 g of a solution of a platinum-1,3-divinyl-1,1,3,3-tetramethyldisiloxane complex (Pt concentration=4.5% by weight (mass)) dissolved in IPA was added thereto, and the mixture was reacted for 5 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a polyglycerol-modified silicone having a siloxane dendron structure represented by the following average compositional formula: $MD_{150}D^{R*31}{}_5D^{R*22}{}_2D^{R*23}{}_3M$, wherein $R^{*31}$ is the same as defined above; $R^{*22}$=—$C_3H_6O$—X, wherein X represents a tetraglycerol moiety; and $R^{*23}$=—$C_3H_6O$—X, wherein X represents a diglycerol moiety, was obtained. The product was in the form of a milky uniform viscous liquid.

The aforementioned polyglycerol monoallyl ether is a product synthesized by subjecting glycidol to ring-opening polymerization with respect to glycerol monoallyl ether, wherein the blending ratio of glycidol is 3 mol with respect to 1 mol of glycerol monoallyl ether. Glycerol monoallyl ether has two hydroxyl groups and glycidol can react with both hydroxyl groups. For this reason, the polyglycerol moiety contains not only a linear structure, but also a branched structure.

Synthesis Example 3

Synthesis of Silicone Compound No. 3

109.3 g of a methylhydrogenpolysiloxane represented by the following average compositional formula: $MD_{72}D^H{}_{12}M$, 66.3 g of a vinyltristrimethylsiloxysilane represented by the following average compositional formula: $CH_2$=CH—Si$(OSiMe_3)_3$, 24.3 g of polyglycerol monoallyl ether, 200 g of IPA, and 0.23 g of a solution containing 2.3% by weight (mass) of sodium acetate dissolved in methanol were placed in a reactor, and the mixture was heated to 50° C. under a nitrogen stream while it was stirred. 0.160 g of a solution containing 5% by weight (mass) of chloroplatinic acid dissolved in IPA was added thereto, and the mixture was reacted for 7 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a polyglycerol-modified silicone having a siloxane dendron structure represented by the following average compositional formula: $MD_{72}D^{R*31}{}_9D^{R*22}{}_3M$, wherein $R^{*31}$ and $R^{*22}$ are the same as defined above, was obtained. The product was in the form of a milky uniform gum.

Synthesis Example 4

Synthesis of Silicone Compound No. 4

116.6 g of a methylhydrogenpolysiloxane represented by the following average compositional formula: $MD_{72}D^H{}_{12}M$, 47.3 g of a vinyltristrimethylsiloxysilane represented by the following average compositional formula: $CH_2$=CH—Si$(OSiMe_3)_3$, 26.0 g of polyglycerol monoallyl ether, 200 g of IPA, and 0.20 g of a solution containing 2.3% by weight (mass) of sodium acetate dissolved in methanol were placed in a reactor, and the mixture was heated to 60° C. under a nitrogen stream while it was stirred. 0.08 g of a solution containing 5% by weight (mass) of chloroplatinic acid dissolved in IPA was added thereto, and the mixture was reacted for 2 hours at 80° C. Subsequently, with 2 g of the reaction mixture, it was confirmed that the reaction had proceeded 75 to 80%, by means of an alkaline decomposition gas generation method. Subsequently, 10.2 g of 1-decene and 0.08 g of a solution containing 5% by weight (mass) of chloroplatinic acid dissolved in IPA were added thereto, and the mixture was reacted for 6 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a polyglycerol-modified silicone having an alkyl group and a siloxane dendron structure represented by the following average compositional formula: $MD_{72}D^{R*11}{}_3D^{R*31}{}_6D^{R*22}{}_3M$, wherein $R^{*31}$ and $R^{*22}$ are the same as defined above; and $R^{*11}$=—$C_{10}H_{21}$, was obtained. The product was in the form of a brownish gray-white gum.

Synthesis Example 5

Synthesis of Silicone Compound No. 5

96.3 g of a methylhydrogenpolysiloxane represented by the following average compositional formula: $MD_{400}D^H{}_{10}M$, 4.0 g of a vinyltristrimethylsiloxysilane represented by the following average compositional formula: $CH_2$=CH—Si$(OSiMe_3)_3$, 7.3 g of polyglycerol monoallyl ether, 150 g of IPA, and 0.16 g of a solution containing 2.3% by weight (mass) of sodium acetate dissolved in methanol were placed in a reactor, and the mixture was heated to 75° C. under a nitrogen stream while it was stirred. 0.06 g of a solution containing 5% by weight (mass) of chloroplatinic acid dissolved in IPA was added thereto, and the mixture was reacted for 2 hours at 80° C. Subsequently, with 2 g of the reaction mixture, it was confirmed that the reaction had proceeded 85%, by means of an alkaline decomposition gas generation method. Subsequently, 1.2 g of 1-decene and 0.06 g of a solution containing 5% by weight (mass) of chloroplatinic acid dissolved in IPA were added thereto, and the mixture was reacted for 3 hours at 80° C. Again, with the reaction mixture, it was confirmed that the reaction was completed, by means of an alkaline decomposition gas generation method. 105.5 g of a dimethylpolysiloxane (2 cSt, 25° C.) was added the reaction mixture, followed by mixing them to dilute the reaction mixture. The reaction mixture was heated under reduced pressure to remove low-boiling components other than the diluent by distillation. Thereby, a polyglycerol-modified silicone having an alkyl group and a siloxane dendron structure represented by the following average compositional formula: $MD_{400}D^{R*11}{}_2D^{R*31}{}_3D^{R*22}{}_5M$, wherein $R^{*11}$, $R^{*22}$ and $R^{*31}$ are the same as defined above, (a mixture consisting of a composition containing Silicone Compound No. 5 and a dimethylpolysiloxane (2 cSt, 25° C.; diluent)) was obtained. The ratio of the aforementioned silicone composition:diluent was 1:1. The mixture was milky and uniform, and in the form of a gum although the mixture was diluted to a concentration of 50%.

Synthesis Example 6

Synthesis of Silicone Compound No. 6

105.5 g of a methylhydrogenpolysiloxane represented by the following average compositional formula: $MD_{72}D^H{}_{12}M$, 64.0 g of a vinyltristrimethylsiloxysilane represented by the following average compositional formula: $CH_2=CH-Si(OSiMe_3)_3$, 30.5 g of polyglyceryl eugenol, and 200 g of IPA were placed in a reactor, and the mixture was heated to 60° C. under a nitrogen stream while it was stirred. 0.130 g of a solution of a platinum-1,3-divinyl-1,1,3,3-tetramethyldisiloxane complex (Pt concentration=4.5% by weight (mass)) dissolved in IPA was added thereto, and the mixture was reacted for 3 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a polyglycerol-co-modified silicone having a siloxane dendron structure represented by the following average compositional formula: $MD_{72}D^{R*31}{}_9D^{R*24}{}_3M$, wherein $R^{*31}$ is the same as defined above; and $R^{*24}$ is shown as follows:

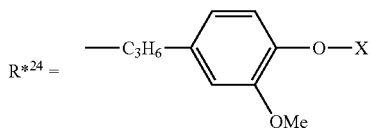

wherein X represents a tetraglycerol moiety, was obtained. The product was in the form of a translucent pale yellow rubber.

The aforementioned polyglyceryl eugenol is a product synthesized by subjecting glycidol to ring-opening polymerization with respect to eugenol, wherein the blending ratio of glycidol is 4 mol with respect to 1 mol of eugenol. When one glycidol is polymerized, the number of the hydroxyl groups present in the molecule increases to two. The remaining glycidols can react with both hydroxyl groups. For this reason, the polyglycerol moiety mainly consisting of tetraglycerol contains not only a linear structure, but also a branched structure.

Synthesis Example 7

Synthesis of Silicone Compound No. 7

112.3 g of a methylhydrogenpolysiloxane represented by the following average compositional formula: $MD_{72}D^H{}_{12}M$, 45.4 g of a vinyltristrimethylsiloxysilane represented by the following average compositional formula: $CH_2=CH-Si(OSiMe_3)_3$, 32.5 g of polyglyceryl eugenol, and 200 g of IPA were placed in a reactor, and the mixture was heated to 55° C. under a nitrogen stream while it was stirred. 0.100 g of a solution of a platinum-1,3-divinyl-1,1,3,3-tetramethyldisiloxane complex (Pt concentration=4.5% by weight (mass)) dissolved in IPA was added thereto, and the mixture was reacted for 2 hours at 80° C. Subsequently, with 2 g of the reaction mixture, it was confirmed that the reaction had proceeded 75% to 80%, by means of an alkaline decomposition gas generation method. Subsequently, 9.9 g of 1-decene was added thereto, and the mixture was reacted for one hour at 80° C. Again, with the reaction mixture, it was confirmed that the reaction was completed, by means of an alkaline decomposition gas generation method. The reaction mixture was heated under reduced pressure to remove low-boiling components by distillation. Thereby, a polyglycerol-modified silicone having a siloxane dendron structure and an alkyl group represented by the following average compositional formula: $MD_{72}D^{R*11}{}_3D^{R*31}{}_6D^{R*24}{}_3M$, wherein $R^{*31}$ and $R^{*24}$ are the same as defined above; and $R^{*11}=-C_{10}H_{21}$, was obtained. The product was in the form of a translucent topaz rubber.

Synthesis Example 8

Synthesis of Silicone Compound No. 8

130.2 g of a methylhydrogenpolysiloxane represented by the following average compositional formula: $MD_{400}D^H{}_{10}M$, 5.4 g of a vinyltristrimethylsiloxysilane represented by the following average compositional formula: $CH_2=CH-Si(OSiMe_3)_3$, 12.8 g of polyglyceryl eugenol, 150 g of IPA, and 0.15 g of a solution containing 2.3% by weight (mass) of sodium acetate dissolved in methanol were placed in a reactor, and the mixture was heated to 75° C. under a nitrogen stream while it was stirred. 0.06 g of a solution of a platinum-1,3-divinyl-1,1,3,3-tetramethyldisiloxane complex (Pt concentration=5% by weight (mass)) dissolved in IPA was added thereto, and the mixture was reacted for 2 hours at 80° C. Subsequently, with 2 g of the reaction mixture, it was confirmed that the reaction had proceeded 85%, by means of an alkaline decomposition gas generation method. 1.6 g of 1-decene and 0.06 g of a solution containing 5% by weight (mass) of chloroplatinic acid dissolved in IPA were added thereto, and the mixture was reacted for 3 hours at 80° C. Again, with the reaction mixture, it was confirmed that the reaction was completed, by means of an alkaline decomposition gas generation method. 145.0 g of a dimethylpolysiloxane (2 cSt, 25° C.) was added to the reaction mixture, followed by mixing them to dilute the reaction mixture. The reaction mixture was heated under reduced pressure to remove low-boiling components other than diluent by distillation. Thereby, a polyglycerol-modified silicone having an alkyl group and a siloxane dendron structure represented by the following average compositional formula: $MD_{400}D^{R*11}{}_2D^{R*31}{}_3D^{R*24}{}_5M$, wherein $R^{*11}$, $R^{*24}$ and $R^{*31}$ are the same as defined above, (a mixture consisting of a composition containing Silicone Compound No. 8 and a dimethylpolysiloxane (2 cSt, 25° C.; diluent)) was obtained. The ratio of the aforementioned silicone composition:diluent was 1:1. The mixture was pale yellow, uniform, and translucent, and in the form of a gum although the mixture was diluted to a concentration of 50%.

Comparative Synthesis Example 1

Synthesis of Silicone Compound RE 1

212.5 g of a methylhydrogenpolysiloxane represented by the following average compositional formula: $MD_{406}D^H{}_4M$, 4.9 g of a glycerol monoallyl ether represented by the following average compositional formula: $CH_2=CH-CH_2-OCH_2CH(OH)CH_2OH$, and 90 g of IPA were placed in a reactor, and the mixture was heated to 70° C. under a nitrogen stream while it was stirred. 0.053 g of a solution of a platinum-1,3-divinyl-1,1,3,3-tetramethyldisiloxane complex (Pt concentration=4.5% by weight (mass)) dissolved in IPA was added thereto, and the mixture was reacted for 3 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a glycerol-modified silicone represented by the following average compositional formula: $MD_{406}D^{R*21}{}_4M$, wherein $R^{*21}=-$ $C_3H_6OCH_2CH(OH)CH_2OH$, was obtained. The product was a pale yellow topraz, uniform, and translucent viscous liquid.

Comparative Synthesis Example 2

Synthesis of Silicone Compound RE 2

155.9 g of a methylhydrogenpolysiloxane represented by the following average compositional formula: $MD_{72}D^H{}_{12}M$, 13.0 g of a glycerol monoallyl ether represented by the following average compositional formula: $CH_2=CH-CH_2-OCH_2CH(OH)CH_2OH$, 41.1 g of 1-decene, and 63 g of IPA were placed in a reactor, and the mixture was heated to 45° C. under a nitrogen stream while it was stirred. 0.055 g of a solution of a platinum-1,3-divinyl-1,1,3,3-tetramethyldisiloxane complex (Pt concentration=4.5% by weight (mass)) dissolved in IPA was added thereto, and the mixture was reacted for one hour at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, an alkyl/glycerol-co-modified silicone represented by the following average compositional formula: $MD_{72}D^{R*11}{}_9D^{R*21}{}_3M$, wherein $R^{*21}$ is the same as defined above; and $R^{*11}=-C_{10}H_{21}$, was obtained. The product was a pale topaz and translucent liquid.

Comparative Synthesis Example 3

Synthesis of Silicone Compound RE 3

134.6 g of a methylhydrogenpolysiloxane represented by the following average compositional formula: $MD_{72}D^H{}_{12}M$, 36.2 g of 1-decene, 29.9 g of a polyglycerol monoallyl ether, 200 g of IPA, and 0.25 g of a solution containing 2.3% by weight (mass) of sodium acetate dissolved in methanol were placed in a reactor, and the mixture was heated to 55° C. under a nitrogen stream while it was stirred. 0.160 g of a solution containing 5% by weight (mass) of chloroplatinic acid dissolved in IPA was added thereto, and the mixture was reacted for 7 hours at 80° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, an alkyl/polyglycerol-co-modified silicone represented by the following average compositional formula: $MD_{72}D^{R*11}{}_9D^{R*22}{}_3M$, wherein $R^{*11}$ is the same as defined above; and $R^{*22}=-C_3H_6O-X$, in which X is a tetraglycerol moiety, was obtained. The product was a gray gum, as a whole, but the product was not uniform and phase separation (pale topaz gum phase) partially occurred.

Comparative Synthesis Example 4

Synthesis of Silicone Compound RE 4

111.6 g of a methylhydrogenpolysiloxane represented by the following average compositional formula: $MD_{61}D^H{}_{15}M$ was placed in a reactor, and a mixture containing 30.9 g of a dimethylpolysiloxane of which one terminal was modified with a vinyl group represented by the following structural formula: $CH_2=CHSiMe_2(OSiMe_2)_6OSiMe_3$ and 0.10 g of a solution of a platinum-1,3-divinyl-1,1,3,3-tetramethyldisiloxane complex (Pt concentration=0.5% by weight (mass)) dissolved in toluene was added dropwise thereto. The mixture was stirred at room temperature. Thereby, a linear siloxane branch-type polysiloxane intermediate was obtained.

In addition, 7.0 g of a triglycerol monoallyl ether, 50.4 g of 1-dodecene, 100 g of IPA, and 0.40 g of a solution of a platinum-1,3-divinyl-1,1,3,3-tetramethyldisiloxane complex (Pt concentration=0.5% by weight (mass)) dissolved in IPA were placed in another reactor. The linear siloxane branch-type polysiloxane synthesized above was added dropwise thereto under refluxing condition of the solvent under a nitrogen stream while it was stirred. After completion of the dropwise addition, the heating and stirring were continued for 3 hours. Subsequently, with 2 g of the reaction mixture, it was confirmed that the reaction was completed, by means of an alkaline decomposition gas generation method. The reaction mixture was heated under reduced pressure to remove low-boiling components by distillation. Furthermore, the reaction mixture was filtered. Thereby, an alkyl/linear siloxane/polyglycerol-co-modified silicone represented by the following average compositional formula: $MD_{61}D^{R*12}{}_{12}D^{R*41}{}_2D^{R*25}{}_1M$, wherein $R^{*12}=-C_{12}H_{25}$; $R^{*41}=-C_2H_4SiMe_2(OSiMe_2)_6OSiMe_3$; and $R^{*25}=-C_3H_6O-X$, in which X is a tetraglycerol moiety, was obtained. The product was a nearly colorless, translucent, and uniform liquid.

Comparative Synthesis Example 5

Synthesis of Silicone Compound RE 5

110.6 g of a methylhydrogenpolysiloxane represented by the following average compositional formula: $MD_{72}D^H{}_{12}M$, and 89.4 g of a vinyltristrimethylsiloxysilane represented by the following average structural formula: $CH_2=CH-Si(OSiMe_3)_3$ were placed in a reactor, and the mixture was heated to 50° C. under a nitrogen stream while it was stirred. 0.06 g of a solution of a platinum-1,3-divinyl-1,1,3,3-tetramethyldisiloxane complex (Pt concentration=4.5% by weight (mass)) dissolved in IPA was added thereto, and the mixture was reacted for 3 hours at 110° C. Subsequently, with 2 g of the reaction mixture, it was confirmed that the reaction was completed, by means of an alkaline decomposition gas generation method. The reaction mixture was heated under reduced pressure to remove low-boiling components by distillation. Thereby, a silicone having a siloxane dendron structure represented by the following average compositional formula: $MD_{72}D^{R*31}{}_{12}M$, wherein $R^{*31}=-C_2H_4Si(OSiMe_3)_3$, was obtained. The product was a pale yellow transparent, and uniform liquid.

Average compositional formulae of "Silicone Compound No. 1" to "Silicone Compound No. 8" used in Examples and "Silicone Compound RE 1" to "Silicone Compound RE 5" used in Comparative Examples are shown in Table 1.

TABLE 1

| Silicone Compound | Average compositional formula | Property |
|---|---|---|
| Silicone Compound No. 1 | $MD_{400}D^{R*31}{}_5D^{R*21}{}_5M$ | Pale yellow, translucent, uniform and viscous liquid |
| Silicone Compound No. 2 | $MD_{150}D^{R*31}{}_5D^{R*22}{}_2D^{R*23}{}_3M$ | Milky, uniform, and extremely viscous liquid |
| Silicone Compound No. 3 | $MD_{72}D^{R*31}{}_9D^{R*22}{}_3M$ | Milky and uniform gum |
| Silicone Compound No. 4 | $MD_{72}D^{R*11}{}_3D^{R*31}{}_6D^{R*22}{}_3M$ | Brownish gray-white gum |

TABLE 1-continued

| Silicone Compound | Average compositional formula | Property |
|---|---|---|
| Mixture containing Silicone Compound No. 5 | $MD_{400}D^{R*11}{}_{2}D^{R*31}{}_{3}D^{R*22}{}_{5}M$ (diluted with dimethylpolysiloxane to a 50% concentration) | Milky and uniform (in the form of a gum) |
| Silicone Compound No. 6 | $MD_{72}D^{R*31}{}_{9}D^{R*24}{}_{3}M$ | Translucent and slightly yellow rubber |
| Silicone Compound No. 7 | $MD_{72}D^{R*11}{}_{3}D^{R*31}{}_{6}D^{R*24}{}_{3}M$ | Translucent and topaz rubber |
| Mixture containing Silicone Compound No. 8 | $MD_{400}D^{R*11}{}_{2}D^{R*31}{}_{3}D^{R*24}{}_{5}M$ (diluted with dimethylpolysiloxane to a 50% concentration) | Translucent, pale yellow, and uniform (in the form of a gum) |
| Silicone Compound RE 1 | $MD_{406}D^{R*21}{}_{4}M$ | Pale yellow topaz, translucent, uniform and viscous liquid |
| Silicone Compound RE 2 | $MD_{72}D^{R*11}{}_{9}D^{R*21}{}_{3}M$ | Pale topaz and translucent liquid |
| Silicone Compound RE 3 | $MD_{72}D^{R*11}{}_{9}D^{R*22}{}_{3}M$ | Gray gum (non-uniformity and partial phase separation) |
| Silicone Compound RE 4 | $MD_{61}D^{R*12}{}_{12}D^{R*41}{}_{2}D^{R*25}{}_{1}M$ | Nearly colorless, translucent, and uniform liquid |
| Silicone Compound RE 5 | $MD_{72}D^{R*31}{}_{12}M$ | Pale yellow transparent, and uniform liquid |

In the table, the structures and classifications thereof are described below.

<Long chain alkyl group: $R^{*1}$>
$R^{*11}$=—$C_{10}H_{21}$
$R^{*12}$=—$C_{12}H_{25}$ <Hydrophilic group: $R^{*2}$>
$R^{*21}$=—$C_3H_6OCH_2CH(OH)CH_2OH$
$R^{*22}$=hydrophilic group represented by —$C_3H_6O$—X, wherein X represents a tetraglycerol moiety.
$R^{*23}$=—$C_3H_6O$—X, wherein X represents a diglycerol moiety

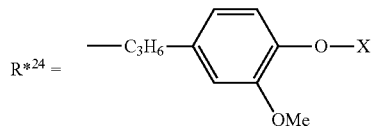

wherein X represents a tetraglycerol moiety.
$R^{*25}$=hydrophilic group represented by —$C_3H_6O$—X, wherein X represents a triglycerol moiety.

<Group having a siloxane dendron structure: $R^{*3}$>
$R^{*31}$=—$C_2H_4Si(OSiMe_3)_3$ <Group having a linear polysiloxane structure: $R^{*4}$>
$R^{*41}$=—$C_2H_4SiMe_2(OSiMe_2)_6OSiMe_3$ Examples 1 to 6 and Comparative Examples 1 to 5

Hair conditioners were prepared with the compositions shown in Table 2 and Table 3. Evaluation thereof was carried out on the basis of the evaluation criteria described below, and effects thereof were quantified.

First, as usage effects during wetting, the following categories were evaluated and pointed.
(A) Sensation during use at the time of applying on hair (smoothness during spreading and light or heavy sensation during spreading): 5 stages of 1 to 5 points
(B) Smoothness at the time of rinsing in running water: 5 stages of 1 to 5 points
(C) Feeling on touch (smoothing property or coating sensation) at the time of drying with a towel: 5 stages of 1 to 5 points Subsequently, as usage effects during drying, the following category was evaluated and pointed.
(D) Conditioning effects after drying (moisturizing sensation or combability with fingers at finishing): 5 stages of 3, 6, 9, 12 and 15 points The total points for usage effects during wetting are 15 points and the total points for usage effects during drying are also 15 points. The results are also shown in Table 2 and Table 3. In the tables, the numerical value described after each component indicates part(s) by weight (mass).

The evaluation methods for the aforementioned sensation during use at the time of applying to hair, smoothness at the time of rinsing in running water, feeling on touch at the time of drying with a towel, and effects of conditioning after drying, as well as evaluation criteria are described below.

(A) Sensation During Use at the Time of Applying to Hair

A commercially available bundle of Chinese hair (manufactured by Beaulax Co., Ltd., 30 cm, 4 g) was subjected to a bleaching treatment for 10 minutes at room temperature, followed by cleansing the bundle with a 10% solution of sodium laureth sulfate. Subsequently, a sample (hair conditioner), in an amount of 1.0 g, was applied thereto. At the time of application, 1.0 g of the sample was put on the palm of a hand, and lightly spread thereon, followed by applying the sample from the roots to the tips of the bundle of hair. Smoothness during spreading and a light or heavy sensation during spreading were evaluated on the basis of the evaluation criteria described below.

5 points: The sample spread well to the tips of hair, superior smoothness was exhibited, and a natural application sensation was provided.

4 points: The sample spread well to the tips of hair, and smoothness was exhibited, but a slight film-foaming sensation was exhibited.

3 points: A good spreading property was exhibited, but a remarkable film-forming sensation was exhibited. Alternatively, a good spreading property was exhibited, but a light feeling on touch was exhibited, and remarkable characteristics were not exhibited.

2 points: The sample spread to the tips of hair, but a slightly heavy sensation was exhibited and poor smoothness was exhibited.

1 point: A heavy sensation and poor spreading property were exhibited, in particular, roughness was exhibited at the tips of hair, and smoothness lacked.

(B) Smoothness in Running Water During Rinsing

The same operations as described in the aforementioned (A) were carried out, followed by rinsing the bundle of hair to which the sample had been applied, with warm running water. Rinsing was carried out by combing the bundle of hair with fingers 10 times, and the feeling on touch at that time was evaluated on the basis of the evaluation criteria described below.

5 points: Natural smoothness continued until the last $10^{th}$ rinsing operation. At the same time, a good coating sensation was also exhibited.

4 points: A smooth feeling on touch was totally exhibited, but a slight film-forming sensation was exhibited from the $8^{th}$ or $9^{th}$ rinsing operation.

3 points: Smoothness was exhibited until the $5^{th}$ rinsing operation, but a film-forming sensation was remarkably exhibited from the $6^{th}$ rinsing operation.

2 points: The sample was cleansed off until the 5$^{th}$ rinsing operation, and the feeling on touch for conditioning weakly remained. Alternatively, poor smoothness was exhibited from the early rinsing operations, and a poor slipping sensation was exhibited at the second half of the rinsing operations. 1 point: Smoothness lacked from the early rinsing operation, and roughness and a frictional sensation were exhibited at the second half of the rinsing operations.

(C) Feeling on Touch During Drying with a Towel

The same operations as those described in the aforementioned (B) smoothness at the time of rinsing in running water were carried out. Subsequently, the wet bundle of hair was wrapped up with a towel to remove moisture. The feeling on touch of the moist bundle of hair (smoothness or a coating sensation) was evaluated on the basis of the evaluation criteria described below.

5 points: Superior smoothness was exhibited over the bundle of hair including the tips of hair.

4 points: Good smoothness was exhibited as a whole and a coating sensation was also exhibited.

3 points: Good smoothness was exhibited at almost all parts of the bundle of hair, but at the tips of hair a slightly frictional sensation was exhibited. Alternatively, slight smoothness was exhibited as a whole, but this was not remarkable.

2 points: A frictional sensation at the tips of hair was remarkably exhibited. Alternatively, poor smoothness was exhibited, and a heavy film-forming sensation was exhibited as a whole.

1 point: Poor smoothness was exhibited, and a frictional sensation was strongly exhibited.

(D) Conditioning Effects after Drying

The same operations as those described in the aforementioned (C) feeling on touch at the time of drying with a towel were carried out. Subsequently, the bundle of hair was completely dried with a drier, and conditioning effects (moisturizing sensation and combability with fingers of the dried hair) were evaluated on the basis of the evaluation criteria described below.

15 points: The bundle of hair possessed a moisturizing sensation as a whole, and superior combability with fingers was exhibited.

12 points: Superior combability with fingers was exhibited over the bundle of hair.

9 points: Good combability with fingers was exhibited at almost all parts of the bundle of hair, but a frictional sensation was partially exhibited.

6 points: Poor smoothness tended to be exhibited as a whole, and slightly poor combability with fingers was exhibited.

3 points: Poor combability was clearly exhibited, and scratch or a frictional sensation was strongly exhibited.

TABLE 2

| | | Example | | | | | |
|---|---|---|---|---|---|---|---|
| No. | Component | 1 | 2 | 3 | 4 | 5 | 6 |
| 1 | Cetanol | 5.6 | 5.6 | 5.6 | 5.6 | 5.6 | 5.6 |
| 2 | Stearyltrimonium chloride | 1.5 | 1.5 | 1.5 | 1.5 | 1.5 | 1.5 |
| 3 | Behentrimonium chloride | 0.8 | 0.8 | 0.8 | 0.8 | 0.8 | 0.8 |
| 4 | Mineral oil | 1.0 | 1.0 | 1.0 | 1.0 | 1.0 | 1.0 |
| 5 | Decamethylcyclopentasiloxane | 2.0 | 2.0 | 2.0 | 2.0 | 2.0 | 2.0 |
| 6 | Dimethylpolysiloaxne, 2 cs | 0.5 | 0.5 | 0.5 | — | 0.5 | 0.5 |
| 7 | Dimethylpolysiloxane, 5,000 cs | 1.0 | 1.0 | 1.0 | 1.0 | 1.0 | 1.0 |
| 8 | Phenyltrimethicone | 2.0 | 2.0 | 2.0 | 2.0 | 2.0 | 2.0 |
| 9 | Silicone Compound No. 2 | 0.5 | — | — | — | — | — |
| 10 | Silicone Compound No. 3 | — | 0.5 | — | — | — | — |
| 11 | Silicone Compound No. 4 | — | — | 0.5 | — | — | — |
| 12 | Silicone Compound No. 5 | — | — | — | 1.0 | — | — |
| 13 | Silicone Compound No. 6 | — | — | — | — | 0.5 | — |
| 14 | Silicone Compound No. 7 | — | — | — | — | — | 0.5 |
| 20 | Methylisothiazolinone | 0.1 | 0.1 | 0.1 | 0.1 | 0.1 | 0.1 |
| 21 | EDTA-2Na | 0.1 | 0.1 | 0.1 | 0.1 | 0.1 | 0.1 |
| 22 | Purified water | 82.9 | 82.9 | 82.9 | 82.9 | 82.9 | 82.9 |
| | Total number of parts | 100.0 | 100.0 | 100.0 | 100.0 | 100.0 | 100.0 |

| | Evaluation category | Evaluation results (points) | | | | | |
|---|---|---|---|---|---|---|---|
| WET | Sensation during use, at the time of applying | 4 | 4 | 3 | 5 | 3 | 3 |
| | Smoothness during rinsing in running water | 3 | 3 | 3 | 5 | 4 | 3 |
| | Feeling on touch during drying with a towel | 4 | 3 | 4 | 5 | 4 | 4 |
| DRY | Conditioning effects after drying | 9 | 9 | 12 | 15 | 9 | 12 |
| | Total points | 20 | 19 | 22 | 30 | 20 | 22 |

TABLE 3

| | | Comparative Example | | | | |
|---|---|---|---|---|---|---|
| No. | Component | 1 | 2 | 3 | 4 | 5 |
| 1 | Cetanol | 5.6 | 5.6 | 5.6 | 5.6 | 5.6 |
| 2 | Stearyltrimonium chloride | 1.5 | 1.5 | 1.5 | 1.5 | 1.5 |
| 3 | Behentrimonium chloride | 0.8 | 0.8 | 0.8 | 0.8 | 0.8 |

TABLE 3-continued

| | | Comparative Example | | | | |
|---|---|---|---|---|---|---|
| No. | Component | 1 | 2 | 3 | 4 | 5 |
| 4 | Mineral oil | 1.0 | 1.0 | 1.0 | 1.0 | 1.0 |
| 5 | Decamethylcyclopentasiloxane | 2.0 | 2.0 | 2.0 | 2.0 | 2.0 |
| 6 | Dimethylpolysiloaxne, 2 cs | 0.5 | 0.5 | 0.5 | 0.5 | 0.5 |
| 7 | Dimethylpolysiloxane, 5,000 cs | 1.0 | 1.0 | 1.0 | 1.0 | 1.0 |
| 8 | Phenyltrimethicone | 2.0 | 2.0 | 2.0 | 2.0 | 2.0 |
| 15 | Silicone Compound RE 1 | 0.5 | — | — | — | — |
| 16 | Silicone Compound RE 2 | — | 0.5 | — | — | — |
| 17 | Silicone Compound RE 3 | — | — | 0.5 | — | — |
| 18 | Silicone Compound RE 4 | — | — | — | 0.5 | — |
| 19 | Silicone Compound RE 5 | — | — | — | — | 0.5 |
| 20 | Methylisothiazolinone | 0.1 | 0.1 | 0.1 | 0.1 | 0.1 |
| 21 | EDTA-2Na | 0.1 | 0.1 | 0.1 | 0.1 | 0.1 |
| 22 | Purified water | 82.9 | 82.9 | 82.9 | 82.9 | 82.9 |
| | Total number of parts | 100.0 | 100.0 | 100.0 | 100.0 | 100.0 |
| | Evaluation category | Evaluation results (points) | | | | |
| WET | Sensation during use, at the time of applying | 3 | 3 | 3 | 3 | 3 |
| | Smoothness during rinsing in running water | 2 | 3 | 4 | 2 | 1 |
| | Feeling on touch during drying with a towel | 2 | 3 | 3 | 2 | 1 |
| DRY | Conditioning effects after drying | 3 | 3 | 6 | 3 | 6 |
| | Total points | 10 | 12 | 16 | 10 | 11 |

Preparation Method of Hair Conditioner
(1) Components No. 1 to No. 19 were placed in a beaker with a volume of 200 mL, the mixture was heated and dissolved at 80° C. while stirring with a propeller mixer.
(2) Separately, components No. 21 and No. 22 were heated and dissolved at 80° C.
(3) The mixture obtained in the aforementioned (2) was added to the mixture obtained in the aforementioned (1) while stirring, to emulsify the mixtures.
(4) The emulsion obtained in the aforementioned (3) was cooled while stirring, and component No. 20 was added thereto at 40° C. or less.

The hair conditioners of the present invention were superior with respect to conventional hair conditioners using a (poly)glycerol-modified silicone in view of both usage effects during WET, represented by (A) sensation during use at the time of applying to hair (spreading smoothness and lightness or heaviness); (B) smoothness at the time of rinsing in running water; and (C) feeling on touch at the time of drying with a towel (smoothing property and coating sensation), and usage effects during DRY, represented by (D) conditioning effects after drying (moisturizing sensation and combability with fingers).

Examples 7 to 9 and Comparative Examples 6 to 8

Shampoos were prepared with the compositions shown in Table 4, and evaluated in accordance with the evaluation criteria described below. The effects were quantified.
First, as cleansing effects, the following category was evaluated and pointed.
(A) Foam quality and foaming property
  5 stages of 1 to 5 points
As usage effects at the time of WET, the following categories were evaluated and pointed.

(B) Smoothness and shampooed sensation in the state of wet hair after rinsing hair: 5 stages of 1 to 5 points
(C) Feeling on touch during drying hair with a towel (natural smoothness with a degree close to healthy hair without damage): 5 stages of 1 to 5 points
Subsequently, as usage effects at the time of DRY, the following category was evaluated and pointed.
(D) Conditioning effects after drying (moisturizing sensation, combability with fingers at finishing, lightness or heaviness): 5 stages of 3, 6, 9, 12 and 15 points
The total points at the time of WET are 15 points and the total points at the time of DRY are also 15 points. The results are also shown in Table 4. In the table, the numerical value described after each component indicates part(s) by weight (mass).

The methods for evaluating the aforementioned foam quality and foaming property, smoothness and a shampooed sensation in the state of wet hair after rinsing hair, feeling on touch during drying hair with a towel, and conditioning effects after drying, as well as evaluation criteria thereof are described below.

(A) Foam Quality and Foaming Property

Warm water was applied to hair to sufficiently contain moisture in hair. Subsequently, an appropriate amount (q.s.) of a shampoo composition of the present invention (the same amount as that which a panelist usually used in accordance with the length of hair of the panelist) was applied to hair with hands and shampooing was carried out by sufficiently applying the shampoo composition over the hair. At this time, the speed of foaming and foam quantity, as well as the fine texture of foam and foam uniformity were evaluated.

5 points: A superior foaming property was exhibited, superior foam quantity such as creamy and uniform foam with a fine texture was obtained, and a good feeling on touch was exhibited.
4 points: A good foaming property was exhibited, and good foam quantity such as uniform foam with a fine texture was obtained.
3 points: A normal foaming property was exhibited, and a normal foam texture and normal foam uniformity were obtained.
2 points: A normal foaming property was exhibited, but a slightly poor foam texture and slightly poor foam uniformity were obtained.
1 point: A poor foaming property and a coarse foam quality were exhibited, and foam quickly disappeared.

(B) Smoothness and a Shampooed Sensation in the State of Wet Hair after Rinsing Hair The same operations as those described in the aforementioned (A) foam quality and foaming property were carried out. Subsequently, the shampooed hair was rinsed with warm running water by showering. Rinsing was carried out by rinsing off the shampoo by combining with fingers 10 times. The feeling on touch of the hair and a shampooed sensation (refreshing sensation by means of cleansing off hair) at the time of completion of the aforementioned rinsing operations 10 times were evaluated.

5 points: Appropriately natural smoothness without an uncomfortable feeling on hair was exhibited, and the level of satisfaction of the shampooed sensation was also increased.
4 points: A slight film-foaming sensation was exhibited on the hair, but appropriate smoothness was exhibited, and the level of satisfaction of the shampooed sensation was also increased.

3 points: A film-forming sensation on the hair and poor smoothness were exhibited, but the level of satisfaction of the shampooed sensation was increased.

2 points: Poor combability with fingers and a frictional sensation were exhibited. As a result, the level of satisfaction of the shampooed sensation was slightly reduced.

1 point: A strong frictional sensation such as a sensation scratched by fingers was exhibited, and thereby, the level of satisfaction of the shampooed sensation was offset.

(C) Feeling on Touch During Drying with a Towel

The same operations as those described in the aforementioned (B) smoothness and a shampooed sensation in the state of wet hair after rinsing hair were carried out. Subsequently, the wet hair was wrapped up with a towel to remove moisture. The feeling on touch of the moist bundle of hair (natural smoothness with a degree close to healthy hair without damage) was evaluated on the basis of the evaluation criteria described below.

5 points: Superior smoothness was exhibited over hair including the tips of hair.

4 points: Good smoothness was exhibited as a whole and a coating sensation was also exhibited.

(D) Conditioning Effects after Drying

The same operations as those described in the aforementioned (C) feeling on touch at the time of drying with a towel were carried out. Subsequently, the hair was completely dried with a drier, and conditioning effects (moisturizing sensation and combability with fingers of the dried hair, as well as lightness and heaviness) were evaluated on the basis of the evaluation criteria described below.

15 points: The hair possessed a moisturizing sensation as a whole, and a refreshing light sensation and natural combability with fingers were exhibited.

12 points: The hair possessed a moisturizing sensation as a whole and natural combability with fingers was exhibited over the hair.

9 points: A moisturizing sensation was exhibited as a whole, and normal combability with fingers was also exhibited.

6 points: A poor moisturizing sensation was exhibited, and slightly poor combability with fingers was exhibited.

3 points: Rough hair was exhibited as a whole, poor combability was also exhibited, and a scratch sensation was exhibited.

TABLE 4

| No. | Component | Ex. 7 | Ex. 8 | Ex. 9 | Comp. Ex. 6 | Comp. Ex. 7 | Comp. Ex. 8 |
|---|---|---|---|---|---|---|---|
| 1 | Sodium POE(2) lauryl ether aulfate (70 wt % aqueous solution) | 17.86 | 17.86 | 17.86 | 17.86 | 17.86 | 17.86 |
| 2 | Cocamidopropylbetaine (30 wt % aqueous solution) | 8.33 | 8.33 | 8.33 | 8.33 | 8.33 | 8.33 |
| 3 | Cetanol | 0.5 | 0.5 | 0.5 | 0.3 | 0.5 | 0.5 |
| 4 | Cationated cellulose (2 wt % aqueous solution) | 25.0 | 25.0 | 25.0 | 25.0 | 25.0 | 25.0 |
| 5 | Cationated guar gum | 0.05 | 0.05 | 0.05 | 0.05 | 0.05 | 0.05 |
| 6 | Copolymer-type cationic polymer of dimethyldiallylammonium halide and acrylamide (9 wt % aqueous solution) | 1.67 | 1.67 | 1.67 | 1.67 | 1.67 | 1.67 |
| 7 | Sodium benzoate | 0.3 | 0.3 | 0.3 | 0.3 | 0.3 | 0.3 |
| 8 | Glycol distearate | 1.0 | 1.0 | 1.0 | 1.0 | 1.0 | 1.0 |
| 9 | O/W emulsion*[1] obtained by emulsifying a mixture of Silicone Compound No. 1 and dimethylpolysiloxane (2 cs) | 4.0 | — | — | — | — | — |
| 10 | O/W emulsion*[1] obtained by emulsifying a mixture of Silicone Compound No. 5 and dimethylpolysiloxane (2 cs) | — | 4.0 | — | — | — | — |
| 11 | O/W emulsion*[1] obtained by emulsifying a mixture of Silicone Compound No. 8 and dimethylpolysiloxane (2 cs) | — | — | 4.0 | — | — | — |
| 12 | O/W emulsion*[1] for comparison obtained by emulsifying a mixture of Silicone Compound RE 3 and dimethylpolysiloxane (2 cs) | — | — | — | 4.0 | — | — |
| 13 | O/W emulsion*[1] for comparison obtained by emulsifying a mixture of Silicone Compound RE 4 and dimethylpolysiloxane (2 cs) | — | — | — | — | 4.0 | — |
| 14 | Citric acid | 0.05 | 0.05 | 0.05 | 0.05 | 0.05 | 0.05 |
| 15 | Purified water | 41.24 | 41.24 | 41.24 | 41.24 | 41.24 | 41.24 |
|  | Total number of parts | 100.0 | 100.0 | 100.0 | 100.0 | 100.0 | 100.0 |
|  | Evaluation category | \multicolumn{6}{c}{Evaluation results (points)} | | | | | |
| WET | Foam quality and foaming property | 5 | 5 | 5 | 3 | 4 | 5 |
|  | Smoothness of wet hair after rinsing | 5 | 5 | 4.5 | 2 | 1 | 1 |
|  | Feeling on touch during drying with a towel | 5 | 5 | 4.5 | 3 | 1 | 1 |
| DRY | Conditioning effects after drying | 12 | 15 | 12 | 9 | 6 | 3 |
| Total points | | 27 | 30 | 26 | 17 | 12 | 10 |

Note

*O/W emulsion comprising 60% by weight (mass) of a liquid obtained by mixing and uniforming a silicone compound (10 parts) and a dimethylpolysiloxane (2 cs) (90 parts), produced by emulsifying the formulation shown in Table 5 described below.

3 points: Good smoothness was exhibited at almost all parts of the hair, but at the tips of hair a slightly frictional sensation was exhibited. Alternatively, slight smoothness was exhibited as a whole, but this was not remarkable.

2 points: Poor smoothness was exhibited as a whole. Alternatively, a frictional sensation at the tips of hair was remarkably exhibited.

1 point: Poor smoothness was exhibited, and a frictional sensation was strongly exhibited.

TABLE 5

| Name of raw material | Type of raw material | Parts by weight (mass) |
|---|---|---|
| Mixture of silicone compound and dimethylpolysiloxane (2 cs) (10:90) | Oil agent | 60.0 |
| POE (4) lauryl ether | Nonionic emulsifier | 2.1 |

TABLE 5-continued

| Name of raw material | Type of raw material | Parts by weight (mass) |
|---|---|---|
| POE (25) lauryl ether | Nonionic emulsifier | 2.9 |
| Cetyltrimethylammonium chloride (30 wt % aqueous solution) | Cationic emulsifier | 0.5 |
| Sodium benzoate | Preservative | 0.5 |
| Citric acid | pH adjustor | 0.2 |
| Purified water | Water | 33.8 |
| Total | | 100.0 |

Preparation Method

Preparation Method for a Shampoo (1) Component No. 1 to Component No. 3, Component No. 7, Component No. 8, and Component No. 15 were placed in a beaker with a volume of 200 mL. The mixture was stirred by means of a propeller mixer and completely dissolved at 70° C.
(2) Components No. 4 to No. 6 were added to the solution obtained in the aforementioned step (1) while the temperature thereof was maintained at 70° C., and the mixture were completely dissolved.
(3) The solution obtained in the aforementioned step (2) was cooled under stirring, and Component No. 9 to Component No. 13 were added thereto at 55° C.
(4) The mixture was further cooled to room temperature, and Component No. 14 was added thereto under stirring.

It was verified that the shampoos of the present invention were superior, as compared with comparative shampoos using other polyglycerol-modified silicones used in Comparative Experiments, in view of all categories of (A) foam quality and foaming property; usage effects at the time of WET, represented by (B) smoothness and a shampooed sensation in the state of wet hair after rinsing hair, and (C) feeling on touch during drying hair with a towel (natural smoothness with a degree close to healthy hair without damage); and usage effects at the time of DRY, represented by (D) conditioning effects after drying (moisturizing sensation, combability with fingers at finishing, lightness or heaviness).

Examples 10 and 11 and Comparative Examples 9 and 10

Hair creams (setting type) were prepared with the compositions shown in Table 6. Evaluation thereof was carried out on the basis of the evaluation criteria described below, and effects thereof were quantified.

First, as usage effects from applying to drying, the following categories were evaluated and pointed.

(A) Reduction of stickiness after applying to hair and until drying: 3 stages of 1, 3, and 5;
(B) Smoothness after applying to hair and until drying: 3 stages of 1, 3, and 5.

As usage effects after finishing, the following categories were evaluated and pointed.

(C) Retention ability of setting: 3 stages of 1, 3, and 5;
(D) Reduction of a rough sensation of hair of which setting had been finished: 3 stages of 1, 3, and 5.

The total points during use are 10 points and the total points at the time of finishing hair-setting are also 10 points. The results are also shown in Table 6. In the table, the numerical value described after each component indicates part(s) by weight (mass).

The evaluation methods and evaluation criteria of the aforementioned reduction of stickiness after applying to hair to drying, smoothness after applying to hair to drying, retention ability of setting, and reduction of a rough sensation of set hair are described below.

(A) Reduction of Stickiness after Applying to Hair to Drying

A commercially available bundle of Chinese hair (manufactured by Beaulax Co., Ltd., 30 cm, 4 g) was washed with a 10% solution of sodium laureth sulfate. Subsequently, 1.0 g of a sample (hair cream) was put on the palm of a hand, and lightly spread thereon, followed by applying the sample from the roots to the tips of the bundle of hair. The style of the bundle of hair was adjusted, and stickiness was evaluated until the hair was dried.

5 points: No stickiness was felt from applying to drying.
3 points: No stickiness was felt at the time of applying, but stickiness was slightly felt at the time of drying.
1 point: Stickiness was slightly felt at the time of applying, and stickiness was clearly felt at the time of drying.

(B) Smoothness after Applying Until Drying

The same operations as described in the aforementioned (A) were carried out, a sample was applied to the bundle of hair, and style of the hair was adjusted with a comb. Smoothness until the bundle of hair was dried was evaluated.

5 points: Superior smooth combability was exhibited.
3 points: Smooth combability was normal.
1 point: Poor combability was exhibited with scratching.

(C) Retention Ability of Setting

A bundle of hair having a length of 25 cm and a weight of 2 g was moisturized with water, and 0.5 g of a sample was applied thereon. The bundle of hair was rolled on a rod having a diameter of 15 mm and naturally dried. After drying, the rod was removed from the curled bundle of hair. The curled bundle of hair was hung for one hour in a thermo-hygrostat chamber (28° C., 90% RH). Subsequently, the length of the curled hair was measured. Retention ability of setting was calculated in accordance with the following equation with the length ($l_1$) of curled hair immediately after the rod was removed from the hair and the length ($l_2$) of the hair which was allowed to stand for one hour, and evaluated.

$$\text{Retention ability of setting} = \{(25-l_2)/(25-l_1)\} \times 100(\%)$$

5 points: retention ability of setting=90 to 100%
3 points: retention ability of setting=67 to 89%
1 point: retention ability of setting=34 to 66%

(D) Reduction of a Rough Sensation of Set Hair

The feeling on touch of the bundle of hair which had been dried in the aforementioned (A) was evaluated on the basis of the evaluation criteria described below.

5 points: Rough and coarse hardness was not exhibited, natural smoothness was possessed, and a good styling sensation was obtained.
3 points: A rough and hard feeling on touch was slightly exhibited, but at the same time a slightly smooth sensation was exhibited.
1 point: Rough and coarse hardness and a scratching sensation were exhibited.

TABLE 6

| No. | Component | Ex. 10 10 | Ex. 11 11 | Comp. Ex. 9 9 | Comp. Ex. 10 10 |
|---|---|---|---|---|---|
| 1 | Carrageenan | 1.0 | 1.0 | 1.0 | 1.0 |
| 2 | POE (60) hardened castor oil | 1.0 | 1.0 | 1.0 | 1.0 |
| 3 | Carboxyvinyl polymer | 0.6 | 0.6 | 0.6 | 0.6 |
| 4 | Triethanolamine | q.s. (pH = 7.5) | q.s. (pH = 7.5) | q.s. (pH = 7.5) | q.s. (pH = 7.5) |
| 5 | Glycerol | 2.0 | 2.0 | 2.0 | 2.0 |
| 6 | Perfume | q.s. | q.s. | q.s. | q.s. |
| 7 | Octyl methoxycinnamate | 0.1 | 0.1 | 0.1 | 0.1 |
| 8 | Ethanol | 25.0 | 25.0 | 25.0 | 25.0 |
| 9 | Purified water | 58 | 58 | 58 | 63 |
| 10 | Amphoteric polymer: Copolymer of N-methacryloyloxydiethyl-N,N-dimethylaminoethyl-alpha-N-methylcarboxybetaine and methacrylic acid alkyl ester | 3.0 | 3.0 | 3.0 | 3.0 |
| 11 | Anionic polymer: Alkyl acrylate copolymer TEA (30% ethanol solution) | 1.0 | 1.0 | 1.0 | 1.0 |
| 12 | O/W emulsion**) obtained by emulsifying a mixture of Silicone Compound No. 5 and dimethylpolysiloxane (2 cs) | 8.0 | — | — | — |
| 13 | O/W emulsion**) obtained by emulsifying a mixture of Silicone Compound No. 8 and dimethylpolysiloxane (2 cs) | — | 8.0 | — | — |
| 14 | O/W emulsion**) obtained by emulsifying a mixture of Silicone Compound RE 4 and dimethylpolysiloxane (2 cs) | — | — | 8.0 | — |
| Total number of parts | | 100 | 100 | 100 | 100 |

| Evaluation category | | Evaluation results (points) | | | |
|---|---|---|---|---|---|
| During use | Reduction of stickiness after applying and until drying | 3 | 5 | 3 | 1 |
| | Smoothness after applying and until drying | 5 | 5 | 3 | 1 |
| Finishing | Retention property of set hair | 5 | 5 | 3 | 5 |
| | Reduction of rough sensation of finally styled hair | 5 | 5 | 3 | 1 |
| Total points | | 18 | 20 | 12 | 8 |

Note
**O/W emulsion which contains 30% by weight (mass) of a liquid produced by mixing a silicone compound (10 parts) with a dimethylpolysiloxane, 2 cs (90 parts), and uniforming the mixture, and which is produced by emulsifying the formulation shown by the following Table 7.

TABLE 7

| Name of raw material | Type of raw material | Parts by weight (mass) |
|---|---|---|
| Mixture of silicone compound and dimethylpolysiloxane (2 cs) (10:90) | Oil agent | 30.0 |
| Polyoxyethylene (4) alkyl (12-15) ether phosphoric acid | Anionic emulsifier | 1.7 |
| POE (23) lauryl ether | Nonionic emulsifier | 3.3 |
| Ethanol | Dispersant of paraben | 2.0 |
| Propylparaben | Preservative | 0.05 |
| Methylparaben | Preservative | 0.15 |
| Triethanolamine | pH adjustor | 0.17 |
| Purified water | Water | 62.63 |
| Total | | 100.0 |

Preparation Method for a Cream for Use on Hair (Setting Type)

(1) Half of Component No. 9 was placed in a beaker with a volume of 200 mL, and Components No. 1 to No. 3 and No. 5 were added thereto. The mixture was stirred by means of a propeller mixer and uniformly dissolved.

(2) Components No. 4 and No. 6 to No. 8 were placed in another container, and they are uniformly dissolved.

(3) The remaining amount of Component No. 9 was gradually added to the solution obtained in the aforementioned step (2), which was being stirred, and thereby, a uniform dispersion was formed.

(4) Components No. 10 and No. 11 were gradually added to the dispersion obtained in the aforementioned step (3), which was being stirred. Thereby, a uniform viscous liquid was obtained.

(5) Components No. 12 to No. 14 were gradually added to the liquid obtained in the aforementioned step (4), which was being stirred. Thereby, a uniform cream was produced.

It was verified that the creams for use on hair (setting type) were superior, as compared with comparative creams for use on hair (setting type) using other polyglycerol-modified silicones used in Comparative Experiments, in view of both feeling on touch during use represented by (A) reduced stickiness after application and until drying, and (B) smoothness after application and until drying; and styling effects after finishing represented by (C) retention property of set hair, and (D) reduction of a rough sensation after finishing setting.

Hereinafter, particular formulations of cosmetics for hair of the present invention are described as examples of the present invention. It should be understood that the present invention is not restricted thereto. In the series of Formulation Examples, in view of improvement of a feeling on touch to hair, Silicone Compound No. 5 (high polymerization 400) is the most preferred. For this reason, in Formulation Examples, Silicone Compound No. 5 is used. Therefore, it should be understood that Silicone Compound 5 used in Formulation Examples can be replaced with another co-modified silicone according to the present invention (such as the aforementioned Silicone Compound Nos. 1 to 4 and 6 to 8), and a mixture of two or more types of different co-modified silicones according to the present invention can also be used.

Formulation Example 1

Shampoo

The numerical value described after each component indicates part(s) by weight (mass).

| (Components) | |
|---|---|
| 1. Purified water | remainder |
| 2. Polyquaternium-10 | 0.3 |
| 3. EDTA-2Na | 0.1 |
| 4. Glycerol | 1.5 |
| 5. Sodium laureth sulfate (27% aqueous solution) | 30.0 |
| 6. Sodium laureth-6 carboxylate (24% aqueous solution) | 10.0 |
| 7. Cocamidopropylbetaine, NaCl (30% aqueous solution) | 10.0 |
| 8. Polyquaternium-7 | 0.27 |
| 9. Preservatives | q.s. |
| 10. Perfume | q.s. |
| 11. Cocamido MEA | 2.0 |
| 12. Emulsion of Silicone Compound No. 5 (Note) | 0.5 |
| 13. Citric acid | q.s. |

(Note): O/W emulsion obtained by mixing Silicone Compound No. 5 and dimethylpolysiloxane (2 cSt) in a weight (mass) ratio of 1/9, and emulsifying the mixture so that the solid content is 30% by weight (mass).

Preparation Procedure

Step 1: Components 1 to 4 are heated, and subsequently, mixed and dissolved.

Step 2: Components 5 to 7 are added to the composition obtained in Step 1.

Step 3: The composition obtained in Step 2 is cooled, and components 8 to 12 are added thereto. Component 13 is added thereto, if necessary, to adjust the pH.

After Step 3, by further blending an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, and/or a water-soluble silicone oil such as a polyether-modified silicone or the like, or the like, the synergistic effects of respective components can be expected.

Formulation Example 2

Conditioner

The numerical value described after each component indicates part(s) by weight (mass).

| (Components) | |
|---|---|
| 1. Stearyltrimonium chloride | 1.44 |
| 2. Cetyl alcohol | 2.4 |
| 3. Octyl dodecanol | 0.5 |
| 4. Cetyl ethylhexanoate | 0.6 |
| 5. Squalane | 0.2 |
| 6. Purified water | remainder |
| 7. Glycerol | 2.0 |
| 8. Preservatives | q.s. |
| 9. Perfume | q.s. |
| 10. Emulsion of Silicone Compound No. 5 (Note) | 3.0 |
| 11. Citric acid | q.s. |

(Note): O/W emulsion obtained by mixing Silicone Compound No. 5 and dimethylpolysiloxane (2 cSt) in a weight (mass) ratio of 1/9, and emulsifying the mixture so that the solid content is 30% by weight (mass).

Preparation Procedure

Step 1: Components 1 to 5 are heated, and subsequently, mixed and dissolved.

Step 2: Components 6 and 7 are heated, and subsequently, mixed and dissolved.

Step 3: The composition obtained in Step 2 is added to the composition obtained in Step 1 to emulsify the mixture.

Step 4: The composition obtained in Step 3 is cooled, and components 8 to 10 are added thereto. Component 11 is added thereto, if necessary.

After Step 4, by further blending an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, and/or a water-soluble silicone oil such as a polyether-modified silicone or the like, or the like, the synergistic effects of respective components can be expected.

Formulation Example 3

Hair Treatment, Rinse-in Type

The numerical value described after each component indicates part(s) by weight (mass).

| (Components) | |
|---|---|
| 1. Cetyl alcohol | 5.6 |
| 2. Mineral oil | 1.0 |
| 3. Stearyltrimonium chloride | 1.2 |
| 4. Behentrimonium chloride | 0.64 |
| 5. Cyclopentasiloxane | 2.0 |
| 6. Dimethicone (2 cSt) | 1.0 |
| 7. Dimethicone (5,000 cSt) | 1.0 |
| 8. Phenylmethicone | 2.0 |
| 9. Glycerol | 2.0 |
| 10. EDTA-2Na | 0.1 |
| 11. Purified water | remainder |
| 12. Panthenol | 0.1 |
| 13. Tocopherol | 0.04 |
| 14. Lysine HCl | 0.02 |
| 15. Glycine | 0.02 |
| 16. Histidine | 0.02 |
| 17. Silicone Compound No. 5 | 0.5 |
| 18. Preservatives | q.s. |
| 19. Perfume | q.s. |

Preparation Procedure

Step 1: Components 1 to 8 are heated, and subsequently, mixed and dissolved.

Step 2: Components 9 to 11 are heated, and subsequently, mixed and dissolved.

Step 3: The composition obtained in Step 2 is added to the composition obtained in Step 1 to emulsify the mixture.

Step 4: The composition obtained in Step 3 is cooled, and components 12 to 19 are added thereto.

In addition, in Step 1, by further adding a dimethylpolysiloxane (dimethiconol) of which both terminals are capped with dimethylsilanol groups, an amino-modified silicone, an aminopolyether-co-modified silicone or the like, in addition to components 1 to 8, the synergistic effects of respective components can be expected.

Formulation Example 4

Hair Treatment, Leave-on Type

The numerical value described after each component indicates part(s) by weight (mass).

| (Components) | |
|---|---|
| 1. Cetyl alcohol | 4.0 |
| 2. Mineral oil | 1.0 |
| 3. Stearyltrimonium chloride | 1.0 |
| 4. Behentrimonium chloride | 0.2 |
| 5. Cyclopentasiloxane | 1.2 |
| 6. Dimethicone (2 cSt) | 0.6 |
| 7. Dimethicone (5,000 cSt) | 0.6 |
| 8. Phenylmethicone | 1.2 |
| 9. Glycerol | 2.0 |
| 10. EDTA-2Na | 0.1 |
| 11. Purified water | remainder |
| 12. Panthenol | 0.1 |
| 13. Tocopherol | 0.04 |
| 14. Lysin HCl | 0.02 |
| 15. Glycine | 0.02 |
| 16. Histidine | 0.02 |
| 17. Silicone Compound No. 5 | 0.3 |
| 18. Preservatives | q.s. |
| 19. Perfume | q.s. |

Preparation Procedure

Step 1: Components 1 to 8 are heated, and subsequently, mixed and dissolved.
Step 2: Components 9 to 11 are heated, and subsequently, mixed and dissolved.
Step 3: The composition obtained in Step 2 is added to the composition obtained in Step 1 to emulsify the mixture.
Step 4: The composition obtained in Step 3 is cooled, and components 12 to 19 are added thereto.

In addition, in Step 1, by further adding a dimethylpolysiloxane (dimethiconol) of which both terminals are capped with dimethylsilanol groups, an amino-modified silicone, an aminopolyether-co-modified silicone or the like, in addition to components 1 to 8 the synergistic effects of respective components can be expected.

Formulation Example 5

Hair Mist

The numerical value described after each component indicates part(s) by weight (mass).

| (Components) | |
|---|---|
| 1. Purified water | remainder |
| 2. Sorbitol | 0.6 |
| 3. Creatine | 0.2 |
| 4. Urea | 1.0 |
| 5. 1,3-butylene glycol | 2.0 |
| 6. Preservatives | q.s. |
| 7. Ethanol | 15.0 |
| 8. Glycereth-25 PCA isosteate | 0.5 |
| 9. Perfume | q.s. |

-continued

| (Components) | |
|---|---|
| 10. PEG/PPG-30/10 dimethicone, DPG(Note) | 1.0 |
| 11. Silicone Compound No. 5 | 1.0 |
| 12. Bisethoxydiglycol cyclohexanedicarboxylate | 2.0 |
| 13. Hydroxypropyltrimonium starch chloride | 1.0 |

(Note): BY 25-338, manufactured by Dow Corning Toray Co., Ltd.

Preparation Procedure

Step 1: Components 1 to 6 are mixed and dissolved.
Step 2: Components 7 to 10 are mixed and dissolved.
Step 3: The composition obtained in Step 2 is added to the composition obtained in Step 1 to solubilize.
Step 4: Components 11 to 13 are added to the composition obtained in Step 3, and the mixture is mixed and dissolved.

Formulation Example 6

Foam for Use on Hair

The numerical value described after each component indicates part(s) by weight (mass).
Liquid

| (Components) | |
|---|---|
| 1. Copolymer of polyvinylpyrrolidone and vinyl acetate | 5.0 |
| 2. Diethylsulfate salt of copolymer of vinylpyrrolidone and N,N-dimethylaminoethylmethacrylic acid | 0.5 |
| 3. Phenyltrimethicone | 2.0 |
| 4. Silicone Compound No. 5 | 1.0 |
| 5. Ethanol | 12.0 |
| 6. Preservatives | q.s. |
| 7. Perfume | q.s. |
| 8. Purified water | remainder |
| Formulation | |
| 9. liquid | 95.0 |
| 10. Liquid petroleum gas (LPG) | 5.0 |

Preparation Procedure

Step 1: Components 1 to 8 are mixed and dissolved.
Step 2: The composition (Liquid=component 9) obtained in Step 1 is placed in a container (can), and a valve is loaded. Subsequently, component 10 is placed therein.

In addition, in Step 1, a copolymer of acrylate and polytrimethylsiloxy methacrylate (such as FA 4001 CM (30% decamethylcyclopentasiloxane solution), manufactured by Dow Corning Toray Co., Ltd.) may be added as a film-forming agent, in addition to components 1 to 8.

Formulation Example 7

Hair Spray

The numerical value described after each component indicates part(s) by weight (mass).
Liquid:

| (Components) | |
|---|---|
| 1. Ethyl alcohol | remainder |
| 2. Alkanolamine liquid of acrylic resin (active ingredient = 50%) | 7.0 |

-continued

| (Components) | |
|---|---|
| 3. Cetyl alcohol | 0.1 |
| 4. Silicone Compound No. 5 | 0.5 |
| 5. Perfume | q.s. |
| Formulation | |
| 6. Liquid | 50.0 |
| 7. Dimethyl ether | 50.0 |

Preparation Procedure

Step 1: Components 2 to 5 are added to component 1, and the mixture is mixed and dissolved.

Step 2: The composition obtained in Step 1 is filtered.

Step 3: The composition (Liquid=component 6) obtained in Step 2 is placed in a container (can), and a valve is loaded. Subsequently, the container is charged with component 7.

Formulation Example 8

Hair Wax

The numerical value described after each component indicates part(s) by weight (mass).

| (Components) | |
|---|---|
| 1. Diethylhexyl succinate | 10.0 |
| 2. Squalane | 1.0 |
| 3. Shear butter | 1.0 |
| 4. Silicone Compound No. 5 | 2.0 |
| 5. Candelilla wax | 5.5 |
| 6. Microcrystalline wax | 6.0 |
| 7. Carnauba wax | 6.0 |
| 8. Ceteth-6 | 6.0 |
| 9. Ceteth-10 | 6.0 |
| 10. Glyceryl stearate (SE) soap impurities | 1.5 |
| 11. Hydroxystearic acid | 4.5 |
| 12. Purified water | remainder |
| 13. 1,3-butylene glycol | 3.0 |
| 14. Sodium hydroxide | q.s. |
| 15. PEG-90M | q.s. |
| 16. Preservatives | q.s. |

Preparation Procedure

Step 1: Components 1 to 11 are heated, and subsequently, mixed and dissolved.

Step 2: Components 12 to 14 are heated, and subsequently, mixed and dissolved.

Step 3: The composition obtained in Step 2 is added to the composition obtained in Step 1, and the mixture is emulsified.

Step 4: Components 15 and 16 are successively added to the composition obtained in Step 3.

Formulation Example 9

Cream for Use on Hair

The numerical value described after each component indicates part(s) by weight (mass).

| (Components) | |
|---|---|
| 1. Vaseline | 4.0 |
| 2. Cetyl ethylhexanoate | 3.0 |
| 3. Silicone Compound No. 5 (Note) | 2.0 |
| 4. Dimethicone (350 cSt) | 1.0 |
| 5. PEG-40 hydrogenated castor oil | 1.0 |
| 6. Polyacrylamide | 1.0 |
| 7. Purified water | remainder |
| 8. Glycerol | 3.0 |
| 9. Hydroxyethylcellulose | 0.1 |
| 10. Ethanol | 3.0 |
| 11. Preservatives | q.s. |

(Note): Decamethylcyclopentasiloxane solution of Silicone Compound No. 5 (active ingredient = 10% by weight (mass)).

Preparation Procedure

Step 1: Components 1 to 5 are heated, and subsequently, mixed and dissolved.

Step 2: Components 6 to 9 are heated, and subsequently, mixed and dissolved.

Step 3: The composition obtained in Step 2 is added to the composition obtained in Step 1, and the mixture is emulsified.

Step 4: Components 10 and 11 are successively added to the composition obtained in Step 3.

In addition, in Step 1, by further adding a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, in addition to components 1 to 5, the synergistic effects of respective components can be expected.

Formulation Example 10

Lotion for Use on Hair

The numerical value described after each component indicates part(s) by weight (mass).

| (Components) | |
|---|---|
| 1. Carbomer | 0.4 |
| 2. Hydroxyethylcellulose | 0.1 |
| 3. PEG-6 | 1.5 |
| 4. Purified water | remainder |
| 5. Ethanol | 3.5 |
| 6. PEG-40 hydrogenated castor oil | 0.5 |
| 7. Trilaureth-4 phosphate | 0.1 |
| 8. Cetyl ethylhexanoate | 2.0 |
| 9. Emulsion of Silicone Compound No. 5 (Note 1) | 1.2 |
| 10. Emulsion of dimethicone (Note 2) | 2.5 |
| 11. Preservatives | q.s. |
| 12. Sodium hydroxide | q.s. |

(Note 1): O/W emulsion obtained by mixing Silicone Compound No. 5 and dimethylpolysiloxane (2 cSt) in a weight (mass) ratio of 1/9, and emulsifying the mixture so that the solid content is 30% by weight (mass).
(Note 2): FZ-4150 (active ingredient = 30% by weight (mass)), manufactured by Dow Corning Toray Co., Ltd.

Preparation Procedure

Step 1: Components 1 to 4 are heated, and subsequently, mixed and dissolved.

Step 2: Components 5 to 7 are heated, and subsequently, mixed and dissolved.

Step 3: The composition obtained in Step 2 is added to the composition obtained in Step 1, and the mixture is emulsified.

Step 4: Components 8 to 12 are added to the composition obtained in Step 3.

In addition, in Step 4, by adding an emulsion such as a dimethylsilicone, a dimethylpolysiloxane (dimethiconol) of which both terminals are capped with dimethylsilanol groups, a phenyl-modified silicone, an amino-modified silicone, an aminopolyether-co-modified silicone or the like, an aqueous dispersion of silicone elastomer powders, a water-soluble silicone oil such as a polyether-modified silicone or the like, or the like, in addition to components 8 to 12, the synergistic effects of respective components can be expected.

Formulation Example 11

Oil for Use on Hair

The numerical value described after each component indicates part(s) by weight (mass).

| (Components) | |
|---|---|
| 1. Cyclopentasiloxane solution of dimethicone (Note) | remainder |
| 2. Silicone Compound No. 5 | 3.0 |
| 3. Dimethicone (350 cSt) | 2.0 |
| 4. Decamethylcyclopentasiloxane | 28.0 |

(Note): BY11-003, manufactured by Dow Corning Toray Co., Ltd.

Preparation Procedure

Step 1: Components 1 to 4 are appropriately heated, and subsequently, mixed and dissolved.

Formulation Example 12

Hair Color of Oxidation Type

The numerical value described after each component indicates part(s) by weight (mass).
First Agent

| (Components) | |
|---|---|
| 1. Steareth-2 | 3.0 |
| 2. Steareth-21 | 2.0 |
| 3. Stearyl PPG-15 | 5.0 |
| 4. Cetostearyl alcohol | 4.0 |
| 5. Behenyl alcohol | 2.0 |
| 6. Silicone Compound No. 5 | 2.0 |
| 7. Behenyltrimethylammonium chloride | 0.8 |
| 8. Purified water | remainder |
| 9. EDTA-2Na | 0.5 |
| 10. Anhydrous sodium sulfite | 0.5 |
| 11. Sodium ascorbate | 0.1 |
| 12. 1,3-butylene glycol | 3.0 |
| 13. p-phenylenediamine | 0.25 |
| 14. p-aminophenol | 0.1 |
| 15. m-aminophenol | 0.05 |
| 16. Polyquaternium-39 | 0.3 |
| 17. Ammonium hydrogen carbonate | 2.0 |
| 18. Strong aqueous ammonia | 5.0 |

Preparation Procedure

Step 1: Components 1 to 7 are heated, and subsequently, mixed and dissolved.

Step 2: Components 8 to 15 are heated, and subsequently, mixed and dissolved.

Step 3: The composition obtained in Step 1 is added to the composition obtained in Step 2, and the mixture is emulsified.

Step 4: Components 16 to 18 are successively added to the composition obtained in Step 3.

Second Agent

| (Components) | |
|---|---|
| 1. Cetostearyl alcohol | 4.5 |
| 2. Sodium laurylsulfate | 0.5 |
| 3. Preservatives | q.s. |
| 4. Etidronic acid | 0.1 |
| 5. Disodium hydrogen phosphate | 0.3 |
| 6. Purified water | remainder |
| 7. Hydrogen peroxide solution (35% aqueous solution) | 17.14 |
| 8. Phosphoric acid | q.s. |

Preparation Procedure

Step 1: Component 1 is heated and dissolved.

Step 2: Components 2 to 6 are heated, and subsequently, mixed and dissolved.

Step 3: The component obtained in Step 1 is added to the composition obtained in Step 2, and the mixture is emulsified.

Step 4: The composition obtained in Step 3 is cooled. Component 7 is added thereto and component 8 is added thereto, if necessary.

Formulation Example 13

Hair Manicure

The numerical value described after each component indicates part(s) by weight (mass).

| (Components) | |
|---|---|
| 1. Black No. 401 | 0.4 |
| 2. Violet No. 401 | 0.1 |
| 3. Orange No. 205 | 0.3 |
| 4. Benzyl alcohol | 5.0 |
| 5. Citric acid | 0.5 |
| 6. Hydroxyethylcellulose | 2.0 |
| 7. Stearyltrimethylammonium chloride | 0.5 |
| 8. PEG-40 hydrogenated castor oil | 0.5 |
| 9. Silicone Compound No. 5 | 1.0 |
| 10. Ethanol | 10.0 |
| 11. Preservatives | q.s. |
| 12. Perfume | q.s. |
| 13. Purified water | remainder |
| 14. Sodium citrate | q.s. |

Preparation Procedure

Step 1: Components 1 to 13 are mixed and dissolved.

Step 2: Component 14 is added to the composition obtained in Step 1, and thereby, the pH of the mixture is adjusted.

Formulation Example 14

Preparation for Permanent Waving

The numerical value described after each component indicates part(s) by weight (mass).

First Agent

| (Components) | |
|---|---|
| 1. EDTA-2Na | 0.1 |
| 2. Etidronic acid | 0.1 |
| 3. Preservatives | q.s. |
| 4. Purified water | remainder |
| 5. PEG-40 hydrogenated castor oil | 0.6 |
| 6. Perfume | 0.3 |
| 7. Ammonium thioglycolate (50% aqueous solution) | 13.0 |
| 8. Strong aqueous ammonia | 1.0 |
| 9. Monoethanolamine | 1.2 |
| 10. Ammonium hydrogen carbonate | 2.0 |
| 11. Emulsion of Silicone Compound No. 5 (Note) | 0.5 |
| 12. Phosphoric acid | q.s. |

Preparation Procedure

Step 1: Components 1 to 4 are appropriately heated, and subsequently, mixed and dissolved.

Step 2: Components 5 and 6 are heated, and subsequently, mixed and dissolved.

Step 3: The composition obtained in Step 2 is added to the composition obtained in Step 1.

Step 4: Components 7 to 11 are successively added to the composition obtained in Step 3. Component 12 is added thereto, if necessary.

Second Agent

| (Components) | |
|---|---|
| 1. Polyquaternium-10 | 0.4 |
| 2. EDTA-2Na | 0.1 |
| 3. Preservatives | q.s. |
| 4. Sodium dihydrogen phosphate | 0.05 |
| 5. Disodium hydrogen phosphate | 0.5 |
| 6. Purified water | remainder |
| 7. Sodium bromate | 8.0 |
| 8. pH adjustor | q.s. |

Note:
O/W emulsion obtained by mixing Silicone Compound No. 1 and dimethylpolysiloxane (2 cSt) in a weight (mass) ratio of 1/9, and emulsifying the mixture so that the solid content is 30% by weight (mass).

Preparation Procedure

Step 1: Components 1 to 6 are appropriately heated, and subsequently, mixed and dissolved.

Step 2: Component 7 is added to the composition obtained in Step 1. Component 8 is added thereto, if necessary.

The invention claimed is:

1. A cosmetic for hair comprising (A) a co-modified organopolysiloxane represented by the following general formula (1):

$$R^1_a L^1_b Q_c SiO_{(4-a-b-c)/2} \quad (1)$$

wherein $R^1$ represents a monovalent organic group, with the proviso that L and Q are excluded therefrom, a hydrogen atom or a hydroxyl group;

$L^1$ represents a silylalkyl group having a siloxane dendron structure, in the case of i=1, represented by the following general formula (2):

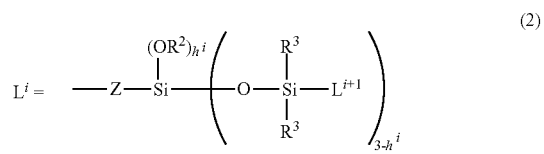

wherein $R^2$ represents a substituted or non-substituted, and linear or branched monovalent hydrocarbon group having 1 to 30 carbon atoms;

$R^3$ independently represents an alkyl group having 1 to 6 carbon atoms or a phenyl group;

Z represents a divalent organic group;

i specifies a number of generations of said silylalkyl group, represented by $L^i$, in the case in which the number of generations of said silylalkyl group, which is the number of repetitions of said silylalkyl group, is k, i is an integer ranging from 1 to k, and the number of generations k is an integer ranging from 1 to 10;

$L^{i+1}$ is said silylalkyl group in the case of i<k, and $L^{i+1}$ is $R^3$ in the case of i=k; and $h^i$ is a number ranging from 0 to 3;

Q represents a hydrophilic group which binds to a silicon atom via a linking group with two or more valances and comprises at least one hydrophilic unit selected from hydrophilic units represented by the following structural formulae (3-1) to (3-4):

$$—C_rH_{2r}—O— \quad (3\text{-}1)$$

wherein r is a number ranging from 1 to 6,

wherein W represents a hydrogen atom or an alkyl group having 1 to 20 carbon atoms,

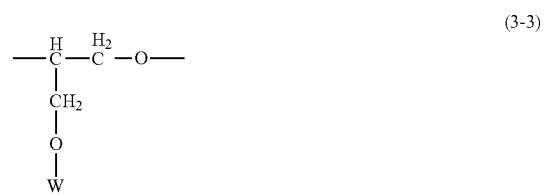

wherein W represents the same group as defined above, and

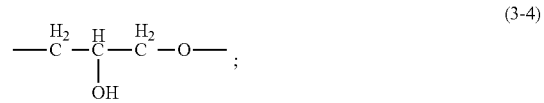

and
each of a, b and c is independently a number having the following range: $1.0 \leq a \leq 2.5$, $0.0001 \leq b \leq 1.5$, and $0.0001 \leq c \leq 1.5$.

2. The cosmetic for hair according to claim 1, wherein in said general formula (1), $L^1$ is a functional group represented by the following general formula (2-1):

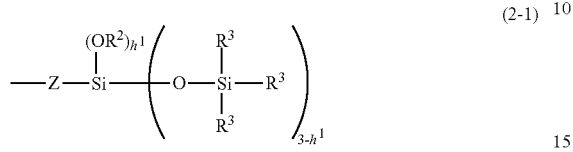
(2-1)

or represented by the following general formula (2-2):

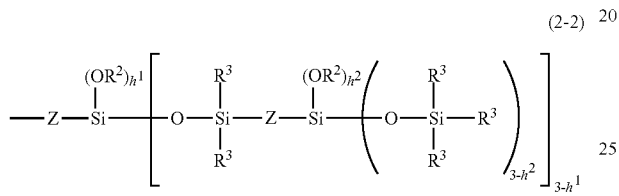
(2-2)

wherein $R^2$, $R^3$ and Z are the same as defined above; and each of $h^1$ and $h^2$ is independently a number ranging from 0 to 3.

3. The cosmetic for hair according to claim 1, wherein in said general formula (1), Q further comprises at least one hydrophilic unit selected from hydrophilic units represented by the following structural formulae (3-5) to (3-7):

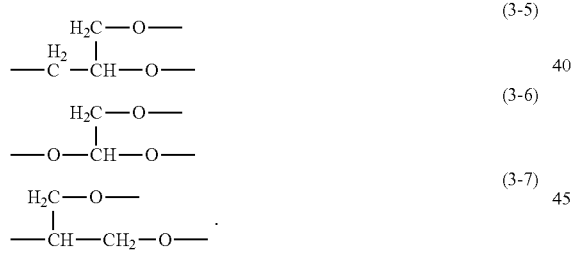
(3-5)
(3-6)
(3-7)

4. The cosmetic for hair according to claim 1, wherein said Q is a hydrophilic group represented by any one of the following general formulae (4-1) to (4-4):

$-R^4(-O-X^1{}_m-R^5)_p$ (4-1)

wherein $R^4$ is an organic group having (p+1) valences;
p is an integer ranging from 1 to 3;
each $X^1$ is independently at least one or more hydrophilic units selected from hydrophilic units represented by said structural formulae (3-1) to (3-4);
m is a number ranging from 1 to 100; and
$R^5$ is a hydrogen atom or a group selected from the group consisting of an alkyl group having 1 to 20 carbon atoms, an acyl group and a glycidyl group,

$-R^4(-O-X^2)_p$ (4-2)

wherein $R^4$ is the same group as defined above;
p is the same number as defined above; and
$X^2$ is a hydrophilic group represented by the following structural formula (4-2-1):

(4-2-1)

wherein at least one hydrophilic unit selected from the hydrophilic units represented by said structural formulae (3-1) to (3-4) independently binds to each of the two oxygen atoms,

$-R^4(-O-X^3)_p$ (4-3)

wherein $R^4$ is the same group as defined above;
p is the same number as defined above; and
$X^3$ is a hydrophilic group represented by the following structural formula (4-3-1):

(4-3-1)

wherein at least one hydrophilic unit selected from the hydrophilic units represented by said structural formulae (3-1) to (3-4) independently binds to each of the two oxygen atoms,

$-R^4(-O-X^4)_p$ (4-4)

wherein $R^4$ is the same group as defined above;
p is the same number as defined above; and
$X^4$ is a hydrophilic group represented by the following structural formula (4-4-1):

(4-4-1)

wherein at least one hydrophilic unit selected from the hydrophilic units represented by said structural formulae (3-1) to (3-4) independently binds to each of the two oxygen atoms.

5. The cosmetic for hair according to claim 1, wherein said (A) co-modified organopolysiloxane is represented by the following structural formula (1-1):

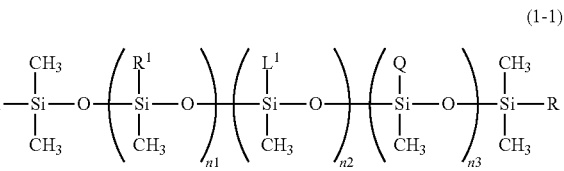
(1-1)

wherein
$R^1$, $L^1$ and Q are the same groups as defined above;
R is a group selected from $R^1$, $L^1$ and Q;
each of n1, n2 and n3 is independently a number ranging from 0 to 2,000, and n1+n2+n3 is a number ranging from 1 to 2,000, with the proviso that in the case of n2=0, at least one R is $L^1$, and in the case of n3=0, at least one R is Q.

6. The cosmetic for hair according to claim 1, wherein said (A) co-modified organopolysiloxane is represented by one of the following structural formulae (1-1-1) or (1-1-2):

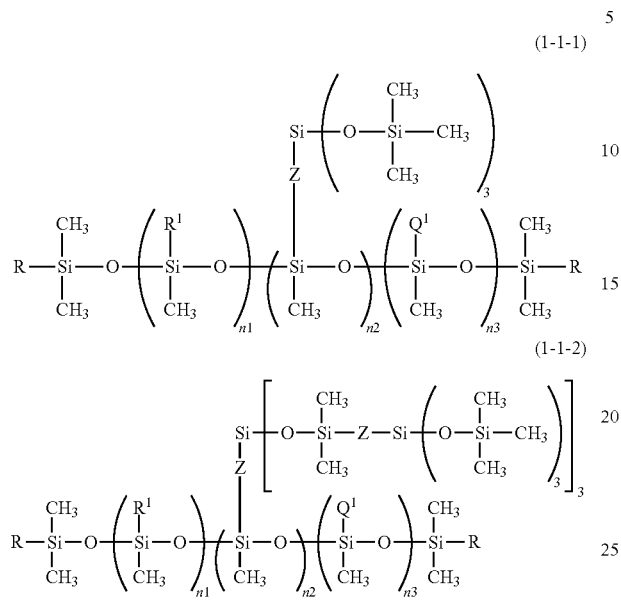

wherein
Z is the same group as defined above;
each R is independently a group selected from $R^1$, $L^1$ and $Q^1$;
$R^1$ and $L^1$ are the same groups as defined above;
$Q^1$ is a hydrophilic group selected from the group consisting of the following structural formulae (4-1-2), (4-2-2), (4-3-2) and (4-4-2):

$$—R^4(—O—X^1{}_m—R^5)_p \qquad (4\text{-}2\text{-}2)$$

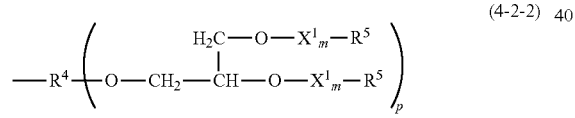 (4-2-2)

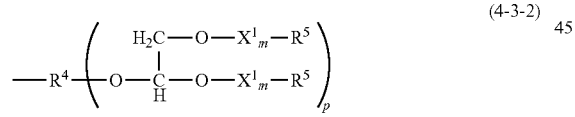 (4-3-2)

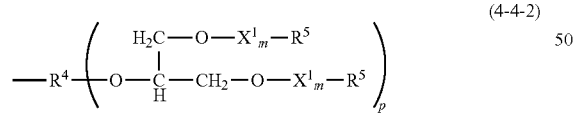 (4-4-2)

wherein $R^4$, p, $X^1$, m and $R^5$ are the same groups as defined above,
n1 is a number ranging from 10 to 2,000; n2 is a number ranging from 0 to 250; and
n3 is a number ranging from 0 to 250, with the proviso that in the case of n2=0, at least one R is $L^1$, and in the case of n3=0, at least one R is $Q^1$.

7. The cosmetic for hair according to claim 6, wherein in said structural formula (1-1-1) or (1-1-2), Z is independently a group selected from divalent organic groups represented by the following general formulae:

—$R^6$—

—$R^6$—CO—

—$R^6$—COO—$R^7$—

—CO—$R^6$—

—$R^6$—COO—$R^7$—

—$R^6$—CONH—$R^7$—

—$R^6$—$R^7$— wherein
each $R^6$ independently represents a substituted or non-substituted, and linear or branched, alkylene or alkenylene group having 2 to 22 carbon atoms or an arylene group having 6 to 22 carbon atoms; and
$R^7$ is a group selected from the group consisting of divalent organic groups represented by the following formulae:

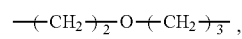

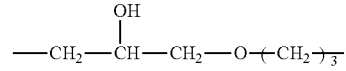

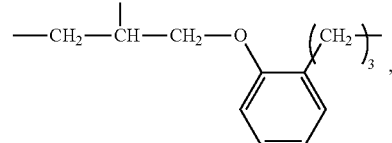

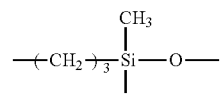

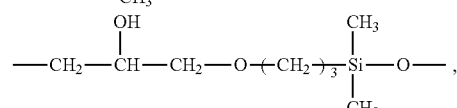

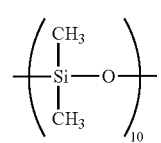

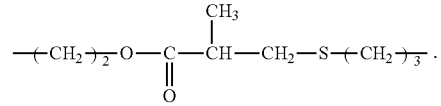

8. The cosmetic for hair according to claim 6, wherein in said structural formulae (4-1-2), (4-2-2), (4-3-2) and (4-4-2), p is 1; and $R^4$ is a group selected from divalent organic groups represented by the following general formulae (5-1), (5-1-2), (5-1-3) and (5-2):

—$R^8$— (5-1)

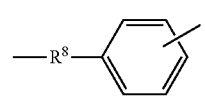 (5-1-2)

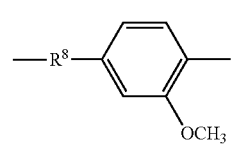 (5-1-3)

-continued

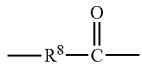
(5-2)

wherein
each $R^8$ independently represents a substituted or non-substituted, and linear or branched, alkylene or alkenylene group having 2 to 22 carbon atoms or an arylene group having 6 to 22 carbon atoms.

9. The cosmetic for hair according to claim 1, further comprising (B) an oil agent.

10. The cosmetic for hair according to claim 1, further comprising (C) a surfactant.

11. The cosmetic for hair according to claim 1, further comprising (D) a water-soluble polymer.

12. The cosmetic for hair according to claim 1, which is in the form of a cosmetic for cleansing hair, a cosmetic for conditioning hair, a cosmetic for styling hair, or a cosmetic for dyeing hair.

13. The cosmetic for cleansing hair according to claim 12, further comprising (C1) an anionic surfactant and (D1) a cationic water-soluble polymer.

14. The cosmetic for conditioning hair according to claim 12, further comprising (B2-1) a higher alcohol and (C2) a cationic surfactant.

15. The cosmetic for styling hair according to claim 12, which is in the form of a liquid, a cream, a solid, a paste, a gel, a mousse, or a spray.

16. The cosmetic for dyeing hair according to claim 12, further comprising (K) an oxidation hair-dyeing agent and/or (L) a direct dye.

* * * * *